US012594350B2

(12) United States Patent
Agnew et al.

(10) Patent No.: US 12,594,350 B2
(45) Date of Patent: Apr. 7, 2026

(54) CD8-SPECIFIC CAPTURE AGENTS, COMPOSITIONS, AND METHODS OF USING AND MAKING

(71) Applicant: Regeneron Pharmaceuticals, Inc., Tarrytown, NY (US)

(72) Inventors: Heather Dawn Agnew, Culver City, CA (US); Bert Tsunyin Lai, Culver City, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 762 days.

(21) Appl. No.: 15/478,596

(22) Filed: Apr. 4, 2017

(65) Prior Publication Data

US 2017/0319722 A1     Nov. 9, 2017

Related U.S. Application Data

(60) Provisional application No. 62/317,907, filed on Apr. 4, 2016.

(51) Int. Cl.

| | |
|---|---|
| *A61K 51/08* | (2006.01) |
| *C07K 7/06* | (2006.01) |
| *C07K 14/00* | (2006.01) |
| *C07K 14/705* | (2006.01) |
| *G01N 33/534* | (2006.01) |
| *G01N 33/569* | (2006.01) |
| *G01N 33/68* | (2006.01) |

(52) U.S. Cl.
CPC ............... *A61K 51/08* (2013.01); *C07K 7/06* (2013.01); *C07K 14/001* (2013.01); *C07K 14/70517* (2013.01); *G01N 33/534* (2013.01); *G01N 33/56972* (2013.01); *G01N 33/68* (2013.01); *G01N 2333/70517* (2013.01)

(58) Field of Classification Search
CPC ........ A61K 51/08; C07K 7/06; C07K 14/001; C07K 14/70517; G01N 33/534; G01N 33/56792; G01N 33/68; G01N 2333/70517; G01N 33/56972
See application file for complete search history.

(56) References Cited

U.S. PATENT DOCUMENTS

| | | | |
|---|---|---|---|
| 4,899,755 A | 2/1990 | Lauffer et al. | |
| 5,021,556 A | 6/1991 | Srinivasan | |
| 5,075,099 A | 12/1991 | Srinivasan et al. | |
| 5,118,797 A | 6/1992 | Jurisson et al. | |
| 5,183,653 A | 2/1993 | Linder et al. | |
| 5,364,613 A | 11/1994 | Sieving et al. | |
| 5,367,080 A | 11/1994 | Toner et al. | |
| 5,387,409 A | 2/1995 | Nunn et al. | |
| 5,474,756 A | 12/1995 | Tweedle et al. | |
| 5,547,668 A | 8/1996 | Kranz | |
| 5,608,110 A | 3/1997 | Ramalingam et al. | |
| 5,656,254 A | 8/1997 | Ramalingam et al. | |
| 5,662,885 A | 9/1997 | Pollak et al. | |
| 5,665,329 A | 9/1997 | Ramalingam et al. | |
| 5,688,487 A | 11/1997 | Linder et al. | |
| 5,720,934 A | 2/1998 | Dean et al. | |
| 5,780,006 A | 7/1998 | Pollak et al. | |
| 5,846,519 A | 12/1998 | Tweedle et al. | |
| 5,849,261 A | 12/1998 | Dean et al. | |
| 5,879,658 A | 3/1999 | Dean et al. | |
| 5,886,142 A | 3/1999 | Thakur et al. | |
| 5,976,495 A | 11/1999 | Pollak et al. | |
| 6,093,382 A | 7/2000 | Wedeking et al. | |
| 6,143,274 A | 11/2000 | Tweedle et al. | |
| 6,566,088 B1 | 5/2003 | McKnight | |
| 8,710,180 B2 | 4/2014 | Pitram | |
| 8,841,083 B2 | 9/2014 | Heath | |
| 8,906,830 B2 | 12/2014 | Agnew | |
| 9,188,584 B2 | 11/2015 | Agnew | |
| 9,221,889 B2 | 12/2015 | Pitram | |
| 9,239,332 B2 | 1/2016 | Heath | |
| 9,913,875 B2 | 3/2018 | Farrow | |
| 10,597,425 B2 | 3/2020 | Pfeilsticker et al. | |
| 10,598,671 B2 | 3/2020 | Heath | |
| 11,007,245 B2 | 5/2021 | Farrow | |
| 11,168,115 B2 | 11/2021 | Heath et al. | |
| 11,365,219 B2 * | 6/2022 | Heath ................ G01N 33/6842 |
| 11,365,220 B2 * | 6/2022 | Pfeilsticker .............. C07K 7/08 |
| 11,723,944 B2 | 8/2023 | Farrow et al. | |
| 11,919,972 B2 | 3/2024 | Eliasen | |
| 2006/0153839 A1 | 7/2006 | Mohamed | |
| 2010/0009896 A1 | 1/2010 | Agnew et al. | |
| 2011/0177109 A1 | 7/2011 | Smith, III | |
| 2011/0263515 A1 | 10/2011 | Agnew | |
| 2012/0202219 A1 | 8/2012 | Agnew | |

(Continued)

FOREIGN PATENT DOCUMENTS

| | | |
|---|---|---|
| CN | 1292029 A | 4/2001 |
| CN | 102159949 A | 8/2011 |
| EP | 2719706 | 4/2014 |
| WO | 8606605 A1 | 11/1986 |
| WO | 9103200 A1 | 3/1991 |
| WO | 9503280 A1 | 2/1995 |
| WO | 9506633 A1 | 3/1995 |
| WO | 9528179 A1 | 10/1995 |
| WO | 9528967 A1 | 11/1995 |
| WO | 9603427 A1 | 2/1996 |
| WO | 9623526 A1 | 8/1996 |
| WO | 9736619 A2 | 10/1997 |
| WO | 98/18496 | 5/1998 |
| WO | 98/18497 | 5/1998 |

(Continued)

OTHER PUBLICATIONS

Handl et al., Expert Opin. Ther. Targets (2004) 8(6):565-586 (Year: 2004).*

(Continued)

*Primary Examiner* — Joseph Fischer
(74) *Attorney, Agent, or Firm* — Fenwick & West LLP

(57) ABSTRACT

The present application provides stable peptide-based CD8 capture agents and methods of use as detection agents. The application further provides methods of manufacturing CD8 capture agents.

13 Claims, 31 Drawing Sheets

Specification includes a Sequence Listing.

(56) References Cited

U.S. PATENT DOCUMENTS

| | | | | |
|---|---|---|---|---|
| 2012/0252071 A1* | 10/2012 | Greif | .............. | C12Y 207/07006 |
| | | | | 435/91.3 |
| 2014/0271462 A1* | 9/2014 | Ho | .................... | A61K 51/1027 |
| | | | | 424/1.49 |
| 2014/0302998 A1* | 10/2014 | Heath | ...................... | C07K 7/02 |
| | | | | 506/1 |
| 2015/0099658 A1 | 4/2015 | Pfeilsticker | | |
| 2015/0132314 A1 | 5/2015 | Masternak | | |
| 2015/0344523 A1 | 12/2015 | Deyle | | |
| 2016/0331800 A1 | 11/2016 | Farrow | | |
| 2018/0364253 A1 | 12/2018 | Agnew | | |
| 2019/0177367 A1 | 6/2019 | Heath et al. | | |
| 2020/0291391 A1 | 9/2020 | Eliasen et al. | | |
| 2020/0407712 A1 | 12/2020 | Boyd | | |
| 2022/0211648 A1 | 7/2022 | Agnew | | |
| 2022/0380409 A1 | 12/2022 | Heath et al. | | |
| 2024/0174715 A1 | 5/2024 | Eliasen | | |
| 2025/0026790 A1 | 1/2025 | Farrow et al. | | |
| 2025/0130235 A1 | 4/2025 | Heath et al. | | |
| 2025/0186571 A1 | 6/2025 | Heath et al. | | |
| 2025/0264471 A1 | 8/2025 | Heath et al. | | |
| 2025/0270259 A1 | 8/2025 | Pfeilsticker et al. | | |

FOREIGN PATENT DOCUMENTS

| | | | |
|---|---|---|---|
| WO | 9818496 | A2 | 5/1998 |
| WO | 9818497 | A2 | 5/1998 |
| WO | 9846612 | A1 | 10/1998 |
| WO | 9852618 | A1 | 11/1998 |
| WO | 99/17809 | | 4/1999 |
| WO | 9917809 | A2 | 4/1999 |
| WO | 99/21576 | | 5/1999 |
| WO | 9921576 | A1 | 5/1999 |
| WO | 02/083064 | | 10/2002 |
| WO | 03/006620 | | 1/2003 |
| WO | 2005/113762 | | 12/2005 |
| WO | 2007/050963 | | 5/2007 |
| WO | 2009/051555 | | 4/2009 |
| WO | 2009051555 | A2 | 4/2009 |
| WO | 2009/105746 | | 8/2009 |
| WO | 2009155420 | A1 | 12/2009 |
| WO | 2010/135431 | | 11/2010 |
| WO | 2011/057347 | | 5/2011 |
| WO | 2012/106651 | | 8/2012 |
| WO | 2012106651 | A2 | 8/2012 |
| WO | 2012106671 | A1 | 8/2012 |
| WO | 2013009869 | A2 | 1/2013 |
| WO | 2013/034982 | | 3/2013 |
| WO | 2013033561 | A1 | 3/2013 |
| WO | 2014/056813 | | 4/2014 |
| WO | 2014074907 | A1 | 5/2014 |
| WO | 2014/205317 | | 12/2014 |
| WO | 2017/011769 | | 1/2017 |
| WO | 2017/176769 | | 10/2017 |
| WO | 2018/064597 | | 4/2018 |
| WO | 2018/111580 | | 6/2018 |
| WO | 2018/170096 | | 9/2018 |
| WO | 2018/200551 | | 11/2018 |
| WO | 2020/127227 | | 6/2020 |

OTHER PUBLICATIONS

Artali et al., Il Farmaco 60 (2005) 485-495 (Year: 2005).*
Epitope Mapping Protocols, 2nd Edition, Reineke and Schutkowski Eds., 2009, Humana Press, pp. 4-7 provided (Year: 2009).*
Josan et al., Bioconjug Chem. Jul. 20, 2011; 22(7): 1270-1278 (Year: 2011).*
Merriam-Webster online definition of "correspond" downloaded Jun. 29, 2020 from internet, https://www.merriam-webster.com/dictionary/correspond (Year: 2020).*
MacRaild et al., Structure 24, 148-157, Jan. 5, 2016 (Year: 2016).*
Hudson et al, Scientific Reports vol. 2 No. 706, 2012, pp. 1-9 (Year: 2012).*

Matsuura, Journal of General Virology (2001), 82, 1695-1702 (Year: 2001).*
Millward et al., Integr Biol (Camb). Jan. 2013 ; 5(1): 87-95 (Year: 2013).*
Melenhorst et el., J Immunol Methods. Sep. 30, 2008; 338(1-2): 31-39 (Year: 2008).*
MacRaild et al., PLOS ONE I DOI: 10.1371/journal.pone.0119899, Mar. 15, 2015 (Year: 2015).*
Pansca and Tompa, PLoS ONE, www.plosone.org Apr. 1, 2012, vol. 7, Issue 4, e34687, 10 pages (Year: 2012).*
Cell, vol. 50, 667, Aug. 26, 1987 (Year: 1987).*
Koonin EV, Galperin MY. Sequence—Evolution—Function: Computational Approaches in Comparative Genomics. Boston: Kluwer Academic; 2003, Chapter 2 Evolutionary Concept in Genetics and Genomics (Year: 2003).*
Smith and Greany, Org. Lett., vol. 15, No. 18, 4826-4829, 2013 (Year: 2013).*
Agalave et al., Chem. Asian J. 2011, 6, 2696-2718 (Year: 2011).*
Nakano et al., The Journal of Biological Chemistry, vol. 258, No. 20, Issue of Oct. 25. pp. 12409-12412, 1983 (Year: 1983).*
Janeway's Immunobiology, 9th Edition, 2017, pp. 150-151 (Year: 2017).*
Farrow et al., Angew. Chem. Int. Ed. 2015, 54, 7114-7119 (Year: 2015).*
Handl et al., Expert Opin. Ther. Targets (2004) 8(8):585-588 (Year: 2004).*
Sormanni et al., PNAS, Aug. 11, 2015, vol. 112, No. 32, 9902-9907 (Year: 2015).*
Wooldridge et al., Immunology, 126, 147-164 2009 (Year: 2009).*
GenBank: AAH25715.1 [retrieved May 11, 2020][retrieved from https://blast.ncbi.nlm.nih.gov/Blast.cgi#AAH25715][Submitted (Mar. 6, 2002)] (Year: 2002).*
Chen et al., Adv Drug Deliv Rev. Oct. 15, 2013; 65(10): 1357-1369 (supplied as paginated from p. 1) (Year: 2013).*
Testa et al., Biomarker Research 2014, 2:4 (Year: 2014).*
Das et al., Angew Chem Int Ed Engl. Nov. 2, 2015; 54(45) (V) (Year: 2015).*
Mamidyala and Finn, Chem. Soc. Rev., 2010, 39, 1252-1261 (Year: 2010).*
Sormanni et al., PNAS, Aug. 11, 2015, vol. 112, No. 32, Supplemental Materials (Year: 2015).*
Chattopadhyay et al., Cytometry Part A, 73A: 1001-1009, 2008 (Year: 2008).*
J.P. Boersma, 2011, Theory of condensed matter, Radboud Univ. Nijmegen, 18 pages (Year: 2011).*
Genbank ABX57447.1, 2016, cytosolic malate dehydrogenase, partial [Hepialus humuli], downloaded from the internet following STN search Jun. 20, 2025 (Year: 2016).*
Agnew et al. (Jun. 22, 2009) "Iterative In Situ Click Chemistry Creates Antibody-like Protein-Capture Agents," Angewandte Chemie International Edition. 48(27):4944-4948.
Alexander et al. (1998) "Intracranial black-blood MR angiography with high-resolution 3D fast spin echo," Magnetic Resonance in Medicine. 40(2):298-310.
Altschul et al. (1997) "Gapped BLAST and PSI-BLAST: a new generation of protein database search programs," Nucleic Acids Research. 25(17):3389-3402.
Claverie et al. (1993) "Information enhancement methods for large scale sequence analysis," Computers & Chemistry. 17(2):191-201.
Edelman et al. (1990) "Extracranial carotid arteries: evaluation with" black blood" MR angiography," Radiology. 177(1):45-50.
Fitzer-Attas et al. (Jan. 1998) "Harnessing Syk family tyrosine kinases as signaling domains for chimeric single chain of the variable domain receptors: optimal design for T cell activation, " The Journal of Immunology. 160(1):145-154.
Goodrich et al. (1996) "A quantitative study of ramped radio frequency, magnetization transfer, and slab thickness in three-dimensional time-of-flight magnetic resonance angiography in a patient population," Investigative Radiology. 31(6):323-332.
Iwata et al. (2000) "A new, convenient method for the preparation of 4-[18 F] fluorobenzyl halides," Applied Radiation and Isotopes. 52(1):87-92.

US 12,594,350 B2

Page 3

(56) References Cited

OTHER PUBLICATIONS

Klemm (1984) "Manual Edman degradation of proteins and peptides," Proteins. Methods in Molecular Biology. 1:243-254.

Kroger et al. (2007) "Dose-dependent modulation of CD8 and functional avidity as a result of peptide encounter," Immunology. 122(2):167-178.

Lee et al. (2008) "Rapid microwave-assisted CNBr cleavage of bead-bound peptides," Journal of Combinatorial Chemistry. 10(6):807-809.

Liu et al. (1999) "99mTc-labeled small peptides as diagnostic radiopharmaceuticals," Chemical Reviews. 99(9):2235-2268.

Myers et al. (1988) "Optimal alignments in linear space," Bioinformatics. 4(1):11-17.

Poethko et al. (2004) "Two-step methodology for high-yield routine radiohalogenation of peptides: 18F-labeled RGD and octreotide analogs," Journal of Nuclear Medicine. 45(5):892-902.

Schottelius et al. (2004) "First 18F-labeled tracer suitable for routine clinical imaging of sst receptor-expressing tumors using positron emission tomography," Clinical Cancer Research. 10(11):3593-3606.

Tumeh et al. (2014) "PD-1 blockade induces responses by inhibiting adaptive immune resistance," Nature. 515(7528):568-571.

Wilson et al. (1990) "Reductive amination of [18F] fluorobenzaldehydes: Radiosyntheses of [2-18F]-and [4-18F] fluorodexetimides," Journal of Labelled Compounds and Radiopharmaceuticals. 28(10):1189-1199.

Wooldridge et al. (Feb. 26, 2010) "MHC class I molecules with superenhanced CD8 binding properties bypass the requirement for cognate TCR recognition and nonspecifically activate CTLs," The Journal of Immunology. 184(7):3357-3366.

Wootton et al. (1993) "Statistics of local complexity in amino acid sequences and sequence databases," Computers & Chemistry. 17(2):149-163.

International Search Report corresponding to International Patent Application No. PCT/US2017/025962, dated Sep. 20, 2017.

Agnew, et al., "Protein-Catalyzed Capture Agents", Chemical Reviews, 119(17):9950-9970 (2019).

Bianchi et al., "Vaccination with peptide mimetics of the gp41 prehairpin fusion intermediate yields neutralizing antisera against HIV-1 isolates", PNAS, 107(23):10655-10660 (2010).

Chan, et al., "Dual-targeting anti-angiogenic cyclic peptides as potential drug leads for cancer therapy", Scientific Reports, 6:35247, 13 pages (2016).

Chauhan, et al. "The Taming of the Cell Penetrating Domain of the HIV Tat: Myths and Realities", J. Control Release, 117(2): 148-162 (2007).

Chen, et al., "Fusion protein linkers: property, design and functionality", Adv. Drug Deliv. Rev., 65(10): 1357-1369 (2013).

Cheong, et al., "A patent review of IDO1 inhibitors for cancer", Expert Opinion on Therapeutic Patents, 28(4):317-330 (2018).

Choksi, et al., "A CD8 DE loop peptide analog prevents graft-versus-host disease in a multiple minor histocompatibility antigen-mismatched bone marrow transplantation model", Biology of Blood and Marrow Transplantation, 10(10):669-680 (2004).

Coppock, et al., "Peptide-based protein capture agents with high affinity, selectivity, and stability as antibody replacements in bio detection assays", Proc. of SPIE, 9107:910711-1 (2014).

Das, et al., "A General Synthetic Approach for Designing Epitope Targeted Macrocyclic Peptide Ligands", Angewandte Chemie International Edition, 54(45):13219-13224 (2015).

Dieck, et al., "Development of bispecific molecules for the in-situ detection of protein-protein interactions and protein phosphorylation", Cell & Biology, 21:357-368 (2014).

Eiber, et al., "Prostate-Specific Membrane Antigen Ligands for Imaging and Therapy", The Journal of Nuclear Medicine, 58(Supplement 2):67S-76S (2017).

Farrow, et al., "Epitope Targeting of Tertiary Protein Structure Enables Target-Guided Synthesis of a Potent In-Cell Inhibitor of Botulinum Neurotoxin", Angew Chem Int Ed Engl., 54(24): 7114-7119 (2015).

Fisher, et al, "Trivalent Gd-DOTA reagents for modification of proteins", RSC Adv., 5: 96194-96200 (2015).

Fitzer-Attas, et al., "Harnessing Syk family tyrosine kinases as signaling domains for chimeric single chain of the Variable Domain Receptors: Optimal Design for T Cell Activation", J. Immunol., 160(1):145-154 (1998).

Gao, et al., "Crystal structure of the complex between human CD8alpha(alpha) and HLA-A2", Nature, 387:630-4 (1997).

Hill, et al., "Constraining Cyclic Peptides to Mimic Protein Structure Motifs", Angewandte Chemie, 53(48):13020-13041 (2014).

Hirai, et al., "MK-2206, an Allosteric Akt Inhibitor, Enhances Antitumor Efficacy by Standard Chemotherapeutic Agents or Molecular Targeted Drugs In vitro and In vivo", Molecular Cancer Therapeutics, 9(7): 1956-1967 (2010).

Lai, et al., "Epitope-Targeted Macrocyclic Peptide Ligand with Picomolar Cooperative Binding to Interleukin-17F", Chemistry, 24(15):3760-3767 (2018).

Li, et al., "Identification of the CD8 DE loop as a surface functional epitope. Implications for major histocompatibility complex class 1 binding and CD8 inhibitor design", Journal Of Biological Chemistry, 273(26): 16442-16445 (1998).

Lin, et al., "Inhibition of HIV-1 Tat-mediated transcription by a coumarin derivative, BPRHIV001, through the Akt pathway", Journal of Virology, 85(17):9114-9126 (2011).

Lindlsey, et al., "The P13K/Akt Pathway: Recent Progress in the Development of ATP-Competitive and Allosteric Akt Kinase Inhibitors", Current Cancer Drug Targets, 8: 7-18 (2008).

Ma, et al., "A cyclic peptide-polymer probe for the detection of Clostridium botulinum neurotoxin serotype A", Toxicon, 47(8):901-908 (2006).

Mabry, et al., "Engineering of stable bispecific antibodies targeting IL-17 A and IL-23", Protein Engineering, Design & Selection, 23(3):115-127 (2010).

Mamidyala et al., 'In situ click chemistry: probing the binding landscapes of biological molecules, Chemical Society Reviews, 39(4):1252-1261 (2010).

Manea, et al., "Antibody Recognition and Conformational Flexibility of a Plaque-Specific-Amyloid Epitope Modulated by Non-native Peptide Flanking Regions", J. Med. Chem., 51(5):1150-1161 (2008).

Meyers and Miller, "Optimal alignments in linear space", Comp Applic. Biol. Sci., 4(1):11-17 (1988).

Millward, et al., "In situ click chemistry: from small molecule discovery to synthetic antibodies", Integr. Biol (Camb)., 5(1): 87-95 (2013).

Millward, et al., "Iterative in situ click chemistry assembles a branched capture agent and allosteric inhibitor for Akt1", JACS, 133(45):18280-18288 (2011).

Miossec, "Update on interleukin-17: a role in the pathogenesis of inflammatory arthritis and implication for clinical practice", RMD Open, 3(1):e000284 (2017).

Mor, et al., Mimicking the Structure of the V3 Epitope Bound to HIV-1 Neutralizing Antibodies', Biochemistry, 48(15):3288-3303 (2009).

Muller, et al., "DOTA Conjugate with an Albumin-Binding Entity Enables the First Folic Acid-Targeted 177Lu-Radionuclide Tumor Therapy in Mice", The Journal Of Nuclear Medicine, 54(1):124-131 (2013).

Muller, et al., "Folic acid conjugates for nuclear imaging of folate receptor-positive cancer", J. Nucl. Med., 52(1): 1-4 (2011).

Nag et al., "A chemical epitope-targeting strategy for protein capture agents: the serine 474 epitope of the kinase Akt2", Angewandte Chemie International Edition, 52:13975-13979 (2013).

O'Shannessy, et al., "Characterization of the human folate receptor alpha via novel antibody-based probes", Oncotarget, 2(12):1227-1243 (2011).

Pfeilsticker, et al., "A cocktail of thermally stable, chemically synthesized capture agents for the efficient detection of anti-gp41 antibodies from human sera", PLoS One, 8(10):Article No. e76224, 5 pages (2013).

Saito, et al., "Identification of anti-CD98 antibody mimotopes for inducing antibodies with antitumor activity by mimotope immunization", Cancer Science, 105(4): 396-401 (2014).

(56)     References Cited

OTHER PUBLICATIONS

Sarbassov, et al., "Phosphorylation and regulation of Akt/PKB by the rictor-mTOR complex", *Science, American Association for The Advancement Of Science*, 307(5712): 1098-1101 (2005).

Schweinsberg, et al., "Novel glycated [99mTc(CO)3]-labeled bombesin analogues for improved targeting of gastrin-releasing peptide receptor-positive tumors", *Bioconjugate Chem.*, 19(12):2432-2439 (2008).

Son, et al., "New Cyclic Lipopeptides of the Iturin Class Produced by Saltern-Derived *Bacillus* sp. KCB14S006", *Marine Drugs*, 14(4): 72 (2016).

Subramanyam, et al., "Inhibition of Protein Kinase Akt1 by Apoptosis Signal-regulating Kinase-1 (ASK1) Is Involved in Apoptotic Inhibition of Regulatory Volume Increase", *Journal of Biological Chemistry*, 285(9): 6109-6117(2010).

Tang et al., "Chimeric molecules facilitate the degradation of androgen receptors and repress the growth of LNCaP cells", *Asian Journal of Andrology*, 11(1): 119-126 (2009).

Tao, et al., "Expression, purification and identification of an immunogenic fragment in the ectodomain of prostate-specific membrane antigen", *Experimental And Therapeutic Medicine*, 11(3): 747-752 (2016).

Todorova, et al., "Biochemical nature and mapping of PSMA epitopes recognized by human antibodies induces after immunization with gene-based vaccines", *Anticancer Research*, 25: 4727-4732 (2005).

Torres, et al., "A revolutionary therapeutic approach for psoriasis: bi specific biological agents", *Expert Opinion on Investigational Drugs*, 25(7): 751-754 (2016).

Wang, et al., "Epitope Mapping Using Phage-Display Random Fragment Libraries", Epitope Mapping Protocols, *Methods in Molecular Biology*, 524: 315-332 (2009). Abstract Only.

Wang, et al., "Radioligand Therapy of Prostate Cancer with a Long-Lasting Prostate-Specific Membrane Antigen Targeting Agent 90 Y-DOTA-EB-MCG", *Bioconjugate Chemistry*, 29(7): 2309-2315 (2018).

Zhang, et al., "Structure and function of interleukin-17 family cytokines", *Protein & Cell*, 2(1): 26-40 (2011).

Almehdi, et al., "SARS-CoV-2 spike protein: pathogenesis, vaccines, and potential therapies", Infection, 49: 855-876 (2021).

BPS Bioscience: INCB024360 Analog Data Sheet (2012).

Glaven, et al., "Linking single domain antibodies that recognize different epitopes on the same target", Biosensors, 2:43-56 (2012).

He, et al., "Vaccine design based on 16 epitopes of SARS-CoV-2 spike protein", Journal of Medical Virology, 93:2115-2131 (2021).

Kirszbaum, et al., "The alpha-chain of murine CD8 lacks an invariant lg-like disulfide bond but contains a unique intrachain loop instead", J. Immunol., 142(11):3931-6 (1989).

Wang, et al., "Structural basis of the CD8 alpha beta/MHC class I interaction: focused recognition orients CD8 beta to a T cell proximal position", J. Immunol., 183(4):2554-64 (2009).

Yang, et al., "Structural biology of SARS-CoV-2 and implications for therapeutic development", Nature Reviews, 19:685-700 (2021).

* cited by examiner

A.

B.

*CD8α loop1*            SQFRVSPLDRTWNLGETVELKSQ (amino acids 1-23)
*Epitope1*       Biotin-PEG$_3$-SQFRVSPLD[Az4]TWNLGETVELKSQ

*CD8α loop2*            FLLYLSQNKPKAAEGLDTQR (amino acids 48-67)
*Epitope2*       Biotin-PEG$_3$-FLLYLSQNKP[Az4]AAEGLDTQR

Figure 2

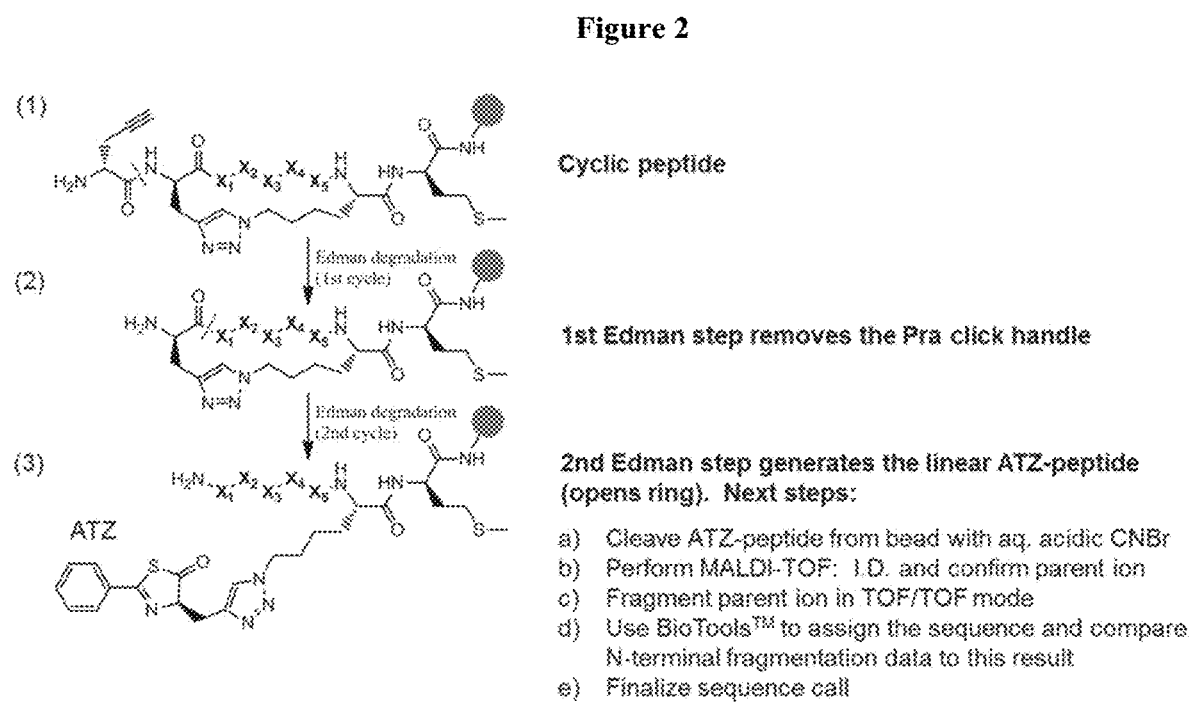

(1)  Cyclic peptide (2)  1st Edman step removes the Pra click handle (3)  2nd Edman step generates the linear ATZ-peptide
(opens ring).  Next steps:

a) Cleave ATZ-peptide from bead with aq. acidic CNBr
b) Perform MALDI-TOF:  I.D. and confirm parent ion
c) Fragment parent ion in TOF/TOF mode
d) Use BioTools™ to assign the sequence and compare
   N-terminal fragmentation data to this result
e) Finalize sequence call

Figure 3
A.
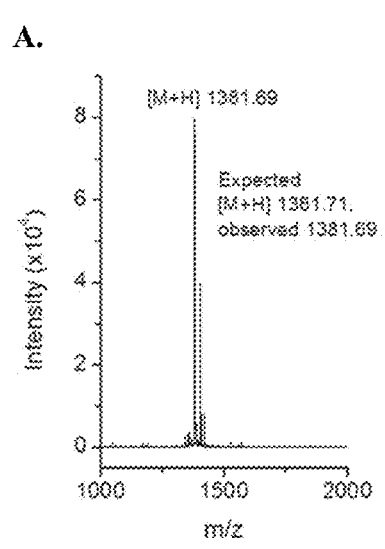
B.
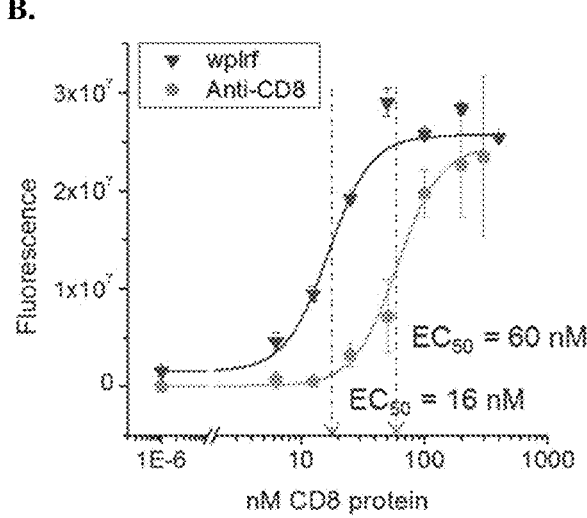
C.
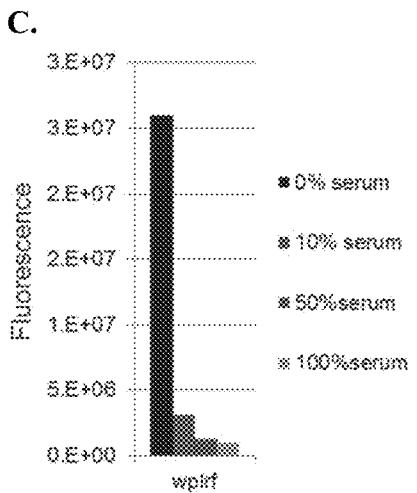
D.
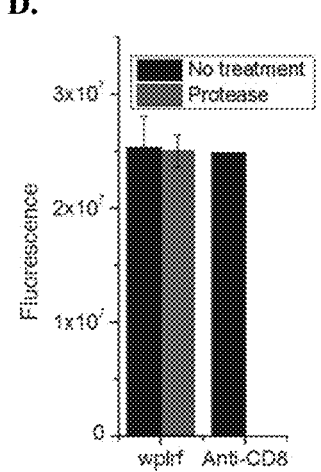

Figure 4
A.
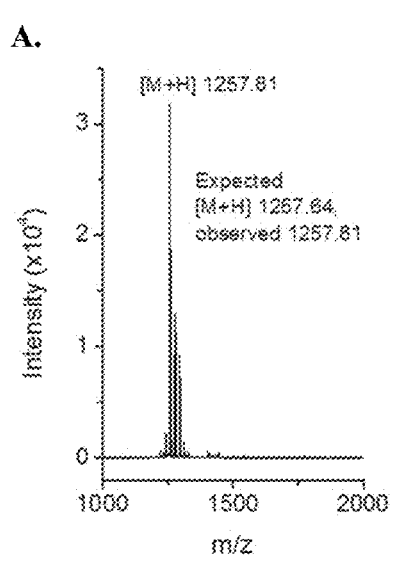
B.
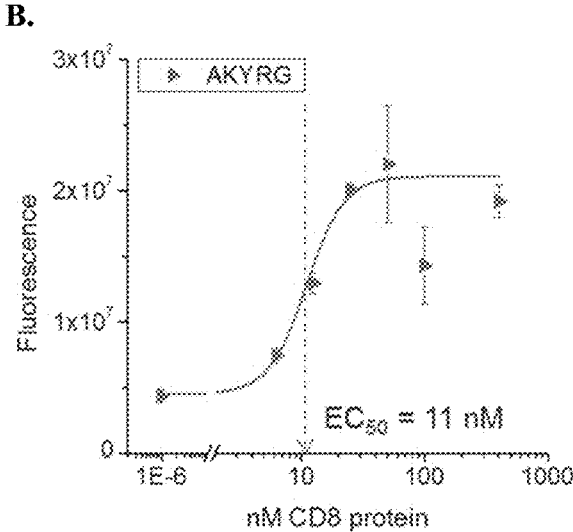
C.
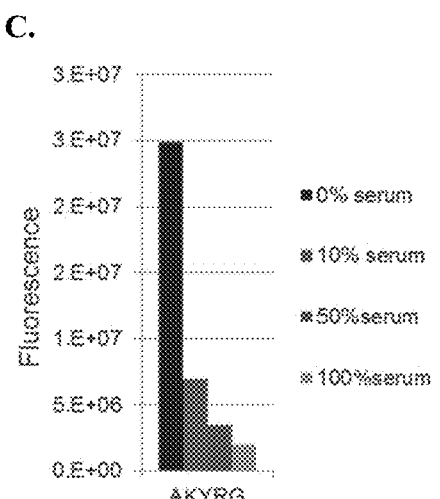
D.
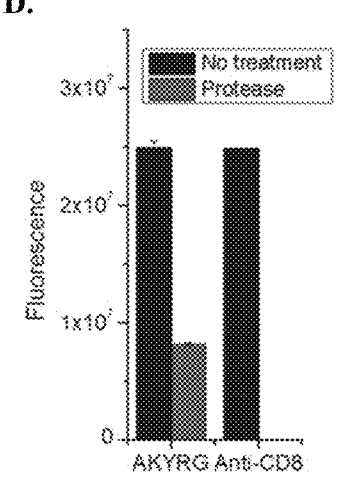

Figure 5
A.
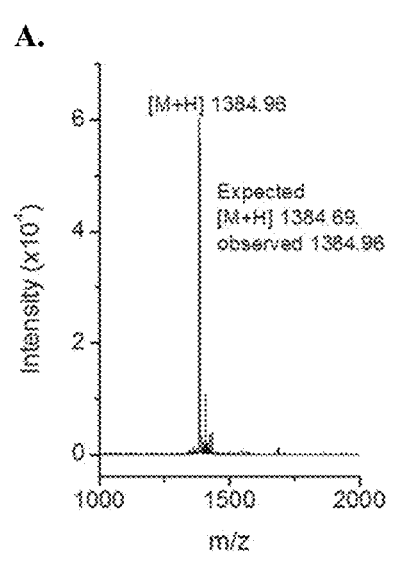
B.
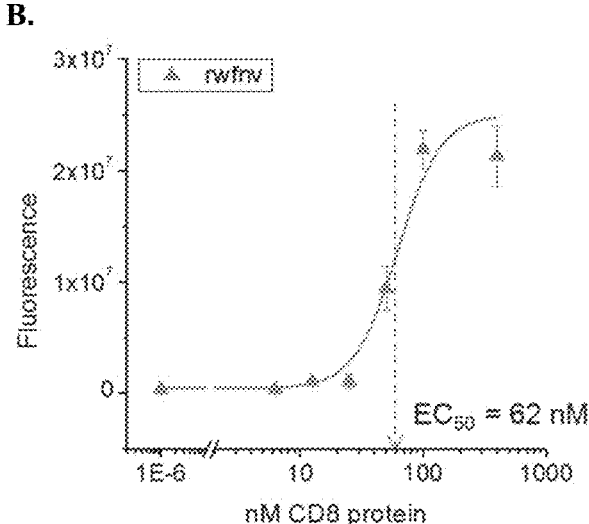
C.
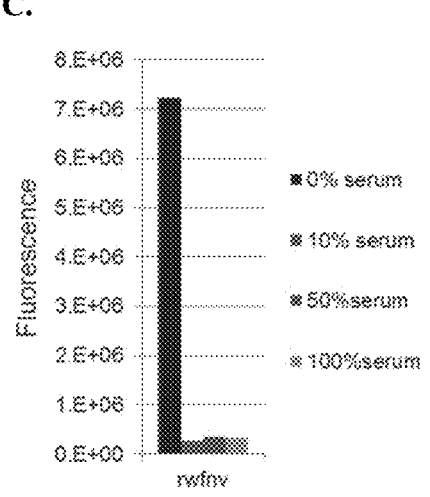
D.
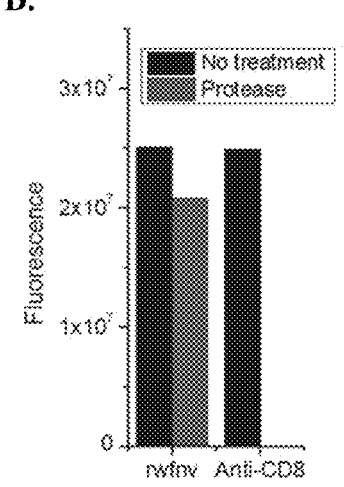

Figure 6
A.
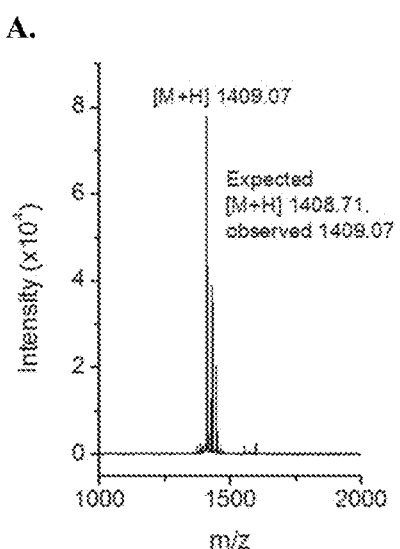
B.
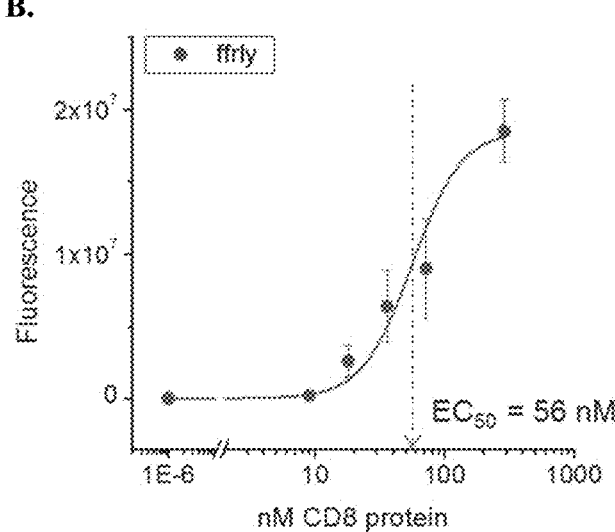
C.
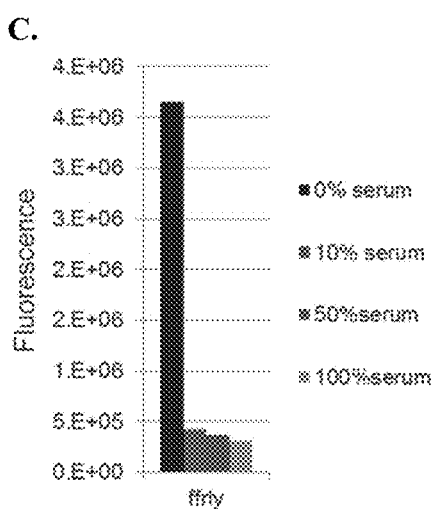
D.
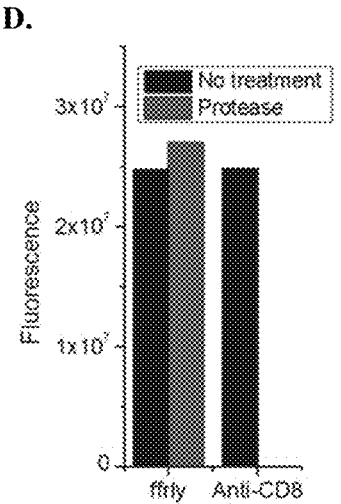

Figure 7
A.
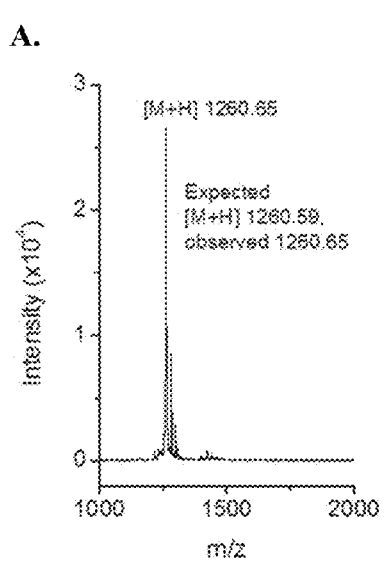
B.
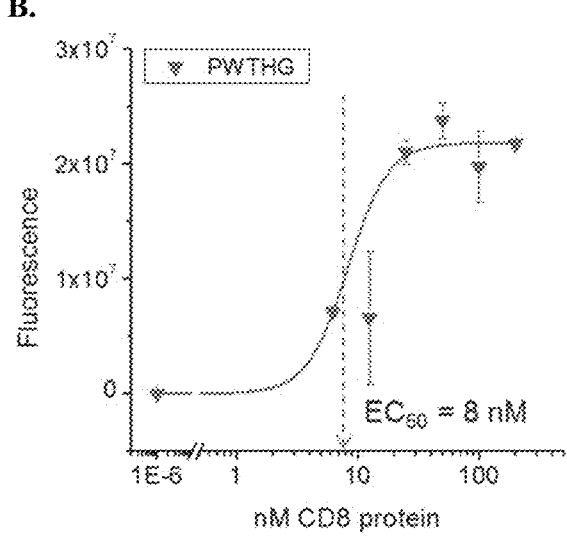
C.
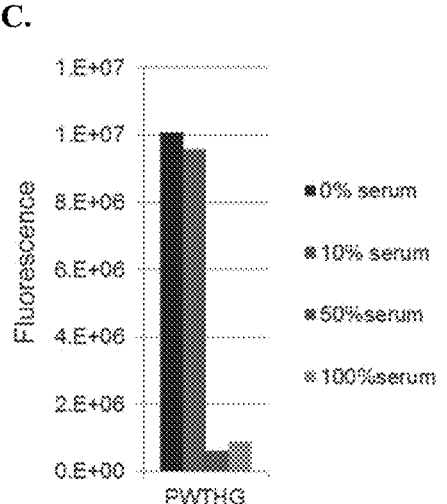
D.
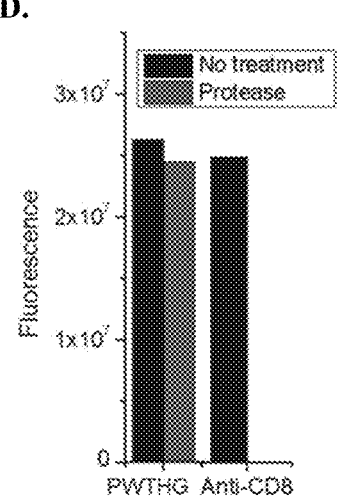

Figure 8
A.
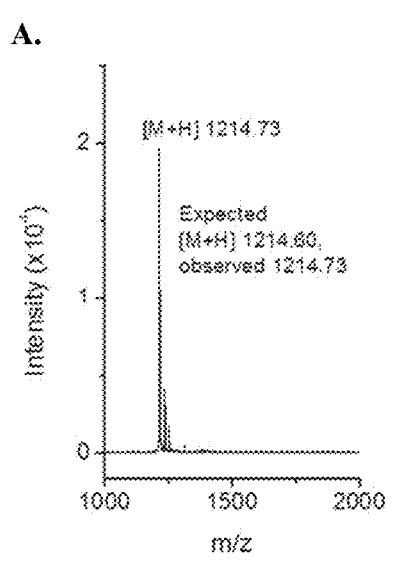
B.
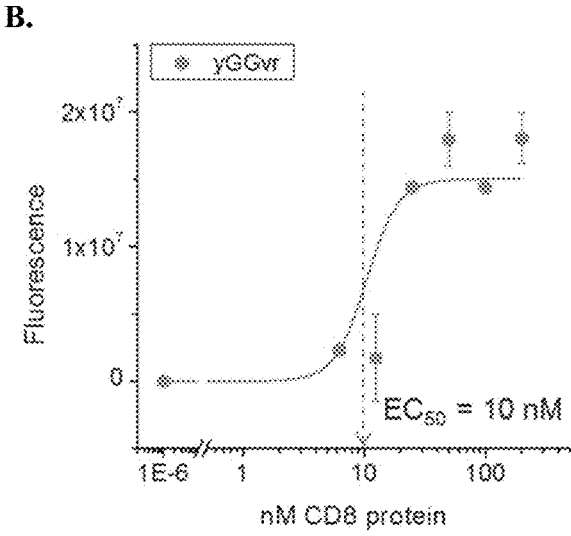
C.
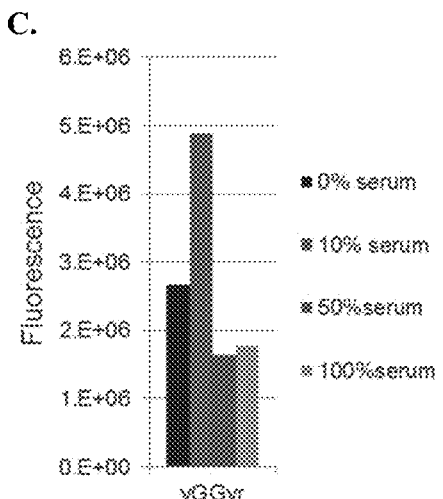
D.
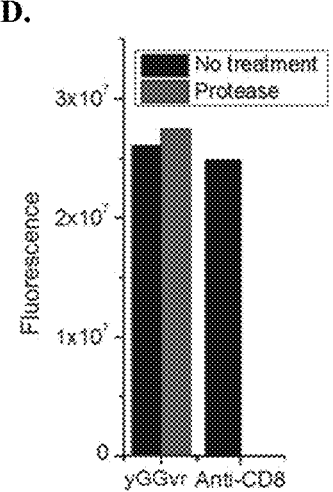

Figure 9
A.
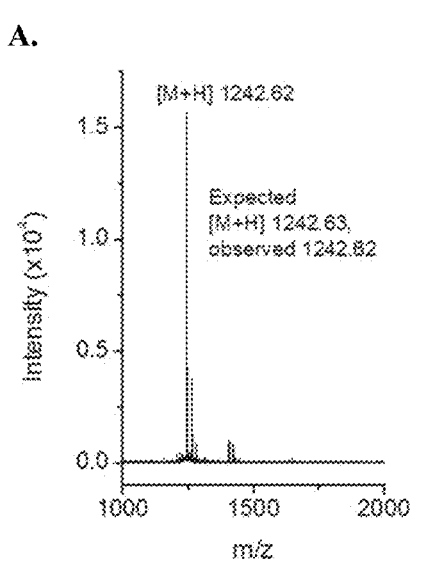
B.
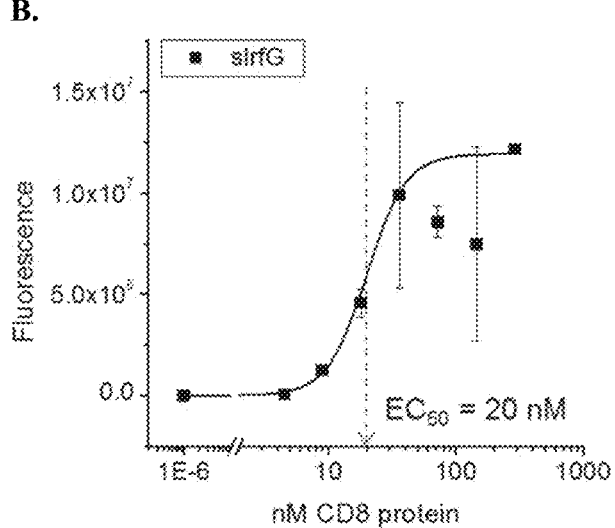
C.
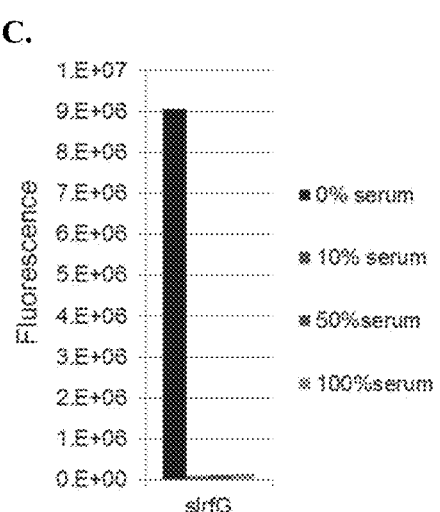
D.
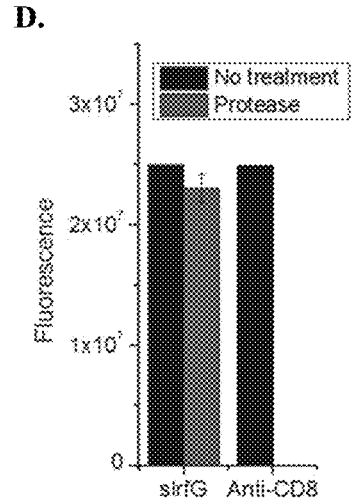

Figure 10
A.
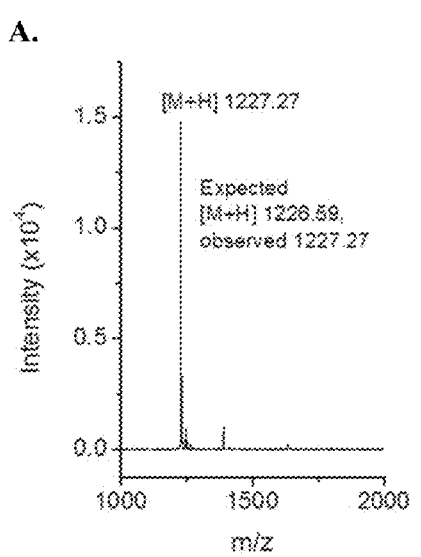
B.
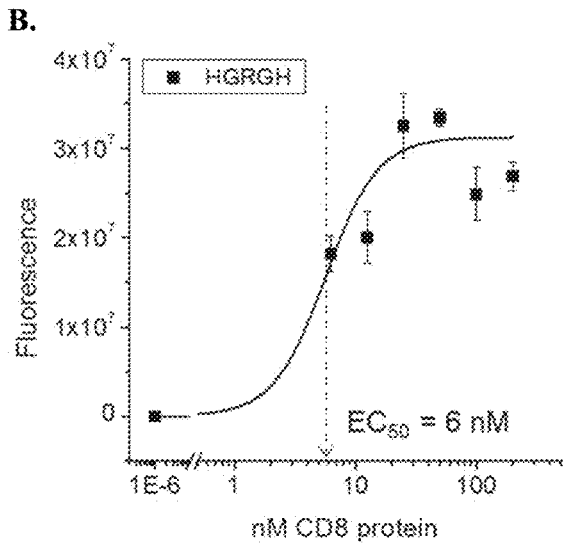
C.
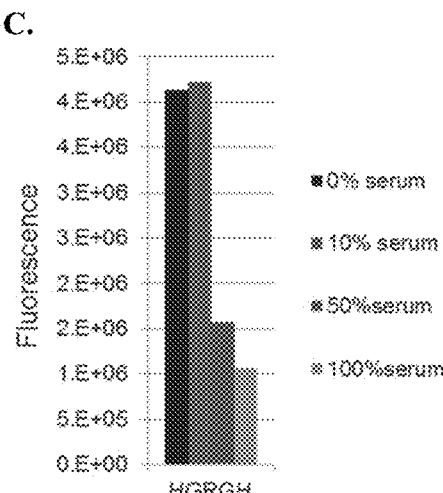

Figure 11
A.
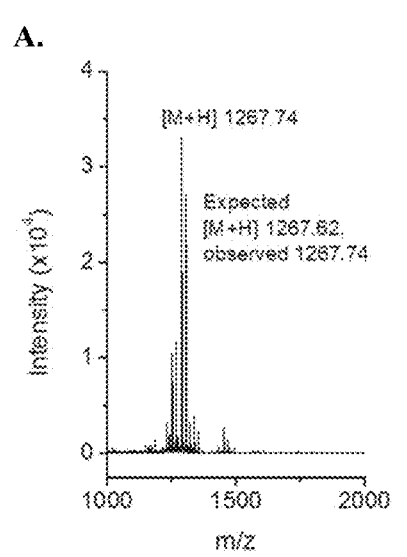
B.
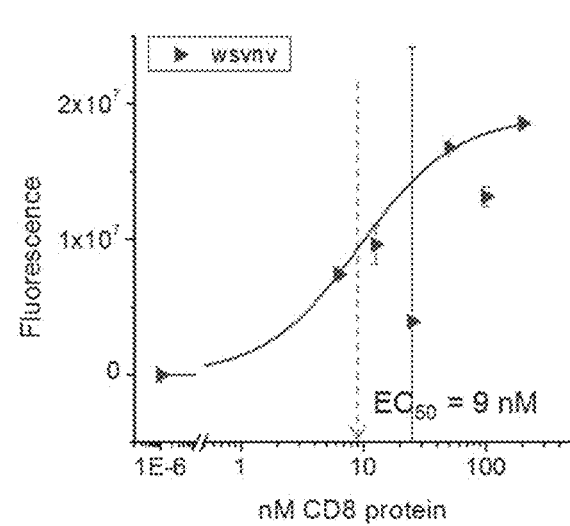
C.
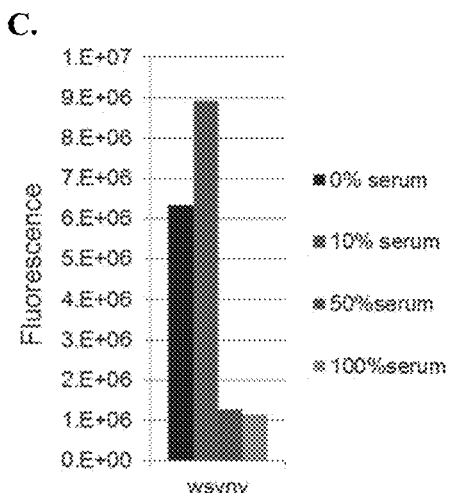
D.
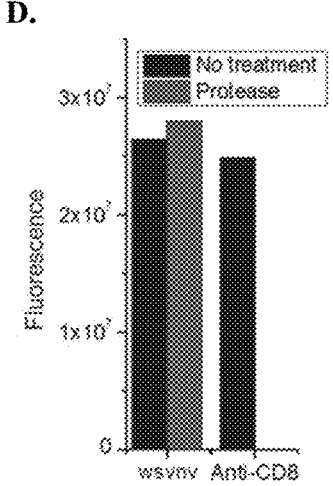

Figure 12
A.
    1) His$_6$-PEG$_3$-SQFRVSPLD<u>R</u>*GGGGGGGGGGGGGG* (CD8 Epitope1N)
    2) His$_6$-PEG$_3$-*GGGGGGGGG*<u>R</u>TWNLGETVELKSQ (CD8 Epitope1C)
B.
    1) His$_6$-PEG$_3$-FLLYLSQNKP<u>K</u>*GGGGGGGGG* (CD8 Epitope2N)
    2) His$_6$-PEG$_3$-*GGGGGGGGGGG*<u>K</u>AAEGLDTQR (CD8 Epitope2C)
C.
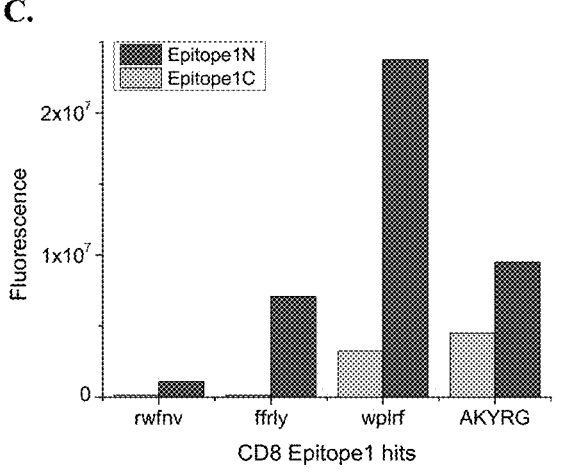
D.
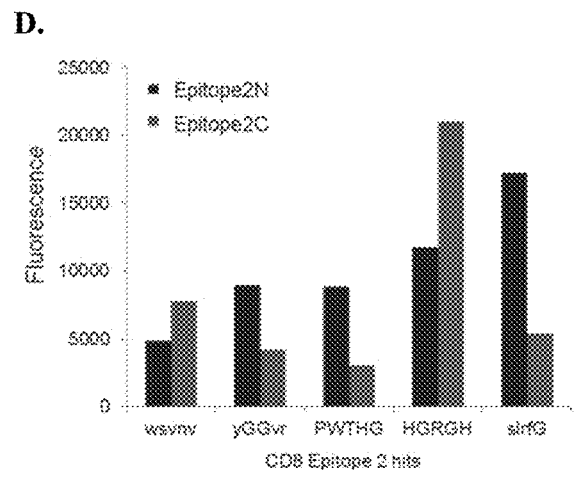

CD8 Epitope2N leads
Cy(PWTHG)
Cy(yGGvr)
Cy(slrfG)

CD8 Epitope1N leads
Cy(AKYRG)
Cy(wplrf)
Cy(ffrly)
Cy(rwfnv)

CD8 Epitope2C leads
Cy(HGRGH)
Cy(wsvnv)

Linker lengths (Å):
PEG$_5$ = 26.4
PEG$_6$ = 30.8

Figure 19
A.
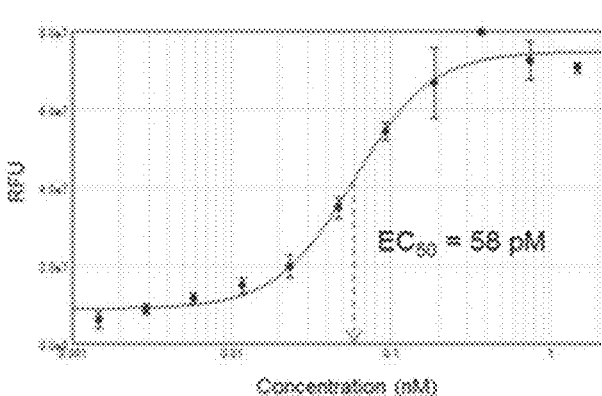
B.
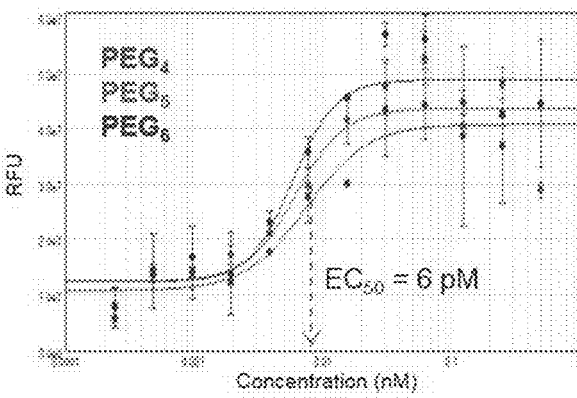

Figure 20
A.
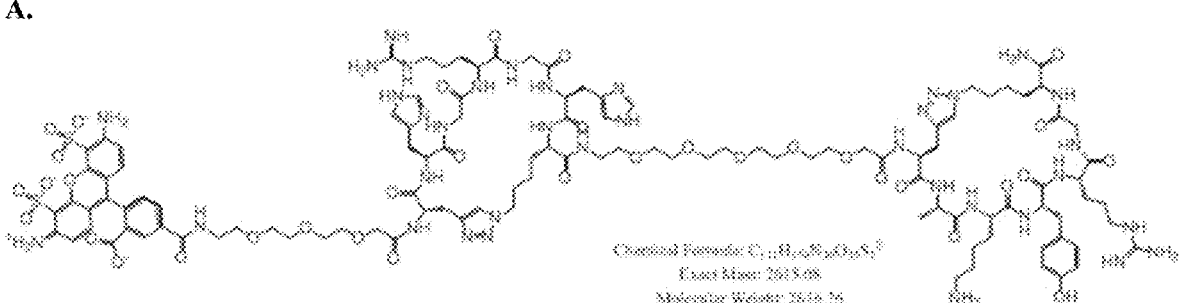
B.
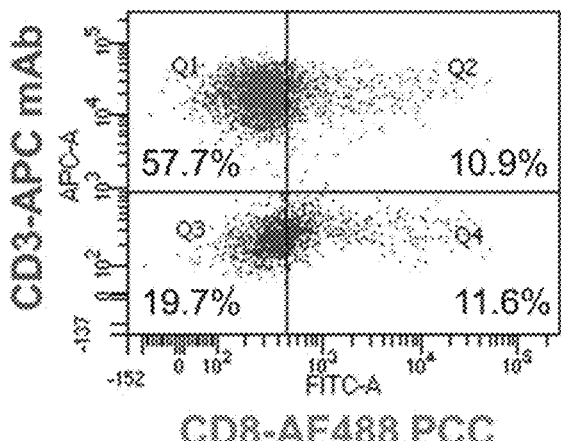
C.
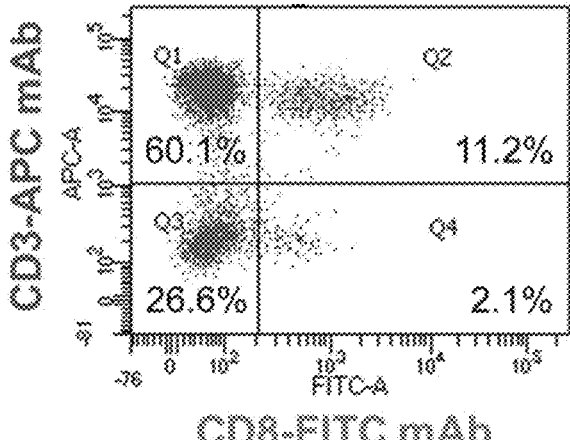

Figure 23
A.
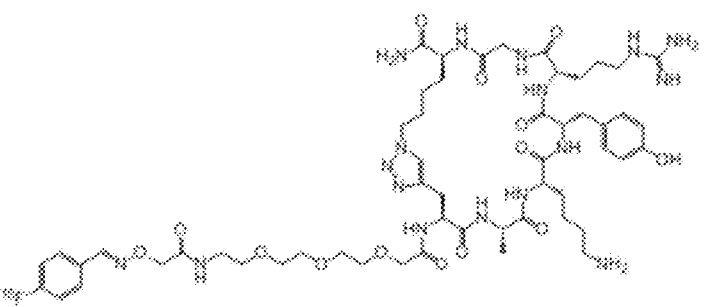
B.
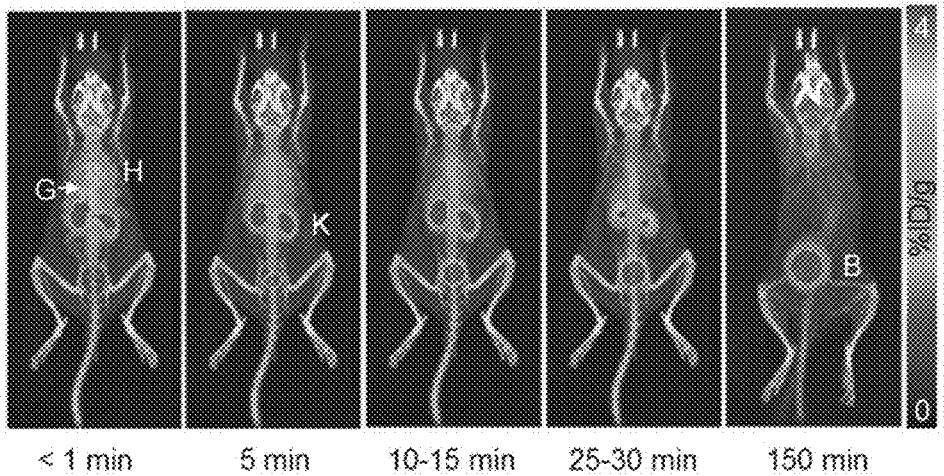
C.
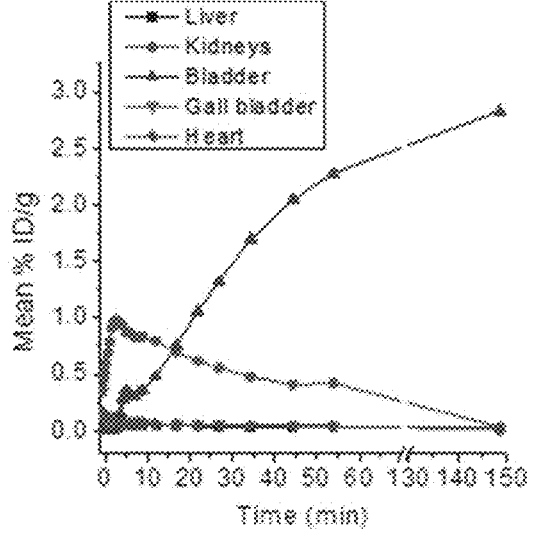

Figure 24
A.
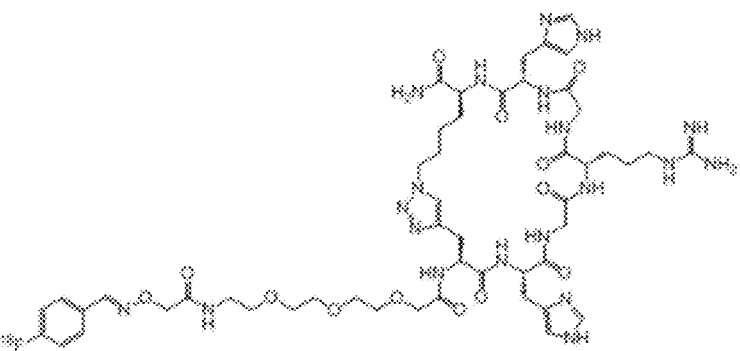
B.
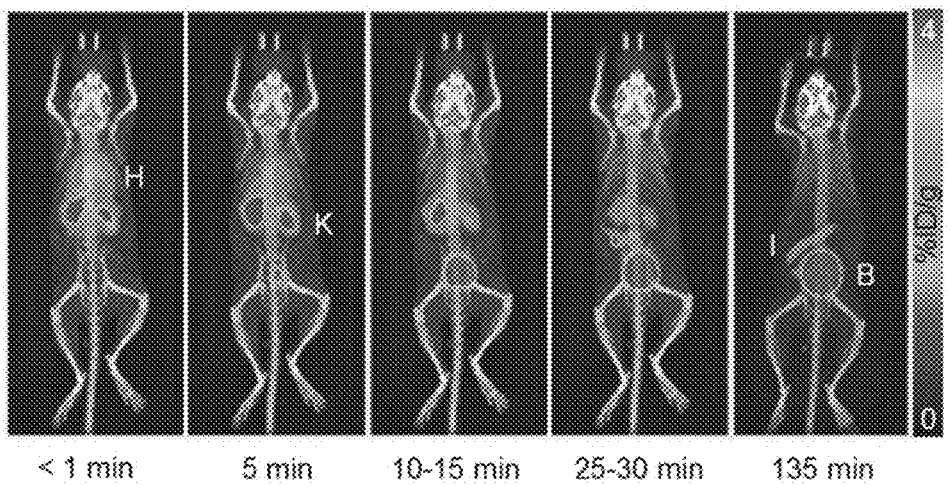
C.
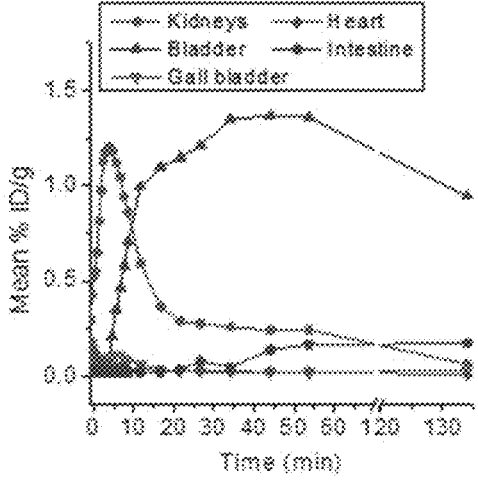

Figure 25
A.
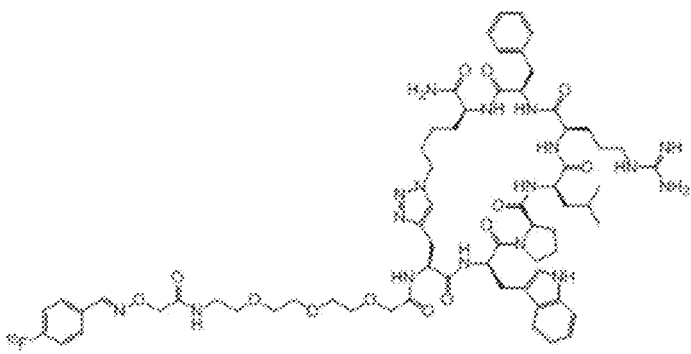
B.
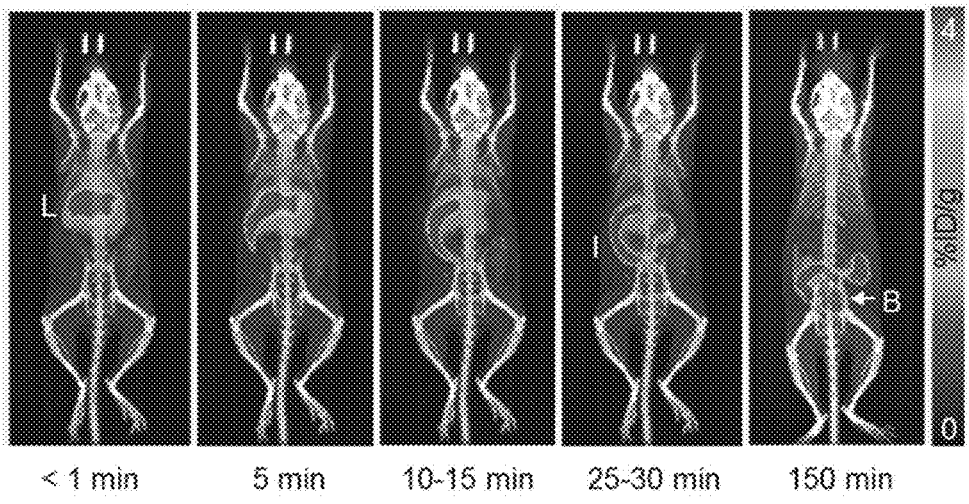
C.
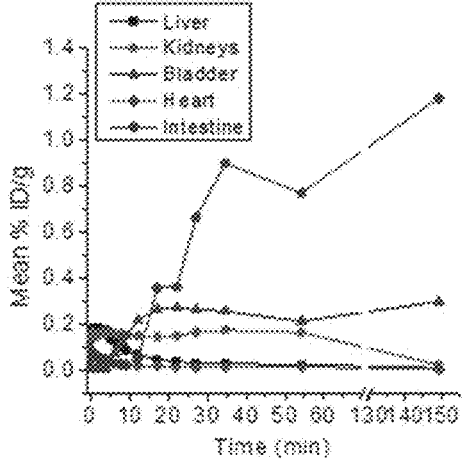

Figure 26
A.
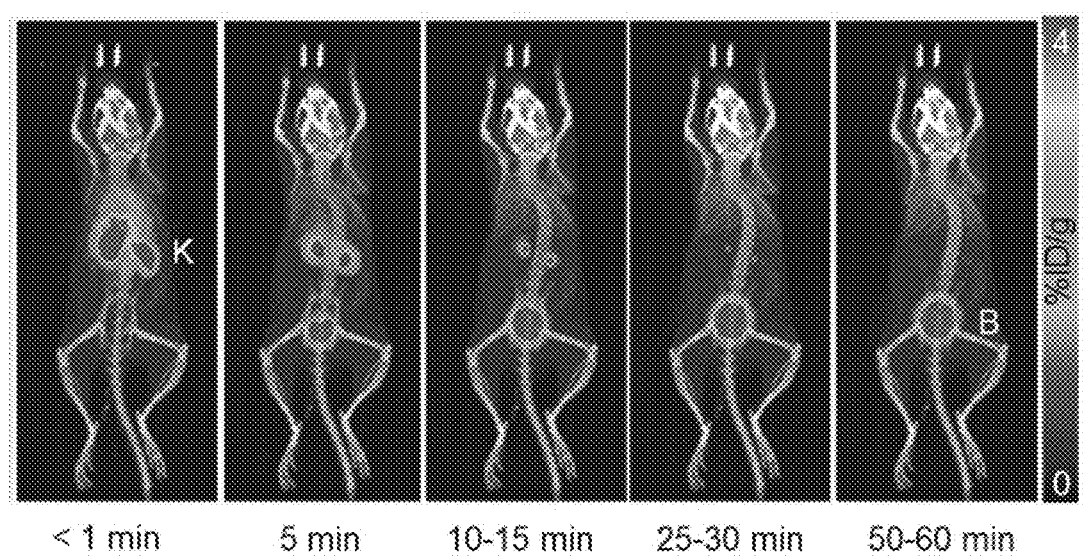
< 1 min     5 min     10-15 min     25-30 min     50-60 min
B.
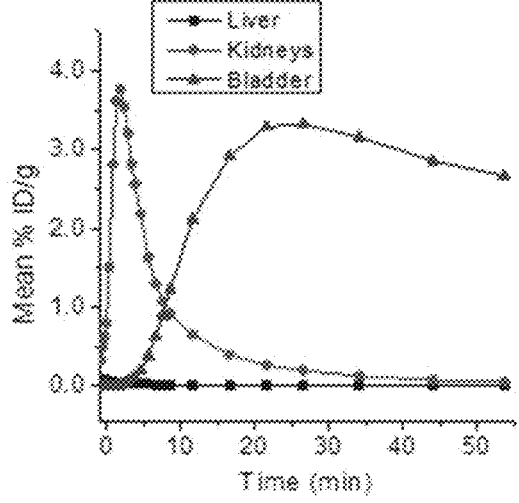

Figure 27
A.
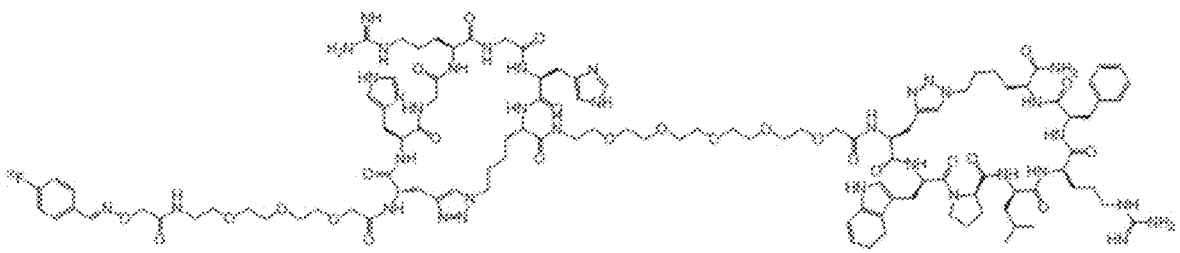
B.
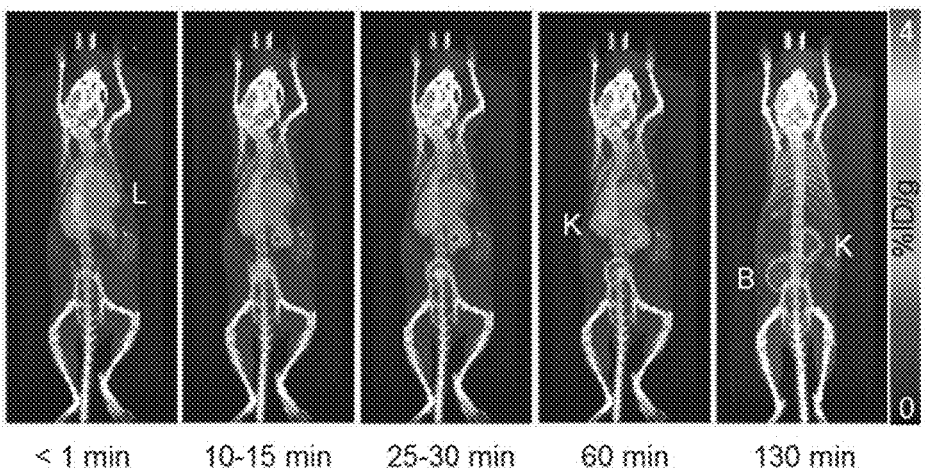
| < 1 min | 10-15 min | 25-30 min | 60 min | 130 min |
C.
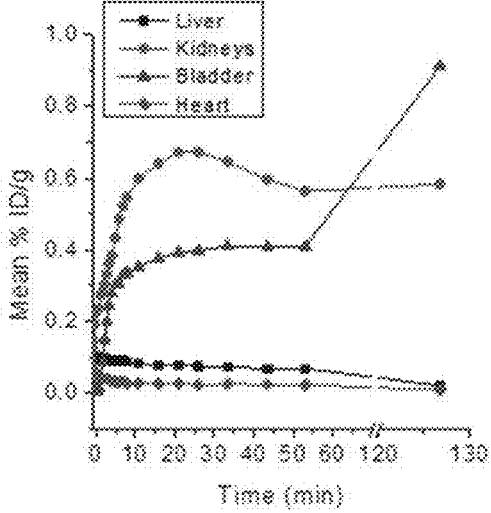

CD8-SPECIFIC CAPTURE AGENTS, COMPOSITIONS, AND METHODS OF USING AND MAKING

RELATED APPLICATIONS

This application claims priority to U.S. Provisional Patent Application No. 62/317,907, filed on Apr. 4, 2016, the content of which is incorporated herein by reference in its entirety.

REFERENCE TO A SEQUENCE LISTING

The instant application contains a Sequence Listing which has been submitted electronically in ASCII format and is hereby incorporated by reference in its entirety. Said ASCII copy, created on Oct. 7, 2025, is named 58607US_CRF_sequencelisting.txt and is 16,434 bytes in size.

BACKGROUND

Human CD8 (cluster of differentiation 8) is a transmembrane glycoprotein that serves as a co-receptor for the T cell receptor (TCR). CD8 binds to the major peptide-histocompatibility complexes (pMHC) on antigen-presenting cells to result in antigen-specific activation of naive or effector CD8+ T cells (Kroger et al. Immunology 2007). CD8+ cytotoxic T lymphocytes (CTLs) are an important part of the immune system because properly activated and non-inhibited CTLs can recognize tumor-associated antigens and kill tumor cells.

Immunotherapy is a type of cancer treatment that harnesses the immune system to combat cancer. For solid tumors, immunotherapy has had the greatest success in easily biopsied cancers such as melanoma and lymphoma. For those patients, pre-existing CD8+ T cells located at the invasive tumor margin were found to be associated with expression of the PD-1/PD-L1 immune inhibitory axis and may predict response to therapy (Tumeh et al. Nature 2014; doi: 10.1038/nature13954). As immunotherapy is extended to additional cancers, the ability to detect CD8+ T cells in vivo has tremendous promise for patient stratification, as well as promise for following therapy responses.

There remains a need for sensitive and selective tools for CD8 detection.

SUMMARY

Accordingly, the present disclosure relates to epitope-targeted macrocyclic peptide ligands and capture agents having an affinity for CD8. The ligands and capture agents are designed to bind to specific synthetic epitopes of CD8 in a manner reminiscent of monoclonal antibodies (mAbs), and were developed by in situ click screening of one-bead-one-compound (OBOC) peptide libraries. In certain embodiments, the ligands and capture agents comprise cyclic peptides. Cyclic peptides have the ability to display protein-like epitopes with restricted conformational flexibility and thus often display enhanced bioavailability, increased stability towards metabolic degradation, and superior binding affinities as compared to their linear counterparts.

In one aspect, provided herein is a stable, synthetic capture agent that specifically binds CD8, wherein the capture agent comprises a first ligand having affinity for a first epitope on CD8, a second ligand having affinity for a second epitope on CD8, and a linker covalently connecting the first ligand to the second ligand.

In another aspect, provided herein is a composition comprising one or more synthetic capture agents, as described herein, that specifically bind CD8.

Epitopes

In an embodiment, the first epitope is 5 to 30 amino acids long. In an embodiment, the first epitope is 8 to 20 amino acids long. In an embodiment, the first epitope is 7 to 13 amino acids long. In an embodiment, the first epitope is at most, 5, 6, 7, 8, 9, 10, 11, 12, 13, 14, 15, 16, 17, 18, 19 or 20 amino acids long. In an embodiment, the first epitope comprises the sequence SQFRVSPLD (SEQ ID NO: 1). In an embodiment, the first epitope comprises the sequence SQFRVSPLDRTWNLGETVELKSQ (SEQ ID NO: 2).

In an embodiment, the second epitope is 5 to 30 amino acids long. In an embodiment, the second epitope is 8 to 20 amino acids long. In an embodiment, the second epitope is 7 to 13 amino acids long. In an embodiment, the second epitope is at most, 5, 6, 7, 8, 9, 10, 11, 12, 13, 14, 15, 16, 17, 18, 19 or 20 amino acids long. In an embodiment, the first or second epitope comprises the sequence FLLYLSQNKP (SEQ ID NO: 3). In an embodiment, the second epitope comprises the sequence AAEGLDTQR (SEQ ID NO: 4). In an embodiment, the first or second epitope comprises the sequence FLLYLSQNKPKAAEGLDTQR (SEQ ID NO: 5).

In an embodiment, the first and second epitopes are located in the CD8a ectodomain.

In certain embodiments, the first and/or second epitopes are synthetic, having at least 90% homology to the corresponding natural epitope of the target protein, and having at least one amino acid comprising an azide or an acetylene group.

In an embodiment, the first ligand binds the first epitope (or a synthetic version thereof) in isolation and the second ligand binds the second epitope (or a synthetic version thereof) in isolation. In the capture agent, the first ligand and the second ligand cooperatively bind the first and second epitopes of CD8, respectively.

Ligands

In an embodiment, the first ligand is 5-9 amino acids in length. In another embodiment, the first ligand is 2-7 amino acids in length. In an embodiment, the first ligand is a linear peptide. In an embodiment, the first ligand is a cyclic peptide. In an embodiment, the first ligand comprises a 1,4-substituted-1,2,3-triazole residue (Tz4) or a 1,5-substituted-1,2,3-triazole residue (Tz5). In a particular embodiment, the triazole residue is a 1,4-substituted-1,2,3-triazole (Tz4) residue. In an embodiment, the first ligand comprises an amino acid sequence 80-100% identical to an amino acid sequence selected from the group consisting of: a) HGSYG (SEQ ID NO: 6); b) KRLGA (SEQ ID NO: 7); c) AKYRG (SEQ ID NO: 8); d) hallw (SEQ ID NO: 9); e) lrGyw (SEQ ID NO: 10); f) vashf (SEQ ID NO: 11); g) nGnvh (SEQ ID NO: 12); h) wplrf (SEQ ID NO: 13); i) rwfnv (SEQ ID NO: 14); j) havwh (SEQ ID NO: 15); k) wvplw (SEQ ID NO: 16); l) ffrly (SEQ ID NO: 17); and m) wyyGf (SEQ ID NO: 18).

In an embodiment, the second ligand is 5-9 amino acids in length. In another embodiment, the second ligand is 2-7 amino acids in length. In an embodiment, the first or second ligand comprises an amino acid sequence 80-100% identical to an amino acid sequence selected from the group consisting of: a) AGDSW (SEQ ID NO: 19); b) HVRHG (SEQ ID NO: 20); c) HGRGH (SEQ ID NO: 21); d) THPTT (SEQ ID NO: 22); e) FAGYH (SEQ ID NO: 23); f) WTEHG (SEQ ID NO: 24); g) PWTHG (SEQ ID NO: 25); h) TNDFD (SEQ ID NO: 26); i) LFPFD (SEQ ID NO: 27); j) slrfG (SEQ ID NO: 28); k) yfrGs (SEQ ID NO: 29); l) wnwvG (SEQ ID NO: 30); m) vaw1G (SEQ ID NO: 31); n) fhvhG (SEQ ID NO: 32); o) wvsnv (SEQ ID NO: 33); p) wsvnv (SEQ ID NO: 34); q) lnshG (SEQ ID NO: 35); r) yGGvr (SEQ ID NO: 36); s) nsvhG (SEQ ID NO: 37); t) ttvhG (SEQ ID NO: 38); u) fdvGh (SEQ ID NO: 39); v) rhGwk (SEQ ID NO: 40); w) Ghtwp (SEQ ID NO: 41); and x) hGrGh (SEQ ID NO: 49). In an embodiment, the second ligand is a linear peptide. In an embodiment, the second ligand is a cyclic peptide. In an embodiment, the second ligand comprises a 1,4-substituted-1,2,3-triazole residue (Tz4) or a 1,5-substituted-1,2,3-triazole residue (Tz5). In a particular embodiment, the triazole residue is a 1,4-substituted-1,2,3-triazole (Tz4) residue.

In an embodiment, the first ligand is selected from Table 3. In an embodiment, the second ligand is selected from Table 6. In an embodiment, the capture agent comprises a first and second ligand selected from the capture agents of Tables 7 and 8.

Linker

In an embodiment, the linker is divalent. In an embodiment, the length of the linker corresponds to the distance between the first epitope and the second epitope. In an embodiment, the length of the linker is about 4.4 Å to about 39.6 Å, about 8.8 Å to about 39.6 Å, about 13.2 Å to about 39.6 Å, about 17.6 Å to about 39.6 Å, about 22 Å to about 39.6 Å, or about 26.4 Å to about 39.6 Å. In a particular embodiment, the length of the linker is about 4.4 Å to about 39.6 Å, about 26.4 Å to about 39.6 Å, or about 28.2 Å. In a more particular embodiment, the length of the linker is about 28.2 Å.

In an embodiment, the linker comprises one or more repeat units of ethylene glycol. In a particular embodiment, the linker comprises $PEG_1$, $PEG_2$, $PEG_3$, $PEG_4$, $PEG_5$, $PEG_6$, $PEG_7$ or $PEG_8$. In a more particular embodiment, the linker comprises $PEG_5$. In an embodiment, the linker comprises an amino acid or a peptide.

Capture Agents

In an embodiment, the capture agent is labeled with a detectable moiety. In a particular embodiment, the detectable moiety is selected from the group consisting of biotin, copper-DOTA, biotin-PEG3, aminooxyacetate, $^{19}FB$, $^{18}FB$ and $FITC-PEG_3$. In another particular embodiment, the detectable moiety is selected from the group consisting of $^{64}Cu$ DOTA, $^{68}Ga$ DOTA, $^{68}Ga$ NOTA, $^{18}F$, $Al^{18}F$ NOTA, $^{64}Cu$, $^{68}Ga$, $^{89}Zr$, $^{124}I$, $^{86}Y$, $^{94m}Tc$, $^{110m}In$, $^{11}C$ and $^{76}Br$.

In an embodiment, the first ligand comprises HGRGH (SEQ ID NO: 21) and second ligand comprises wplrf (SEQ ID NO: 13); or the first ligand comprises HGRGH (SEQ ID NO: 21) and second ligand comprises AKYRG (SEQ ID NO: 8); or the first ligand comprises Ghtwp (SEQ ID NO: 41) and second ligand comprises hGrGh (SEQ ID NO: 49); or the first ligand comprises PWTHG (SEQ ID NO: 25) and second ligand comprises AKYRG (SEQ ID NO: 8).

In an embodiment, the capture agent is selected from Tables 7 and 8. In an embodiment, biligands of Tables 7-8 comprise four families.

```
(1):
HGRGH(SEQ ID NO: 21)-Linker-wplrf(SEQ ID NO: 13),
targeted against Epitope 2C (AAEGLDTQR)
(SEQ ID NO: 4) and Epitope 1N (SQFRVSPLD)
(SEQ ID NO: 1).
```

```
-continued
(2):
HGRGH(SEQ ID NO: 21)-Linker-AKYRG (SEQ ID NO: 8),
targeted against Epitope 2C (AAEGLDTQR)
(SEQ ID NO: 4) and Epitope 1N (SQFRVSPLD)
(SEQ ID NO: 1).

(3):
Ghtwp(SEQ ID NO: 41)-Linker-hGrGh(SEQ ID NO: 49),
targeted against Epitope 2N (FLLYLSQNKP)
(SEQ ID NO: 3) and Epitope 2C (AAEGLDTQR)
(SEQ ID NO: 4).

(4):
PWTHG(SEQ ID NO: 25)-Linker-AKYRG(SEQ ID NO: 8),
targeted against Epitope 2N (FLLYLSQNKP)
(SEQ ID NO: 3) and Epitope 1N (SQFRVSPLD)
(SEQ ID NO: 1).
```

Methods of Use

As used herein, the terms "capture agent of the invention", or "capture agents of the invention" refer to synthetic protein-catalyzed capture agents which bind CD8, as described herein.

Also provided is a method of detecting CD8 in a subject, comprising the step of contacting a biological sample from the subject with one or more capture agents of the invention. Also provided is the use of one or more capture agents of the invention for the detection of CD8 in a subject.

Also provided is a method of detecting CD8 in a biological sample using an immunoassay, wherein the immunoassay utilizes a capture agent as described herein, and wherein said capture agent replaces an antibody or its equivalent in the immunoassay. In certain embodiments, methods are provided for identifying, detecting, quantifying, or separating CD8 in a biological sample using the capture agents as described herein. In one embodiment of the method, the immunoassay is selected from the group of Western blot, pull-down assay, dot blot, and ELISA.

In one aspect, provided herein is a method for detecting CD8 (e.g., CD8+ T cells) in a biological sample, comprising contacting the biological sample with one or more capture agents as described herein.

In an embodiment, the capture agent is labeled with a detectable moiety.

In an embodiment, the method further comprises binding CD8 to said one or more capture agents, and detecting the detectable moiety linked to said one or more capture agents.

Methods of Manufacture

In another aspect, provided herein is a method of producing a synthetic capture agent that specifically binds to a target protein comprising a. selecting a first ligand that binds to a first epitope on the target protein, b. selecting a second ligand that binds to a second epitope on the target protein, c. selecting a linker that has a length that allows the linker to bind both the first ligand and the second ligand when both the first and the second ligands are specifically binding the first and second epitopes, respectively, and d. binding the linker to the first and second ligands, thereby producing the synthetic capture agent that specifically binds to the target protein.

In an embodiment, the first epitope and second epitope are about 4.4 Å to about 39.6 Å, about 8.8 Å to about 39.6 Å, about 13.2 Å to about 39.6 Å, about 17.6 Å to about 39.6 Å, about 22 Å to about 39.6 Å, or about 26.4 Å to about 39.6 Å, or about 28.2 Å distant from each other.

In an embodiment, the linker is 10-50% longer than the distance between the first and second epitopes. In an embodiment, the linker is within 5-25% of the distance between the first and second epitopes. In an embodiment, the linker is within 1-10% of the distance between the first and second epitopes.

In an embodiment of the method, the capture agent has a binding affinity for the target protein greater than either of the ligands. In a particular embodiment, the capture agent has a binding affinity that is at least 50%, at least 75%, or at least 90% of the binding affinity of a full cooperative binder.

In another aspect, provided herein is a method of producing a synthetic capture agent that specifically binds to a target protein comprising a. selecting a first ligand that binds to a first synthetic epitope, wherein the first synthetic epitope is at least 90% homologous to a first epitope of the target protein, and wherein at least one amino acid of the first synthetic epitope comprises an azide or an acetylene group;

b. selecting a second ligand that binds to a second synthetic epitope, wherein the second synthetic epitope is at least 90% homologous to a second epitope of the target protein, and wherein at least one amino acid of the second synthetic epitope comprises an azide or an acetylene group;

c. selecting a linker that has a length that allows the linker to bind both the first ligand and the second ligand when both the first and the second ligands are specifically binding the first and second epitopes, respectively, and d. binding the linker to the first and second ligands, thereby producing the synthetic capture agent that specifically binds to the target protein.

In an embodiment, the target protein is a naturally-occurring protein. In an embodiment, the target protein is CD8.

In an embodiment, the capture agent binds the synthetic epitope and the full length protein with a binding affinity that is at least 50% of the binding affinity of a full cooperative binder. In an embodiment, the capture agent binds the synthetic epitope and the full length protein with a binding affinity that is at least 75% of the binding affinity of a full cooperative binder. In an embodiment, the capture agent binds the synthetic epitope and the full length protein with a binding affinity that is at least 90% of the binding affinity of a full cooperative binder.

In an embodiment, the first epitope and the second epitope comprise the same sequence of the target protein.

Kits

Provided herein in certain embodiments are kits comprising one or more capture agents of the invention. In certain embodiments, these kits may be used for identifying, detecting, quantifying, and/or separating CD8, and in certain embodiments the kits may be used in the diagnosis and/or staging of a condition associated with the presence of CD8. In certain embodiments, a kit as provided herein comprises: (a) a substrate comprising an adsorbent thereon, wherein the adsorbent is suitable for binding CD8, and (b) a washing solution or instructions for making a washing solution, wherein the combination of the adsorbent and the washing solution allows detection of CD8. In other embodiments, the kits provided herein may be used in the treatment of a condition associated with the presence of CD8.

In certain embodiments, a kit may further comprise instructions for suitable operational parameters in the form of a label or a separate insert. For example, the kit may have standard instructions informing a consumer/kit user how to wash the probe after a sample of plasma or other tissue sample is contacted on the probe.

In certain embodiments, a kit comprises (a) one or more capture agents that specifically bind CD8; and (b) a detection reagent. Such kits can be prepared from the materials described herein.

The kits provided herein may optionally comprise a standard or control information, and/or a control amount of material, so that the test sample can be compared with the control information standard and/or control amount to determine if the test amount of CD8 detected in a sample is an amount consistent with a diagnosis of a particular condition.

BRIEF DESCRIPTION OF THE DRAWINGS

FIG. 2 shows a flow diagram for preparing cyclic peptide hits for MALDI-TOF/TOF Sequencing. (1) Triazole-cyclized hit bead of the form $H_2N$-Pra-Cy(XXXXX-click)-Met-TG (SEQ ID NO: 46). (2) Bead after 1st manual Edman degradation step. (3) Bead after 2nd manual Edman degradation step. The resultant linear ATZ-peptide is of a form compatible with MALDI-TOF/TOF sequencing.

FIG. 3 shows the in vitro characterization of macrocycle biotin-$PEG_3$-Cy(wplrf) (SEQ ID NO: 13). (A). Mass spectroscopy analysis. (B). Sandwich ELISA for human CD8a protein against biotin-$PEG_3$-modified Cy(wplrf) (SEQ ID NO: 13) yields $EC_{50}$ value of 16 nM. A similarly assayed biotinylated monoclonal antibody (MA1-19484, Life Technologies) shows similar binding affinity ($EC_{50}$~60 nM). (C). Point ELISAs for human CD8a protein against biotin-$PEG_3$-modified Cy(wplrf) (SEQ ID NO: 13) in 0%, 10%, 50%, and 100% human serum. (D). Point ELISAs for human CD8a protein against biotin-$PEG_3$-modified Cy(wplrf) (SEQ ID NO: 13) before and after treatment with trypsin protease (1 h at 37° C.).

FIG. 4 shows the in vitro characterization of macrocycle biotin-$PEG_3$-Cy(AKYRG) (SEQ ID NO: 8). (A). Mass spectroscopy analysis. (B). Sandwich ELISA for human CD8a protein against biotin-$PEG_3$-modified Cy(AKYRG) (SEQ ID NO: 8) yields $EC_{50}$ value of 11 nM. (C). Point ELISAs for human CD8α protein against biotin-$PEG_3$-modified Cy(AKYRG) in 0%, 10%, 50%, and 100% human serum. (D). Point ELISAs for human CD8α protein against biotin-$PEG_3$-modified Cy(AKYRG) (SEQ ID NO: 8) before and after treatment with trypsin protease (1 h at 37° C.).

FIG. 5 shows the in vitro characterization of macrocycle biotin-$PEG_3$-Cy(rwfnv) (SEQ ID NO: 14). (A). Mass spectroscopy analysis. (B). Sandwich ELISA for human CD8α protein against biotin-$PEG_3$-modified Cy(rwfnv) (SEQ ID NO: 14) yields $EC_{50}$ value of 62 nM. (C). Point ELISAs for human CD8α protein against biotin-$PEG_3$-modified Cy(rwfnv) (SEQ ID NO: 14) in 0%, 10%, 50%, and 100% human serum. (D). Point ELISAs for human CD8α protein against biotin-$PEG_3$-modified Cy(rwfnv) (SEQ ID NO: 14) before and after treatment with trypsin protease (1 h at 37° C.).

FIG. 6 shows the in vitro characterization of macrocycle biotin-$PEG_3$-Cy(ffrly) (SEQ ID NO: 17). (A). Mass spectroscopy analysis. (B). Sandwich ELISA for human CD8α protein against biotin-$PEG_3$-modified Cy(ffrly) (SEQ ID NO: 17) yields $EC_{50}$ value of 56 nM. (C). Point ELISAs for human CD8α protein against biotin-$PEG_3$-modified Cy(ffrly) (SEQ ID NO: 17) in 0%, 10%, 50%, and 100% human serum. (D). Point ELISAs for human CD8α protein against biotin-$PEG_3$-modified Cy(ffrly) (SEQ ID NO: 17) before and after treatment with trypsin protease (1 h at 37° C.).

FIG. 7 shows the in vitro characterization of macrocycle biotin-$PEG_3$-Cy(PWTHG) (SEQ ID NO: 25). (A). Mass spectroscopy analysis. (B). Sandwich ELISA for human CD8α protein against biotin-$PEG_3$-modified Cy(PWTHG) (SEQ ID NO: 25) yields $EC_{50}$ value of 8 nM. (C). Point ELISAs for human CD8α protein against biotin-$PEG_3$-modified Cy(PWTHG) (SEQ ID NO: 25) in 0%, 10%, 50%, and 100% human serum. (D). Point ELISAs for human CD8α protein against biotin-$PEG_3$-modified Cy(PWTHG) (SEQ ID NO: 25) before and after treatment with trypsin protease (1 h at 37° C.).

FIG. 8 shows the in vitro characterization of macrocycle biotin-$PEG_3$-Cy(yGGvr) (SEQ ID NO: 36). (A). Mass spectroscopy analysis. (B). Sandwich ELISA for human CD8α protein against biotin-$PEG_3$-modified Cy(yGGvr) (SEQ ID NO: 36) yields $EC_{50}$ value of 10 nM. (C). Point ELISAs for human CD8α protein against biotin-$PEG_3$-modified Cy(yGGvr) (SEQ ID NO: 36) in 0%, 10%, 50%, and 100% human serum. (D). Point ELISAs for human CD8α protein against biotin-$PEG_3$-modified Cy(yGGvr) (SEQ ID NO: 36) before and after treatment with trypsin protease (1 h at 37° C.).

FIG. 9 shows the in vitro characterization of macrocycle biotin-$PEG_3$-Cy(slrfG) (SEQ ID NO: 28). (A). Mass spectroscopy analysis. (B). Sandwich ELISA for human CD8α protein against biotin-$PEG_3$-modified Cy(slrfG) (SEQ ID NO: 28) yields $EC_{50}$ value of 20 nM. (C). Point ELISAs for human CD8α protein against biotin-$PEG_3$-modified Cy(slrfG) (SEQ ID NO: 28) in 0%, 10%, 50%, and 100% human serum. (D). Point ELISAs for human CD8α protein against biotin-$PEG_3$-modified Cy(slrfG) (SEQ ID NO: 28) before and after treatment with trypsin protease (1 h at 37° C.).

FIG. 10 shows the in vitro characterization of macrocycle biotin-$PEG_3$-Cy(HGRGH) (SEQ ID NO: 21). (A). Mass spectroscopy analysis. (B). Sandwich ELISA for human CD8α protein against biotin-$PEG_3$-modified Cy(HGRGH) (SEQ ID NO: 21) yields $EC_{50}$ value of 6 nM. (C). Point ELISAs for human CD8α protein against biotin-$PEG_3$-modified Cy(HGRGH) (SEQ ID NO: 21) in 0%, 10%, 50%, and 100% human serum.

FIG. 11 shows the in vitro characterization of macrocycle biotin-$PEG_3$-Cy(wsvnv) (SEQ ID NO: 34). (A). Mass spectroscopy analysis. (B). Sandwich ELISA for human CD8α protein against biotin-$PEG_3$-modified Cy(wsvnv) (SEQ ID NO: 34) yields $EC_{50}$ value of 9 nM. (C). Point ELISAs for human CD8α protein against biotin-$PEG_3$-modified Cy(wsvnv) in 0%, 10%, 50%, and 100% human serum. (D). Point ELISAs for human CD8α protein against biotin-$PEG_3$-modified Cy(wsvnv) (SEQ ID NO: 34) before and after treatment with trypsin protease (1 h at 37° C.).

FIG. 12 shows the orientation of macrocycle binding to CD8 Epitopes 1 and 2. (A). His-tagged CD8 Epitope1 was synthesized to contain polyglycine substitution of the sequences either N-terminal (SEQ ID NO: 50) or C-terminal (SEQ ID NO: 51) to the location of the click handle (R10). (B). Similarly, His-tagged CD8 Epitope2 was synthesized to contain polyglycine substitution either N-terminal (SEQ ID NO: 52) or C-terminal to (SEQ ID NO: 53) K58. Glycine residues are shown in italics. (C). Point ELISAs for the His-tagged CD8 epitopes against the macrocyclic peptide ligands demonstrate preferential binding to specific regions within each epitope.

FIG. 15 shows the general structures of cooperative biligand candidates with PEG linkers ranging from 8.8 to 39.6 Å to join the two macrocycles. (A). Biotin-$PEG_3$-Cy (Epi2C PCC)-$PEG_1$-Cy(Epi1N PCC) ($PEG_1$=8.8 Å). (B). Biotin-$PEG_3$-Cy(Epi2C PCC)-$PEG_2$-Cy(Epi1N PCC) ($PEG_2$=13.2 Å). (C). Biotin-$PEG_3$-Cy(Epi2C PCC)-$PEG_3$-Cy(Epi1N PCC) ($PEG_3$=17.6 Å). (D). Biotin-$PEG_3$-Cy (Epi2C PCC)-$PEG_4$-Cy(Epi1N PCC) ($PEG_4$=22 Å). (E). Biotin-$PEG_3$-Cy(Epi2C PCC)-$PEG_5$-Cy(Epi1N PCC) ($PEG_5$=26.4 Å). (F). Biotin-$PEG_3$-Cy(Epi2C PCC)-$PEG_8$-Cy(Epi1N PCC) ($PEG_8$=39.6 Å). The amino acid side chains in macrocycles Epi2C PCC and Epi1N PCC are shown as $R_1$-$R_5$ and $R_6$-$R_{10}$, respectively.

FIG. 18 shows additional PCC biligands that specifically bind CD8 that exploit cooperativity. Biligands of the form Biotin-$PEG_3$-Cy(HGRGH) (SEQ ID NO: 21)-$PEG_x$-Cy (AKYRG) (SEQ ID NO: 8) (x=5 to 6) were tested in a CD8 ELISA. Biligand $EC_{50}$ values of 25 pM against CD8 were obtained, showing that both $PEG_5$ and $PEG_6$ effectively bridge the 28.2 Å distance between the CD8 Epitope2C and CD8 Epitope1N. This represents a >200-fold improvement in affinity relative to the individual PCC macrocyclic ligands.

FIG. 19 shows the binding assays of biligands illustrating cooperativity. (A). Biligand Cy(Ghtwp) (SEQ ID NO: 41)-Lys (Biotin)-PEG$_1$-Cy(hGrGh) (SEQ ID NO: 49) exhibits an EC$_{50}$ value of 58 pM against CD8. (B). Biotin-PEG$_3$-Cy (PWTHG) (SEQ ID NO: 25)-PEG$_x$-Cy(AKYRG) (SEQ ID NO: 8) (x=4 to 6) biligands exhibit EC$_{50}$ values of 6 pM against CD8.

FIG. 20 shows the cellular binding assay of a biligand. (A). Chemical structure of Alexa Fluor 488-labeled biligand Cy(HGRGH) (SEQ ID NO: 21)-PEG$_5$-Cy(AKYRG) (SEQ ID NO: 8). (B). Flow cytometry of human PBMCs stained with CD3-APC mAb (a pan T cell marker) and Alexa Fluor 488-labeled Cy(HGRGH) (SEQ ID NO: 21)-PEG$_5$-Cy (AKYRG) (SEQ ID NO: 8). The cell populations in Q2 and Q4 are CD8$^+$ as detected by the biligand. (C). Flow cytometry of human PBMCs stained with CD3-APC mAb and CD8-FITC mAb (clone: RPA-T8) as a control. AF488=Alexa Fluor 488. APC=allophycocyanin. FITC=fluorescein isothiocyanate.

FIG. 22 shows $^{18}$F-labeling of aminooxy-derivatized PCCs (macrocycle anchors and biligands) with [$^{18}$F]FB.

FIG. 23 shows the biodistribution of CD8 macrocycle anchor in normal mice. (A) Chemical structure of [$^{18}$F]FB-labeled anchor Cy(AKYRG) (SEQ ID NO: 8). (B) [$^{18}$F]FB-labeled Cy(AKYRG) (SEQ ID NO: 8) small-animal PET/CT scans of C57BL/6 mice over time. Coronal MIP images are representative of biodistribution observed in 5 mice scanned. % ID/g=percentage injected dose per gram of tissue; H=heart; G=gall bladder; K=kidney; B=bladder. (C) PET measurements, average percentage of total injected dose in organs over time. MIP=maximum intensity projection.

FIG. 24 shows the biodistribution of CD8 macrocycle anchor in normal mice. (A) Chemical structure of [$^{18}$F]FB-labeled anchor Cy(HGRGH) (SEQ ID NO: 21). (B) [$^{18}$F] FB-labeled Cy(HGRGH) (SEQ ID NO: 21) small-animal PET/CT scans of C57BL/6 mice over time. Coronal MIP images are representative of biodistribution observed in 5 mice scanned. % ID/g=percentage injected dose per gram of tissue; H=heart; K=kidney; I=intestine; B=bladder. (C) PET measurements, average percentage of total injected dose in organs over time. MIP=maximum intensity projection.

FIG. 25 shows the biodistribution of CD8 macrocycle anchor in normal mice. (A) Chemical structure of [$^{18}$F]FB-labeled anchor Cy(wplrf) (SEQ ID NO: 13). (B) [$^{18}$F]FB-labeled Cy(wplrf) (SEQ ID NO: 13) small-animal PET/CT scans of C57BL/6 mice over time. Coronal MIP images are representative of biodistribution observed in 5 mice scanned. % ID/g=percentage injected dose per gram of tissue; L=liver; I=intestine; B=bladder. (C) PET measurements, average percentage of total injected dose in organs over time. MIP=maximum intensity projection.

FIG. 26 shows the biodistribution of [$^{18}$F]FB in normal mice. (A) [$^{18}$F]FB small-animal PET/CT scans of C57BL/6 mice over time. Coronal MIP images are representative of biodistribution observed in 2 mice scanned. % ID/g=percentage injected dose per gram of tissue; K=kidney; B=bladder. (B) PET measurements, average percentage of total injected dose in organs over time. MIP=maximum intensity projection.

FIG. 27 shows the biodistribution of CD8 biligand in normal mice. (A) Chemical structure of [$^{18}$F]FB-labeled biligand Cy(HGRGH) (SEQ ID NO: 21)-PEG$_5$-Cy(wplrf) (SEQ ID NO: 13). (B) [$^{18}$F]FB-labeled Cy(HGRGH) (SEQ ID NO: 21)-PEG$_5$-Cy(wplrf) (SEQ ID NO: 13) small-animal PET/CT scans of C57BL/6 mice over time. Coronal MIP images are representative of biodistribution observed in 2 mice scanned. % ID/g=percentage injected dose per gram of tissue; L=liver; K=kidney; B=bladder. (C) PET measurements, average percentage of total injected dose in organs over time. MIP=maximum intensity projection.

DETAILED DESCRIPTION

Figure 1:
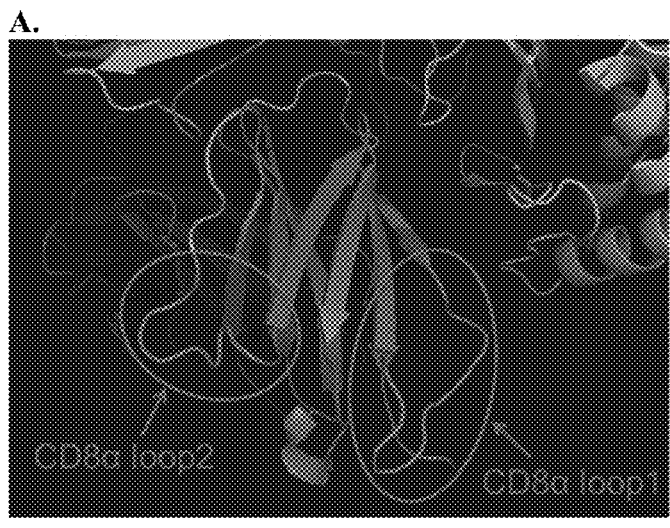
FIG. 1 shows epitopes derived from the CD8 protein. (A). Crystal structure of the human CD8αα-pMHC complex (PDB ID: 1AKJ) with epitopes circled. One CD8a monomer is shown in the center, while the other is shown faintly to the left. HLA-A2/peptide (pMHC) is shown in the upper left and in the upper right corner. (B). Sequences of the designed CD8a epitopes: loop 1, SEQ ID NO: 2 and loop 2, SEQ ID NO: 5. An azide handle (Az4) is substituted at the bracketed amino acid positions.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The present disclosure is meant to encompass all pharmaceutically acceptable disclosed capture agents being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$O, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled disclosed capture agents, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled capture agents can generally be prepared by conventional techniques known to those skilled in the art or by processes analogous to those described in the Preparations and Examples as set out below using an appropriate isotopically-labeled reagent in place of the non-labeled reagent previously employed.

The present disclosure is also meant to encompass the in vivo metabolic products of the disclosed capture agents. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

The term "capture agent" as used herein refers to a composition that comprises two or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules. In some aspects a capture agent is a protein catalyzed capture agent (PCC).

Reference to "capture agents" further refers to pharmaceutically acceptable salts thereof. "Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

The capture agents described herein, or their pharmaceutically acceptable salts may contain one or more asymmetric centers and may thus give rise to enantiomers, diastereomers, and other stereoisomeric forms that may be defined, in terms of absolute stereochemistry, as (R) or(S) or, as (D) or (L) for amino acids. The present invention is meant to include all such possible isomers, as well as their racemic and optically pure forms. Optically active (+) and ( ) (R) and(S), or (D) and (L) isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G".

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The term "epitope" as used herein refers to a distinct molecular surface of a protein (e.g., CD8). Typically, the epitope is a polypeptide and it can act on its own as a finite sequence of 10-40 amino acids.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to capture agent binding to an epitope on a predetermined antigen. Typically, the capture agent binds with an affinity (KD)) of approximately less than $10^{-7}$ M, such as approximately less than $10^{-8}$ M, $10^{-9}$ M or $10^{-10}$ M or even lower.

The term "KD)" as used herein refers to the dissociation equilibrium constant of a particular capture agent-antigen interaction. Typically, the capture agents of the invention bind to CD8 with a dissociation equilibrium constant (KD)) of less than approximately $10^{-6}$ M, $10^{-7}$ M, such as less than approximately $10^{-8}$ M, $10^{-9}$ M or $10^{-10}$ M or even lower, for example, as determined using surface plasmon resonance (SPR) technology in a Biacore instrument using the antigen as the ligand and the capture agent as the analyte, and binds to the predetermined antigen with an affinity corresponding to a KD that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the capture agent, so that when the $K_D$ of the capture agent is very low (that is, the capture agent is highly specific), then the amount with which the affinity for the antigen is lower than the affinity for a non-specific antigen may be at least 10,000 fold.

The term "$k_d$" ($sec^{-1}$) as used herein refers to the dissociation rate constant of a particular capture agent-antigen interaction. Said value is also referred to as the $k_{off}$ value.

The term "$k_a$" ($M^{-1} \times sec^{-1}$) as used herein refers to the association rate constant of a particular capture agent-antigen interaction.

The term "$K_D$" (M) as used herein refers to the dissociation equilibrium constant of a particular capture agent-antigen interaction.

The term "$K_A$" ($M^{-1}$) as used herein refers to the association equilibrium constant of a particular capture agent-antigen interaction and is obtained by dividing the $k_a$ by the $k_d$.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a disclosed capture agent may vary according to factors such as the disease state, age, sex, and weight of the individual, and the ability of the capture agent to elicit a desired response in the individual.

The term "stable" as used herein with regard to a capture agent protein catalyzed capture agent or pharmaceutical formulation thereof refers to the agent or formulation retaining structural and functional integrity for a sufficient period of time to be utilized in the methods described herein.

The term "synthetic" as used herein with regard to a protein catalyzed capture agent or capture agent refers to the capture agent has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

In certain embodiments, the term "CD8" as used herein refers to human CD8. In some embodiments, CD8 comprises one of the following amino acid sequence or an amino acid sequence substantially identical to it.

```
Sequence of the ectodomain for human CD8a:
                                 (SEQ ID NO: 44)
SGCSWLFQPR GAAASPTFLL SQFRVSPLDR TWNLGETVEL

KCQVLLSNPT YLSQNKPKAA EGLDTQRFSG KRLGDTFVLT

LSDFRRENEG YYFCSALSNS IMYFSHFVPV FLPAKPTTTP

APRPPTPAPT IASQPLSLRP EACRPAAGGA VHTRGLDFAC

D

Sequence of the ectodomain for mouse CD8a:
                                 (SEQ ID NO: 45)
KPQAPELRIF PKKMDAELGQ KVDLVCEVLG SVSQGCSWLF

QNSSSKLPQP TFVVYMASSH NKITWDEKLN SSKLFSAMRD

TNNKYVLTLN KFSKENEGYY FCSVISNSVM YFSSVVPVLQ

KVNSTTTKPV LRTPSPVHPT GTSQPQRPED CRPRGSVKGT

GLDFACDIY
```

Development of CD8 Capture Agents

Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a capture agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The protein effectively plays the role of an extremely selective variant of the Cu (I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (see: USSN 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand may be identified by screening the protein against a large (>106 element) one-bead-one-compound (OBOC) peptide library, where the peptides may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described, most require detailed structural information on the target to guide the screening strategy, and most (such as the original in situ click approach), are optimized for low-diversity small molecule libraries.

The present embodiment further generalizes the in situ click application to naively find an anchor ligand using in situ click. In previous approaches, a known binder was necessary to begin the ligand. This method provides a mechanism to find an anchor ligand de novo.

As described herein, an iterative in situ click chemistry approach was utilized to synthesize biligand capture agents that specifically bind CD8. This in situ click chemistry approach comprised two steps. First, two "anchor" ligands were found that bound CD8 at distinct but relatively close sites. Second, a linker of an appropriate size was found that bound the two ligands producing a capture agent with higher affinity for CD8.

The capture agents generated by the methods disclosed herein were found to display binding affinity for CD8. The capture agents were shown to function as both capture and detection agents in ELISA assays and efficiently immunoprecipitate CD8.

CD8 Capture Agents

In one aspect, provided herein is a stable, synthetic capture agent that specifically binds CD8, wherein the capture agent comprises two or more "anchor" ligands (also referred to as simply "ligands" herein) and a linker and wherein the ligands selectively bind CD8.

In certain embodiments, a ligand comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azidoalkyl, substituted and unsubstituted polyethyleneglycolyl, and substituted and unsubstituted 1,2,3-triazole.

In certain embodiments, the ligands are linked to one another via a covalent linkage through a linker. In certain of these embodiments, the ligand and linker are linked to one another via an amide bond or a 1,4-disubstituted-1,2,3-triazole linkage as shown below:

1,4-disubstituted-1,2,3-triazole Linkage

In those embodiments where the ligands and linker are linked to one another via a 1,4-disubstituted-1,2,3-triazole linkage, the 1,4-disubstituted-1,2,3-triazole linkage may be formed by Cu-Catalyzed Azide/Alkyne Cycloaddition (CuAAC).

In certain embodiments, the ligands and linker are linked to one another by a Tz4 linkage having the following structure:

In certain embodiments, the ligands and linker are linked to one another by a Tz5 linkage having the following structure:

In those embodiments wherein one or more of the ligands and linker are linked to one another via amide bonds, the amide bond may be formed by coupling a carboxylic acid group and an amine group in the presence of a coupling agent (e.g., 0-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In certain embodiments, the capture agents provided herein are stable across a range of reaction conditions and/or storage times. A capture agent that is "stable" as used herein maintains the ability to specifically bind to a target protein. In certain embodiments, the capture agents provided herein are more stable than an antibody binding to the same target protein under one or more reaction and/or storage conditions. For example, in certain embodiments the capture agents provided herein are more resistant to proteolytic degradation than an antibody binding to the same target protein.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than an antibody binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than an antibody binding to the same target protein, and/or remain stable at a specific temperature for a longer time period than an antibody binding to the same target protein.

In certain embodiments, the capture agents provided herein are stable at a pH range from about 3.0 to about 8.0. In certain embodiments, the range is about 4.0 to about 7.0. In certain embodiments, the range is about 7.0 to about 8.0.

In certain embodiments, the capture agents provided herein are stable in human serum for more than 12 hours. In certain of these embodiments, the capture agents are stable in human serum for more than 18 hours, more than 24 hours, more than 36 hours, or more than 48 hours. In certain embodiments, the capture agents provided herein are stable for a longer period of time in human serum than an antibody binding to the same target protein. In certain embodiments, the capture agents are stable as a powder for two months at a temperature of about 60° C.

In certain embodiments, the capture agents provided herein may comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C, $^{76}$Br, $^{123}$I, $^{131}$I, $^{67}$Ga, $^{111}$In and $^{99m}$Tc, or other radiolabeled products that may include gamma emitters, proton emitters, positron emitters, tritium, or covered tags detectable by other methods (i.e., gadolinium) among others. In a particular embodiment, the detection label is $^{18}$F. In certain embodiments, the capture agents may be modified to be used as imaging agents. The imaging agents may be used as diagnostic agents.

In certain embodiments, the capture agents provided herein may be modified to obtain a desired chemical or biological activity. Examples of desired chemical or biological activities include, without limitation, improved solubility, stability, bioavailability, detectability, or reactivity.

Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Properties

In certain embodiments, the CD8 capture agents provided herein are stable across a wide range of temperatures, pH values, storage times, storage conditions, and reaction conditions, and in certain embodiments the capture agents are more stable than a comparable antibody or biologic. In certain embodiments, the capture agents are stable in storage as a lyophilized powder. In certain embodiment, the capture agents are stable in storage at a temperature of about −80° C. to about 60° C. In certain embodiments, the capture agents are stable at room temperature. In certain embodiments, the capture agents are stable in human serum for at least 24 hours. In certain embodiments, the capture agents are stable at a pH in the range of about 3 to about 12. In certain embodiments, the capture agents are stable as a powder for two months at a temperature of about 60° C.

Methods of Making/Screening Capture Agents

Provided herein in certain embodiments are methods of screening target-binding moieties and/or making capture agents that comprise these target-binding moieties. Methods for screening target-binding moieties and/or making capture agents that comprise these target-binding moieties can also be found in International Publication Nos. WO 2012/106671, WO 2013/033561, WO 2013/009869 and WO 2014/074907, each of which is incorporated by reference, herein, in their entireties.

In certain embodiments, two separately-identified ligands that bind to two different regions of the same protein (the target) are chemically linked together to form a biligand. By optimizing a linker of the two ligands, the biligand formed by the ligands and linker can exhibit a binding affinity that is far superior to either of the individual ligands. This enhanced binding effect is called binding cooperativity. For an ideal cooperative binder, the thermodynamic binding energies of the individual ligands to the target will sum to yield the binding energy of the linked biligand. This means that the binding affinity constant ($K_D$) of the linked biligand will be the product of the binding affinity of the individual ligands (i.e. $K_D = K_{D1} \times K_{D2}$, where the subscripts 1 and 2 refer to the two ligands). In practice, full cooperative binding is rarely, if ever, achieved. Thus, a comparison of the properties of a linked biligand against those of a fully cooperative binder provides a measurement of how optimally the two ligands were linked.

If the protein target has a known and well-defined tertiary (folded) structure, then key aspects of this targeting method involve strategies for identifying ligands that bind to preferred regions of the protein, followed by approaches for identifying an optimized linker. If the protein does not have a well-defined tertiary structure, the disclosure describes strategies designed to still achieve a significant measure of cooperative binding from a biligand.

Figure 28:
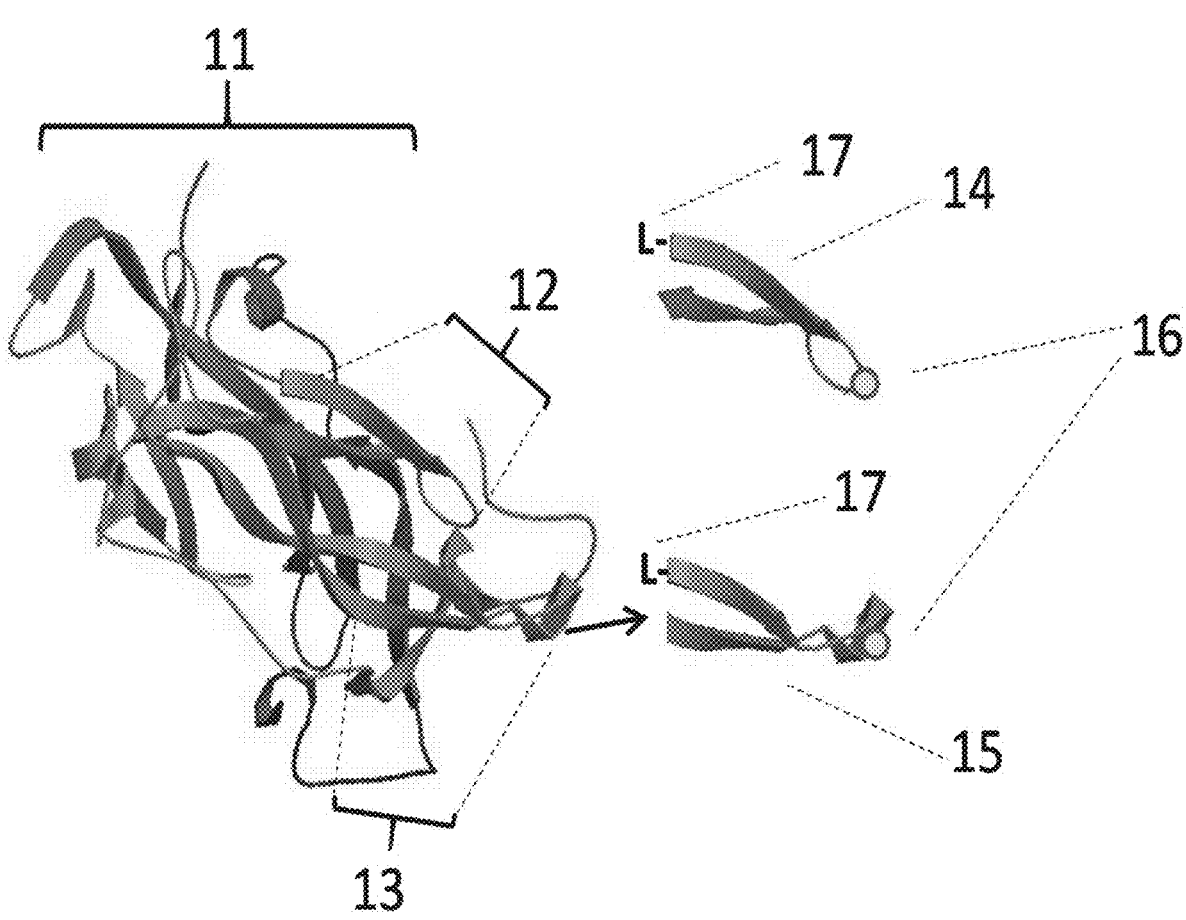
FIG. 28 shows the starting point for developing a set of PCC binders against a protein target.

FIG. 28 describes the starting point for developing a set of PCC binders against a protein target (11). The initial goal is to identify one or more PCCs that bind to one epitope on the protein target (12), and one or more different PCCs binding to a second epitope (13). Additional PCCs that bind to a third, fourth, etc., epitope may be useful as well. The epitope targeted PCC method teaches that this may be accomplished by screening peptide libraries against synthetic epitopes (SynEps) such as those shown in FIG. 28 (14,15). A SynEp is a polypeptide that has the sequence of the naturally occurring target epitope, except that one position contains an artificial amino acid that presents an azide or acetylene chemical group (16), called a click handle. The SynEp is further modified to contain an assay handle, such as a biotin group, at the N- or C-terminus (17). The screening procedure can be done using any procedure disclosed herein or known in the art. By screening, one identifies at least one unique peptide binder to each of at least two epitopes on the target. Those peptide binders are validated via carrying out binding assays against the full protein target (11) as well as against the SynEps. For those binding assays, the SynEps are prepared with the naturally occurring residue in place of the click handle (16).

Figure 29:
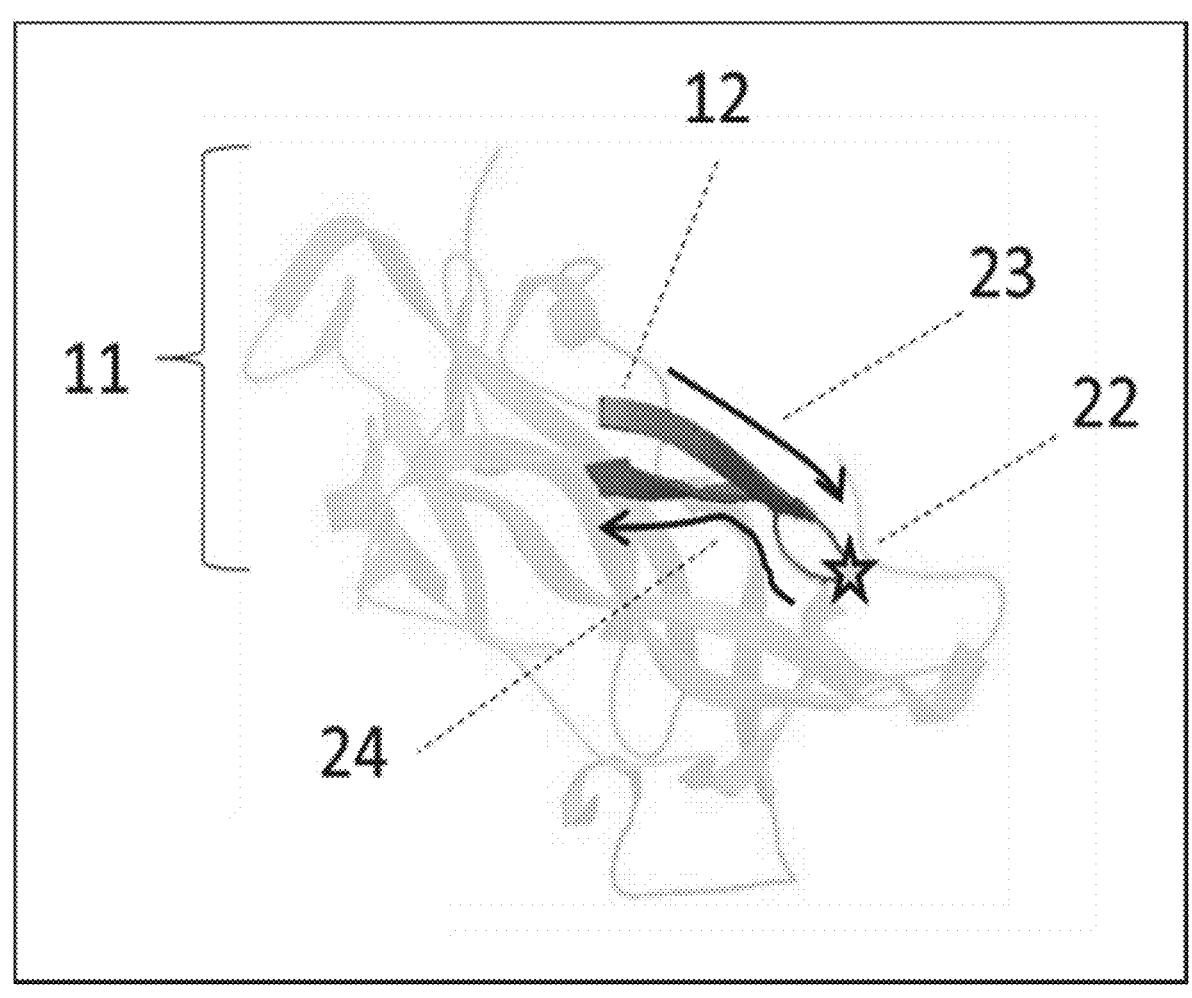
FIG. 29 shows a PCC that binds to two different sites.

Ideally, the different regions of the target protein to which the different ligands bind will be relatively close together (a few nanometers or less) in the tertiary protein structure. For even a single SynEp, a screen can produce PCCs that bind to two different sites. In FIG. 29, the region representing the epitope of interest (12) is highlighted against a dimmer background of the full protein (11). The amino acid residue that was substituted for a click handle in the SynEp structure is indicated by a star (22). During the SynEp screening steps, PCCs that bind to the N-terminal side of the epitope (23) or the C-terminal side (24) may both be identified.

Once the epitope targeted PCCs are identified, there are several methods for selecting a linker.

Figure 30:
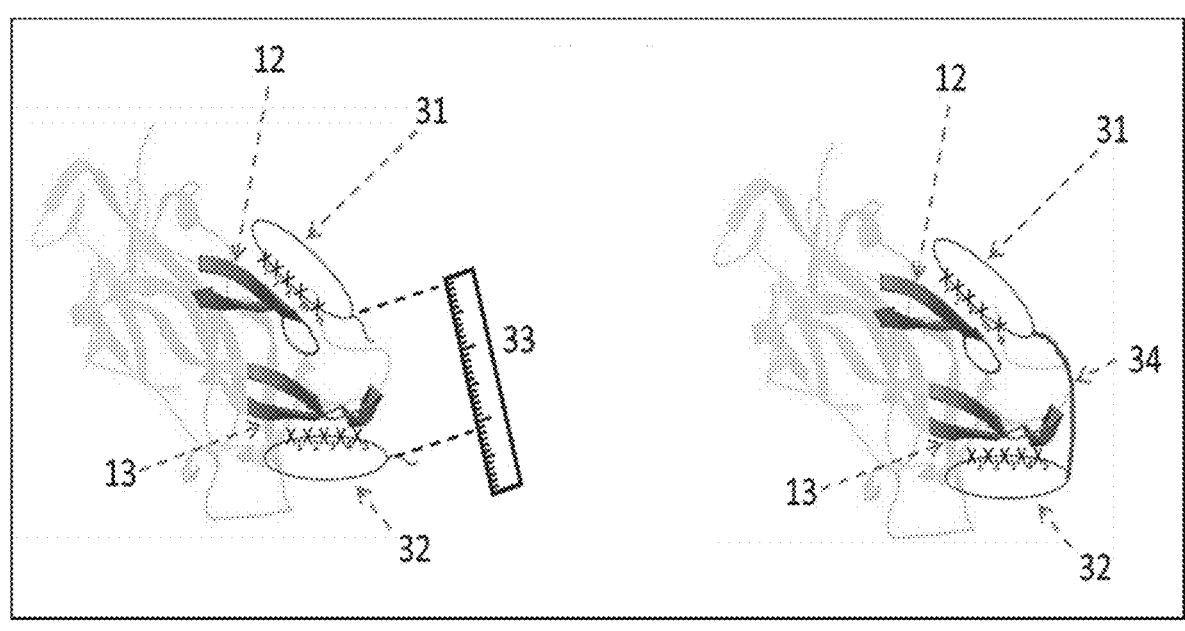
FIG. 30 shows the estimation of optimal linker length.

In a first embodiment, if the folded structure of the protein is known, and if the PCCs bind to that folded structure, then one can use that information, plus knowledge of which PCCs bind to which epitopes, to estimate an optimal linker length. This is illustrated in FIG. 30. This figure shows one PCC (31) that binds to the N-side of one epitope (12) and a second PCC (32) binding to the C-side of a second epitope (13). Analysis of this binding arrangement, together with the structure of the protein from, for example, the Protein Database, permits an estimate of the length of an optimized linker (33). Such an estimate can narrow down the choice of candidate linkers to a very small number. One example might be to use such a length estimate to select one or two length-matched polyethylene glycol oligomers for testing. The best linker (34) is the one that brings the biligand affinity closest to that a fully cooperative binder.

In a second embodiment, if the folded structure of the protein is not known, or if the protein simply does not have a well-defined folded structure, then one uses as much information as is available to determine the composition of a library of candidate linker molecules. That library is then screened to identify a best linker.

In a third embodiment, if the folded structure of the protein is not known or if the protein simply does not have a well-defined folded structure, then, using what knowledge about the protein does exist, simply select a linker to append the two PCCs. Even if an optimized, fully cooperative binder is not identified in this way, the linked biligand will almost certainly outperform either of the two monoligands because of cooperativity effects.

In Vitro

For detection of CD8 in solution, a capture agent as described herein can be detectably labeled, then contacted with the solution, and thereafter formation of a complex between the capture agent and the CD8 target can be detected. As an example, a fluorescently labeled capture agent can be used for in vitro CD8 detection assays, wherein the capture agent is added to a solution to be tested for CD8 under conditions allowing binding to occur. The complex between the fluorescently labeled capture agent and the CD8 target can be detected and quantified by, for example, measuring the increased fluorescence polarization arising from the complex-bound peptide relative to that of the free peptide.

Alternatively, a sandwich-type "ELISA" assay can be used, wherein a capture agent is immobilized on a solid support such as a plastic tube or well, then the solution suspected of containing CD8 is contacted with the immobilized binding moiety, non-binding materials are washed away, and complexed polypeptide is detected using a suitable detection reagent for recognizing CD8.

For detection or purification of soluble CD8 from a solution, capture agents of the invention can be immobilized on a solid substrate such as a chromatographic support or other matrix material, then the immobilized binder can be loaded or contacted with the solution under conditions suitable for formation of a capture agent/CD8 complex. The non-binding portion of the solution can be removed and the complex can be detected, for example, using an anti-CD8 antibody, or an anti-binding polypeptide antibody, or the CD8 can be released from the binding moiety at appropriate elution conditions.

In Vivo Diagnostic Imaging

A particularly preferred use for the capture agents of the invention is for creating visually readable images of CD8 or CD8-expressing cells in a biological fluid, such as, for example, in human serum. The CD8 capture agents disclosed herein can be converted to imaging reagents by conjugating the capture agents with a label appropriate for diagnostic detection. Preferably, a capture agent exhibiting much greater specificity for CD8 than for other serum proteins is conjugated or linked to a label appropriate for the detection methodology to be employed. For example, the capture agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In another embodiment, rather than directly labeling a capture agent with a detectable label or radiotherapeutic construct, one or more peptides or constructs of the invention can be conjugated with for example, avidin, biotin, or an antibody or antibody fragment that will bind the detectable label or radiotherapeutic.

A. Magnetic Resonance Imaging

The CD8 capture agents described herein can advantageously be conjugated with a paramagnetic metal chelate in order to form a contrast agent for use in MRI.

Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, Gd3+, is particularly preferred for MRI contrast agents, due to its high relaxivity and low toxicity, with the further advantage that it exists in only one biologically accessible oxidation state, which minimizes undesired metabolysis of the metal by a patient. Another useful metal is Cr3+, which is relatively inexpensive. Gd (III) chelates have been used for clinical and radiologic MR applications since 1988, and approximately 30% of MRI exams currently employ a gadolinium-based contrast agent.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxy-ethylidene groups, or carboxymethylene groups. Examples of chelators include, but are not limited to, diethylenetri-aminepentaacetic acid (DTPA), 1,4,7,10-tetraazacyclo-tetra-decane-1,4,7,10-tetraacetic acid (DOTA), 1-substituted 1,4, 7,-tricarboxymethyl-1,4,7,10-teraazacyclododecane (DO3A), ethylenediaminetetraacetic acid (EDTA), and 1,4, 8,11-tetra-azacyclotetradecane-1,4,8, 11-tetraacetic acid (TETA). Additional chelating ligands are ethylene bis-(2-hydroxy-phenylglycine) (EHPG), and derivatives thereof, including 5-CI-EHPG, 5-Br-EHPG, 5-Me-EHPG, 5-t-B u-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (0 and/or N), which macrocyclic compounds can consist of one ring, or two or three rings joined together at the hetero ring elements, e.g., benzo-DOTA, dibenzo-DOTA, and benzo-NOTA, where NOTA is 1,4, 7-triazacyclononane N,N',N"-triacetic acid, benzo-TETA, benzo-DOTMA, where DOTMA is 1,4,7,10-tet-raazacyclotetradecane-1,4,7,10-tetra(methyl tetraacetic acid), and benzo-TETMA, where TETMA is 1,4,8, 11-tet-raazacyclotetradecane-1,4,8,11-(methyl tetraacetic acid); derivatives of 1,3-propylene-diaminetetraacetic acid (PDTA) and triethylenetetraaminehexaacetic acid (TTNA); derivatives of 1,5,10-N,N',N"-tris (2,3-dihydroxybenzoy 1)-tricatecholate (LICAM); and 1,3,5-N,N',N"-tris (2,3-di-hydroxybenzoyl) aminomethylbenzene (MECAM). A preferred chelator for use in the present invention is DTPA, and the use of DO3A is particularly preferred. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143, 274, all of which are hereby incorporated by reference.

In accordance with the present disclosure, the chelator of the MRI contrast agent is coupled to the CD8 capture agent. The positioning of the chelate should be selected so as not to interfere with the binding affinity or specificity of the CD8 capture agent. The chelate also can be attached anywhere on the capture agent.

In general, the CD8 capture agent can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the CD8 binding moiety); derivatized or underivatized polyethylene glycols (PEGs), polyoxyethyl-ene, or polyvinylpyridine chains; substituted or unsubsti-tuted polyamide chains; derivatized or underivatized polyamine, polyester, polyethylenimine, polyacrylate, poly (vinyl alcohol), polyglycerol, or oligosaccharide (e.g., dex-tran) chains; alternating block copolymers; malonic, suc-cinic, glutaric, adipic and pimelic acids; caproic acid; simple diamines and dialcohols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and the CD8 capture agent using such linkers (WO 95/28967, WO 98/18496, WO 98/18497 and discus-sion therein). The CD8 binding moiety can be linked through an N- or C-terminus via an amide bond, for example, to a metal coordinating backbone nitrogen of a metal chelate or to an acetate arm of the metal chelate itself. The present disclosure contemplates linking of the chelate on any position, provided the metal chelate retains the ability to bind the metal tightly in order to minimize toxicity.

MRI contrast reagents prepared according to the disclo-sures herein can be used in the same manner as conventional MRI contrast reagents. Certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. Magn. Reson. Med., 40:298-310) and flow-spoiled gradient echo sequences (Edelman, R. et al., 1990. Radiology, 177: 45-50). These methods also include flow independent tech-niques that enhance the difference in contrast, such as inversion-recovery prepared or saturation-recovery prepared sequences that will increase the contrast between CD8-expressing tissue and background tissues. Finally, magneti-zation transfer preparations also can improve contrast with these agents (Goodrich, K. et al., 1996. Invest. Radia, 31:323-32).

The labeled reagent is administered to the patient in the form of an injectable composition. The method of admin-istering the MRI contrast agent is preferably parenterally, meaning intravenously, intraarterially, intrathecally, intersti-tially, or intracavitarilly. For imaging CD8-expressing tis-sues, such as tumors, intravenous or intraarterial adminis-tration is preferred. For MRI, it is contemplated that the subject will receive a dosage of contrast agent sufficient to enhance the MR signal at the site CD8 expression by at least 10%. After injection with the CD8 capture agent containing MRI reagent, the patient is scanned in the MRI machine to determine the location of any sites of CD8 expression. In therapeutic settings, upon identification of a site of CD8 expression (e.g., fluid or tissue), an anti-cancer agent (e.g., inhibitors of CD8) can be immediately administered, if necessary, and the patient can be subsequently scanned to visualize viral load.

B. Nuclear Imaging (Radionuclide Imaging) and Radiotherapy

The CD8 capture agents of the invention can be conjugated with a radionuclide reporter appropriate for scintigraphy, SPECT, or PET imaging and/or with a radionuclide appropriate for radiotherapy. Constructs in which the CD8 capture agents are conjugated with both a chelator for a radionuclide useful for diagnostic imaging and a chelator useful for radiotherapy are within the scope of the invention.

For use as a PET agent a disclosed capture agent may be complexed with one of the various positron emitting metal ions, such as is $^{51}Mn$, $^{52}Fe$, $^{60}Cu$, $^{68}Ga$, $^{72}As$, $^{94m}Tc$, or $^{110}In$. The binding moieties of the invention can also be labeled by halogenation using radionuclides such as $^{18}F$, $^{124}I$, $^{125}I$, $^{131}I$, $^{123}I$, $^{77}Br$, and $^{76}Br$. Preferred metal radionuclides for scintigraphy or radiotherapy include $^{99m}Tc$, $^{51}Cr$, $^{67}Ga$, $^{68}Ga$, $^{47}Sc$, $^{51}Cr$, $^{167}Tm$, $^{141}Ce$, $^{111}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $^{161}Tb$, $^{177}Lu$, $^{198}Au$ and $^{199}Au$. The choice of metal will be determined based on the desired therapeutic or diagnostic application. For example, for diagnostic purposes the preferred radionuclides include $^{64}Cu$, $^{67}Ga$, $^{68}Ga$, $^{99m}Tc$, and $^{111}In$. For therapeutic purposes, the preferred radionuclides include $^{64}Cu$, $^{90}Y$, $^{105}Rh$, $^{111}In$, $^{117m}Sn$, $^{149}Pm$, $^{153}Sm$, $^{161}Tb$, $^{166}Tb$, $^{166}Dy$, $^{166}Ho$, $^{175}Yb$, $^{177}Ln$, $^{186/188}Re$ and $^{199}Au$. $^{99m}Tc$ is useful for diagnostic applications because of its low cost, availability, imaging properties, and high specific activity. The nuclear and radioactive properties of $^{99m}Tc$ make this isotope an ideal scintigraphic imaging agent. This isotope has a single photon energy of 140 keV and a radioactive half-life of about 6 hours, and is readily available from a $^{99}Mo$-$^{99m}Tc$ generator. $^{18}F$, 4-[$^{18}F$]fluorobenzaldehyde ($^{18}Fb$, A1[$^{18}F$]-NOTA, $^{68}Ga$-DOTA, and $^{68}Ga$-NOTA are typical radionuclides for conjugation to CD8 capture agents for diagnostic imaging.

The metal radionuclides may be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, DO3A, TETA, NOTA and bisamino bisthiol (BAT) chelators (see also U.S. Pat. No. 5,720,934). For example, N.sub.4 chelators are described in U.S. Pat. Nos. 6,143,274; 6,093,382; 5,608,110; 5,665,329; 5,656, 254; and 5,688,487. Certain N.sub.35 chelators are described in PCT/CA94/00395, PCT/CA94/00479, PCT/CA95/00249 and in U.S. Pat. Nos. 5,662,885; 5,976,495; and 5,780,006. The chelator also can include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in, for example, Liu, S, and Edwards, D., 1999. Chem. Rev., 99:2235-2268, and references therein.

The chelator also can include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

The chelators can be covalently linked directly to the CD8 capture agent via a linker, as described previously, and then directly labeled with the radioactive metal of choice (see, WO 98/52618, U.S. Pat. Nos. 5,879,658, and 5,849,261).

CD8 capture agents comprising $^{18}F$, 4-[$^{18}F$]fluorobenzaldehyde ($^{18}FB$), A1[$^{18}F$]-NOTA, $^{68}Ga$-DOTA, and $^{68}Ga$-NOTA are of preferred interest for diagnostic imaging. Complexes of radioactive technetium are also useful for diagnostic imaging, and complexes of radioactive rhenium are particularly useful for radiotherapy. In forming a complex of radioactive technetium with the reagents of this invention, the technetium complex, preferably a salt of $^{99m}Tc$ pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with $^{99m}Tc$. Alternatively, the complex can be formed by reacting a peptide of this invention conjugated with an appropriate chelator with a pre-formed labile complex of technetium and another compound known as a transfer ligand. This process is known as ligand exchange and is well known to those skilled in the art. The labile complex can be formed using such transfer ligands as tartrate, citrate, gluconate or mannitol, for example. Among the $^{99m}Tc$ pertechnetate salts useful with the present invention are included the alkali metal salts such as the sodium salt, or ammonium salts or lower alkyl ammonium salts.

Preparation of the complexes of the present invention where the metal is radioactive rhenium can be accomplished using rhenium starting materials in the +5 or +7 oxidation state. Examples of compounds in which rhenium is in the Re (VII) state are $NH_4ReO_4$ or $KReO_4$. Re(V) is available as, for example, [$ReOCl_4$]($NBu_4$), [$ReOCl_4$]($AsPh_4$), $ReOCl_3$ ($PPh_3$)$_2$ and as $ReO_2$(pyridine)$^{4+}$, where Ph is phenyl and Bu is n-butyl. Other rhenium reagents capable of forming a rhenium complex also can be used.

Radioactively labeled PET, SPECT, or scintigraphic imaging agents provided by the present invention are encompassed having a suitable amount of radioactivity. Generally, the unit dose to be administered has a radioactivity of about 0.01 mCi to about 100 mCi, preferably 1 mCi to 20 mCi. The solution to be injected at unit dosage is from about 0.01 mL to about 10 mL. It is generally preferred to form radioactive complexes in solutions containing radioactivity at concentrations of from about 0.01 mCi to 100 mCi per mL.

Typical doses of a radionuclide-labeled CD8 capture agent according to the invention provide 10-20 mCi. After injection of the radionuclide-labeled CD8 capture agents into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the radiotherapeutic compounds of the present invention are known to those skilled in the art. The compounds can be administered using many methods including, but not limited to, a single or multiple IV or IP injections, using a quantity of radioactivity that is sufficient to cause damage or ablation of the targeted CD8-expressing tissue, but not so much that substantive damage is caused to non-target (normal tissue). The quantity and dose required is different for different constructs, depending on the energy and half-life of the isotope used, the degree of uptake and clearance of the agent from the body and the mass of the CD8-expressing tissue. In general, doses can range from a single dose of about 30-50 mCi to a cumulative dose of up to about 3 Ci.

The radiotherapeutic compositions of the invention can include physiologically acceptable buffers, and can require radiation stabilizers to prevent radiolytic damage to the compound prior to injection. Radiation stabilizers are known to those skilled in the art, and can include, for example, para-aminobenzoic acid, ascorbic acid, gentistic acid and the like.

A single, or multi-vial kit that contains all of the components needed to prepare the complexes of this invention, other than the radionuclide, is an integral part of this invention.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend on the nature of the exchange complex to be formed. The proper conditions are well known to those that are skilled in the art. It is preferred that the kit contents be in lyophilized form. Such a single vial kit can optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or .alpha., .beta., or .gamma. cyclodextrin that serve to improve the radiochemical purity and stability of the final product. The kit also can contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial can contain all of the ingredients that are required to form a labile Tc (V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. can be present in either or both vials.

Also provided herein is a method to incorporate an $^{18}$F radiolabeled prosthetic group onto an CD8 capture agent. In one embodiment, 4-[$^{18}$F]fluorobenzaldehyde ($^{18}$FB) is conjugated onto a capture agent bearing an aminooxy moiety, resulting in oxime formation. In another embodiment, [$^{18}$F] fluorobenzaldehyde is conjugated onto a capture agent bearing an acyl hydrazide moiety, resulting in a hydrazone adduct. 4-Fluorobenzaldehyde, can be prepared in $^{18}$F form by displacement of a leaving group, using $^{18}$F ion, by known methods.

$^{18}$F-labeled capture agents can also be prepared from capture agents possessing thiosemicarbazide moieties under conditions that promote formation of a thiosemicarbozone, or by use of a $^{18}$F-labeled aldehyde bisulfite addition complex.

The above methods are particularly amenable to the labeling of capture agents, e.g., the capture agents described herein, which can be modified during synthesis to contain a nucleophilic hydroxylamine, thiosemicarbazide or hydrazine (or acyl hydrazide) moiety that can be used to react with the labeled aldehyde. The methods can be used for any capture agent that can accommodate a suitable nucleophilic moiety. Typically the nucleophilic moiety is appended to the N-terminus of the peptide, but the skilled artisan will recognize that the nucleophile also can be linked to an amino acid side chain or to the peptide C-terminus. Methods of synthesizing a radiolabeled peptide sequence are provided in which 4-[$^{18}$F]fluorobenzaldehyde is reacted with a peptide sequence comprising either a hydroxylamine, a thiosemicarbazide or a hydrazine (or acyl hydrazide) group, thereby forming the corresponding oximes, thiosemicarbazones or hydrazones, respectively. The 4-[$^{18}$F]fluorobenzaldehyde typically is generated in situ by the acid-catalyzed decomposition of the addition complex of 4-[$^{18}$F]fluorobenzaldehyde and sodium bisulfite. The use of the bisulfite addition complex enhances the speed of purification since, unlike the aldehyde, the complex can be concentrated to dryness. Formation of the complex is also reversible under acidic and basic conditions. In particular, when the complex is contacted with a peptide containing a hydroxylamine, a thiosemicarbazide or a hydrazine (or acyl hydrazide) group in acidic medium, the reactive free 4-[$^{18}$F]fluorobenzaldehyde is consumed as it is formed in situ, resulting in the corresponding $^{18}$F radiolabeled peptide sequence.

In the instances when the oxime, thiosemicarbazone or hydrazone linkages present in vivo instability, an additional reduction step may be employed to reduce the double bond connecting the peptide to the $^{18}$F bearing substrate. The corresponding reduced peptide linkage would enhance the stability. One of skill in the art would appreciate the variety of methods available to carry out such a reduction step. Reductive amination steps as described in Wilson et al., Journal of Labeled Compounds and Radiopharmaceuticals, XXVIII (10), 1189-1199, 1990 may also be used to form a Schiff's base involving a peptide and 4-[$^{18}$F]fluorobenzaldehyde and directly reducing the Schiffs base using reducing agents such as sodium cyanoborohydride.

The 4-[$^{18}$F]fluorobenzaldehyde may be prepared as described in Wilson et al., Journal of Labeled Compounds and Radiopharmaceuticals, XXVIII (10), 1189-1199, 1990; Iwata et al., Applied radiation and isotopes, 52, 87-92, 2000; Poethko et al., The Journal of Nuclear Medicine, 45, 892-902, 2004; and Schottelius et al., Clinical Cancer Research, 10, 3593-3606, 2004. The Na$^{18}$F in water may be added to a mixture of Kryptofix and K$_2$CO$_3$. Anhydrous acetonitrile may be added and the solution is evaporated in a heating block under a stream of argon. Additional portions of acetonitrile may be added and evaporated to completely dry the sample. The 4-trimethylammoniumbenzaldehyde triflate may be dissolved in DMSO and added to the dried F-18. The solution may then be heated in the heating block. The solution may be cooled briefly, diluted with water and filtered through a Waters®. Oasis HLB LP extraction cartridge. The cartridge may be washed with 9:1 water: acetonitrile and water to remove unbound $^{18}$F and unreacted 4-trimethylammoniumbenzaldehyde triflate. The 4-[$^{18}$F] fluorobenzaldehyde may then be eluted from the cartridge with methanol in fractions.

Therapeutic Applications

Provided herein in certain embodiments are methods of using the CD8 capture agents disclosed herein to identify, detect, quantify, and/or separate CD8 in a biological sample. In certain embodiments, these methods utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues.

Provided herein in certain embodiments are methods of using the CD8 capture agents disclosed herein to diagnose and/or classify (e.g., stage) a condition associated with CD8 expression. In certain of these embodiments, the methods comprise (a) obtaining a biological sample from a subject; (b) measuring the presence or absence of CD8 in the sample with the CD8 capture agent; (c) comparing the levels of CD8 to a predetermined control range for CD8; and (d) diagnosing a condition associated with CD8 expression based on the difference between CD8 levels in the biological sample and the predetermined control.

In other embodiments, the CD8 capture agents disclosed herein are used as a mutant specific targeted therapeutic. In certain aspects of this embodiment, the CD8 capture agent is administered alone without delivering DNA, a radiopharmaceutical or another active agent.

The CD8 capture agents described herein also can be used to target genetic material to CD8 expressing cells. The genetic material can include nucleic acids, such as RNA or DNA, of either natural or synthetic origin, including recombinant RNA and DNA and antisense RNA and DNA. Types of genetic material that can be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material can be combined, for example, with lipids, proteins or other polymers. Delivery vehicles for genetic material can include, for example, a virus particle, a retroviral or other gene therapy vector, a liposome, a complex of lipids (especially cationic lipids) and genetic material, a complex of dextran derivatives and genetic material, etc.

In an embodiment the capture agents of the invention are utilized in gene therapy. In this embodiment, genetic material, or one or more delivery vehicles containing genetic material can be conjugated to one or more CD8 capture agents of this disclosure and administered to a patient.

Therapeutic agents and the CD8 capture agents disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and CD8 binding polypeptide can be coexpressed from the same synthetic gene, created using recombinant DNA techniques, as described above. The coding sequence for the CD8 binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the CD8 binding polypeptide. A particular advantage of this general approach is that concatamerization of multiple, tandemly arranged CD8 capture agents is possible, thereby increasing the number and concentration of CD8 binding sites associated with each therapeutic protein. In this manner, CD8 binding avidity is increased, which would be expected to improve the efficacy of the recombinant therapeutic fusion protein.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1: CD8 Epitope Design

CD8 was expressed on the T-cell surface as either a aa homodimer or $\alpha\beta$ heterodimer. The CD8 monomer consisted of four discrete functional domains: (1) extracellular Ig-like ectodomain, (2) membrane proximal stalk (hinge) region, (3) transmembrane domain, and (4) cytoplasmic domain. Based upon publicly available protein structure data, CD8$\alpha$ was examined since this monomer is common to both CD8$\alpha\alpha$ and CD8$\alpha\beta$ and thus the developed PCC agents would detect a broad range of CD8 T cell subsets.

Using the crystal structure of the human CD8$\alpha\alpha$-pMHC complex (PDB ID: 1AKJ), epitopes were identified in the extracellular Ig-like ectodomain of CD8$\alpha$ that would be good candidates for Synthetic Epitope Targeting. Two unstructured loops were identified in the CD8$\alpha$ ectodomain that are adjacent in tertiary structure by <28.2 Å (FIG. 1A). These loops were deemed suitable epitopes for PCC agent development based on the following criteria:

Epitope is a continuous sequence (8 to 30 amino acids);

Epitope occurs in a region of the protein that is exposed and accessible when the protein is folded into its native conformation;

Epitopes are separated by short distances.

The sequences of CD8$\alpha$ loop1 and CD8$\alpha$ loop2 are shown in FIG. 1B.

Each epitope was synthesized to include an azide handle (Az4=L-azidolysine) at a selected internal amino acid location. For CD8$\alpha$ loop1, the R10Az4 substitution was made because (a) arginine and Az4 are chemically similar, (b) the side chain of this amino acid points outward and does not interact with other atoms in the protein, and (c) it is located in the middle of the exposed loop of interest. For CD8$\alpha$ loop2, the K58Az4 substitution was made based on similar considerations. The location of substituted azide handle (Az4) in each designed CD8$\alpha$ epitope is shown in FIG. 1B.

Example 2: Screening a Macrocycle Library Against CD8 Epitopes 1 and 2

Screens were performed using a triazole-cyclized OBOC library of the form H2N-Pra-Cy(XXXXX-click)-Met-TG (SEQ ID NO: 46), where TG=TentaGel® S NH$_2$ resin (S 30 902, Rapp Polymere), X=one of sixteen L-amino acids (lacking Cys, Met, Ile, and Gln), and Pra=L-propargylglycine. Macrocycles were identified against the two CD8 epitope fragments using a four-step screening process: 1) a pre-clear to eliminate non-specific binders, 2) a product screen to identify hits resulting from CD8 Epitope1-templated in situ click chemistry, 3) another product screen to identify hits resulting from CD8 Epitope2-templated in situ click chemistry, and 4) a target screen against His-tagged CD8$\alpha$ human recombinant protein to identify peptides that bind to the protein as well as the epitopes.

Pre-clear. Swelled library beads (400 mg) were blocked overnight with Blocking Buffer (25 mM Tris-HCl, 150 mM NaCl, 1% (w/v) BSA, and 0.05% (v/v) Tween-20, pH 7.6) at 4° C., then washed with Blocking Buffer three times. A 1:10,000 dilution of Streptavidin-Alkaline Phosphatase (V559C, Promega) in 5 mL Blocking Buffer was added to the beads and incubated with gentle shaking at room temperature for 1 h. The beads were subsequently washed with 3×3 mL TBS (25 mM Tris-HCl, 150 mM NaCl, pH 7.6) (1 min ea), 3×3 mL 0.1 M glycine pH 2.8 wash buffer, 3×3 mL TBS, then 3×3 mL Alkaline Phosphatase buffer (100 mM Tris-HCl, 150 mM NaCl, 1 mM MgCl$_2$, pH 9) (5 min ea). Binding was visualized by incubating the beads in the presence of 5-bromo-4-chloro-3-indolyl phosphate/nitro blue tetrazolium (BCIP/NBT) substrate (S3771, Promega) for 25 min. Purple beads indicated background binders and were removed by pipet and discarded. The remaining clear beads were collected and stripped with 7.5 M guanidine hydrochloride pH 2.0 for 30 min, washed ten times with water, and incubated in 1-methyl-2-pyrrolidinone (NMP) overnight to decolorize.

Product Screen with CD8 Epitope 1. Beads remaining from the pre-clear were washed with water ten times and TBS three times. Beads were then incubated with 3 mL of 100 µM CD8 Epitope1 fragment (Biotin-PEG$_3$-SQFRVSPLD[Az4]TWNLGETVELKSQ) (SEQ ID NO: 2) in TBS for 3 h at room temperature to allow for an in situ click reaction to occur. The beads were washed with TBS ten times and then incubated with 7.5 M guanidine hydrochloride pH 2.0 for 1 h to remove all CD8 epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of CD8 epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet. These 24 hits and separately the non-hits were treated with 7.5 M guanidine hydrochloride pH 2.0 for 30 min to remove attached streptavidin, washed ten times with water, and incubated in NMP overnight to decolorize.

Product Screen with CD8 Epitope 2. The 24 hits and separately the non-hit beads obtained from the product screen were washed with water ten times and TBS three times. The non-hit beads were then incubated with 3 mL of 100 µM CD8 Epitope2 fragment (Biotin-PEG$_3$-FLLY-LSQNKP[Az4]AAEGLDTQR) (SEQ ID NO: 5) in TBS for 3 h at room temperature to allow for an in situ click reaction to occur. The beads were washed with TBS ten times and then incubated with 7.5 M guanidine hydrochloride pH 2.0 for 1 h to remove all CD8 epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of CD8 epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet. These 45 hits were treated with 7.5 M guanidine hydrochloride pH 2.0 for 30 min to remove attached streptavidin, washed ten times with water, and incubated in NMP overnight to decolorize.

Target Screen with His-tagged CD8α Protein. The 45 hits obtained from the second product screen were washed with water ten times and TBS three times. Next, the 24 hits isolated for CD8 Epitope1 and the 45 hits isolated for CD8 Epitope2 were transferred to two Corning® 8162 Costar® Spin-X® centrifuge tube filters (cellulose acetate membrane) and incubated with Blocking Buffer for 3 h at room temperature. The beads were rinsed three times with Blocking Buffer and then incubated with 150 nM of His-tagged CD8α human recombinant protein (TP760215, Origene) in Blocking Buffer (preparation: 20 µL His-tagged CD8α human recombinant protein in 630 µL Blocking Buffer) for 1 h at room temperature. The beads were washed three times with Blocking Buffer and then incubated with 500 µL of 1:10,000 Anti-6× His Tag® antibody [HIS-1] (Alkaline Phosphatase-conjugated) (ab49746, Abcam) in Blocking Buffer for 1 h at room temperature. The beads were subsequently washed with 3×500 µL Blocking Buffer, 3×500 µL TBS, then 3×500 µL Alkaline Phosphatase (pH 9) buffer (centrifuging at 7000 rpm for 30 sec after each wash). After this, the beads were developed with BCIP/NBT for 10 min. Purple hit beads bound to CD8α protein were selected by pipet and saved. Of the 24 product hits isolated for CD8 Epitope1, 3 beads were purple indicating binding to both the CD8 epitope and protein, while 21 were clear indicating no binding to CD8 protein. Of the 45 product hits isolated for CD8 Epitope2, 10 beads were purple indicating binding to both the CD8 epitope and protein, while 35 were clear indicating no binding to CD8 protein. The 3 target hits for CD8 Epitope1 and 10 target hits for CD8 Epitope2 were treated with 7.5 M guanidine hydrochloride pH 2.0 for 30 min to remove bound proteins, washed ten times with water, and incubated in NMP overnight to decolorize. The 13 hits were finally washed with water ten times to prepare for sequencing analysis.

Example 3: Sequencing Cyclic Peptide Hits by MALDI-TOF/TOF

Manual Edman Degradation. The process is shown with chemical structures in FIG. 2. Edman steps were adapted from Klemm Methods Mol. Biol. 1984. Cycle 1 (to remove the Pra click handle): Cyclic peptide hits were transferred in 5-10 µL water into a 10×75 mm Pyrex tube. The coupling reaction was initiated by adding 50 µL phenylisothiocyanate (2.5% (v/v) in 50% aq. pyridine) to the beads. The tube was flushed with N$_2$ (g) for 10 s, sealed with a rubber stopper, and allowed to react for 20 min at 50° C. The solution was washed once with 300 µL heptane: ethyl acetate (10:1). The tube was centrifuged at 500 rpm for 30 s, and the organic layer was removed by pipet (being careful to not disturb the beads at the bottom of the tube). The solution was then washed once with 300 µL heptane: ethyl acetate (1:2). The tube was centrifuged at 500 rpm for 30 s, and again the organic layer was removed by pipet. The remaining solution in the tube was dried under centrifugal vacuum at 60° C. for 10 min. The cleavage reaction was initiated by adding 50 µL trifluoroacetic acid to the beads. The tube was flushed with N$_2$ (g) for 10 s, lightly covered with a rubber stopper, and allowed to react for 10 min at 45° C. The trifluoroacetic acid was then removed by centrifugal vacuum for 10 min. The tube was then placed in an ice bath. Pyridine (50 µL) was added, and the solution was washed three times with 250 µL ice-cold n-butyl acetate saturated with water. The remaining solution (containing the beads) was then dried under centrifugal vacuum at 60° C. for 15 min. Cycle 2 (ring opening): Beads were taken up in 10 µL water and allowed to re-equilibrate. The coupling and cleavage reactions were performed again (following the same protocol as Cycle 1). The resulting beads containing the linear anilinothiazolinone (ATZ)-peptide were taken up in 200 µL water and allowed to re-equilibrate overnight at room temperature. On the next day, beads were transferred to a Corning® 8170 Costar® Spin-X® centrifuge tube filter (nylon membrane) and washed with 10×500 µL water by centrifuge (30 s, 7000 rpm).

Cleavage of Hit Peptides from Single Beads with Cyanogen Bromide (CNBr). Following the manual Edman degradation, each hit bead was transferred to a microcentrifuge tube containing pure water (10 μL). After addition of CNBr (10 μL, 0.50 M in 0.2 N HCl solution) the reaction vessel was purged with argon and then placed under microwave for 1 min (Lee et al. *J. Comb. Chem.* 2008). Acidic aq. CNBr results in methionine-specific cleavage at the C-terminus of the linear ATZ-peptide, resulting in cleavage of the peptide from the bead. The resulting solution was concentrated under centrifugal vacuum for 2 hours at 45° C.

Sequencing of Linear ATZ-Peptides Cleaved from Single Beads by MALDI-MS and MS/MS. To each tube was added a-cyano-4-hydroxycinnamic acid (CHCA) (0.5 μL, 5 mg/mL matrix solution in acetonitrile/water (70:30) containing 0.1% TFA (v/v)). The mixture was taken up to be spotted onto a 384-well MALDI plate, which was allowed to stand for 15 min to dry naturally. Samples were then analyzed by matrix-assisted laser-desorption/ionization (MALDI) time-of-flight (TOF) mass spectrometry (MS) using a Bruker ultrafleXtreme™ TOF/TOF instrument (Bruker Daltonics; Bremen, Germany) operated in reflectron mode. MS/MS spectra were acquired for each sample in LIFT™ mode. BioTools™ was used to assign the sequence based on analysis of the MS/MS spectra.

Sequencing results are shown in Tables 1 and 2. These candidate cyclic peptides were re-synthesized on a cleavable resin, purified by reversed phase HPLC using a Cis column (Phenomenex Luna, 5 μm, 250×10 mm), and tested for affinity and specificity against human CD8α protein by ELISA. Chemical structures and mass spectral data are shown in FIGS. 3-11 (panel A). In vitro characterization data of key compounds are elaborated in FIGS. 3-11.

TABLE 1

| Sequences of macrocyclic peptide hits identified against CD8 epitope 1 | | | | | |
|---|---|---|---|---|---|
| | x2 | x3 | x4 | x5 | x6 |
| hit1 | H | G | S | Y | G |
| hit2 | K | R | L | G | A |
| hit3 | A | K | Y | R | G |

TABLE 2

| Sequences of macrocyclic peptide hits identified against CD8 epitope 2 | | | | | |
|---|---|---|---|---|---|
| | x2 | x3 | x4 | x5 | x6 |
| hit1 | A | G | D | S | W |
| hit2 | H | V | R | H | G |
| hit3 | H | G | R | G | H |
| hit4 | T | H | P | T | T |
| hit5 | F | A | G | Y | H |
| hit6 | W | T | E | H | G |
| hit7 | P | W | T | H | G |
| hit8 | T | N | D | F | D |
| hit9 | L | F | P | F | D |

Example 4: Characterization Data for CD8 Epitope 1 Hits

TABLE 3

CD8 Epitope 1 Hits

1

Biotin-PEG₃——Cy(HGSYG) (SEQ ID NO: 6). MALDI-MS (m/z): calcd. for $C_{51}H_{74}N_{16}O_{15}S$ (M + H) 1183.52; found 1183.96.

TABLE 3-continued

CD8 Epitope 1 Hits

2

Biotin-PEG$_3$—Cy(KRLGA) (SEQ ID NO: 7). MALDI-MS (m/z): calcd. for C$_{52}$H$_{90}$N$_{18}$O$_{13}$S (M + H) 1207.67; found 1208.20.

3

Biotin-PEG$_3$—Cy(AKYRG) (SEQ ID NO: 8). MALDI-MS (m/z): calcd. for C$_{55}$H$_{88}$N$_{18}$O$_{14}$S (M + H) 1257.64; found 1257.81.

4

Biotin-PEG$_3$—Cy(hallw) (SEQ ID NO: 9). MALDI-MS (m/z): calcd. for C$_{61}$H$_{91}$N$_{17}$O$_{13}$S (M + H) 1302.67; found 1302.74.

TABLE 3-continued

CD8 Epitope 1 Hits

5

Biotin-PEG$_3$——Cy(lrGyw) (SEQ ID NO: 10). MALDI-MS (m/z): calcd. for C$_{63}$H$_{92}$N$_{18}$O$_{14}$S (M + H) 1357.68; found 1357.80.

6

Biotin-PEG$_3$——Cy(vashf) (SEQ ID NO: 11). MALDI-MS (m/z): calcd. for C$_{55}$H$_{82}$N$_{16}$O$_{14}$S (M + H) 1223.59; found 1223.60.

7

Biotin-PEG$_3$——Cy(wplrf) (SEQ ID NO: 13). MALDI-MS (m/z): calcd. for C$_{66}$H$_{96}$N$_{18}$O$_{13}$S (M + H) 1381.71; found 1381.76.

TABLE 3-continued

CD8 Epitope 1 Hits

8

Biotin-PEG₃—Cy(rwfnv) (SEQ ID NO: 14). MALDI-MS (m/z): calcd. for $C_{64}H_{93}N_{19}O_{14}S$ (M + H) 1384.69; found 1384.99.

9

Biotin-PEG₃—Cy(havwh) (SEQ ID NO: 15). MALDI-MS (m/z): calcd. for $C_{60}H_{85}N_{19}O_{13}S$ (M + H) 1312.63; found 1312.79.

TABLE 3-continued

CD8 Epitope 1 Hits

10

Biotin-PEG$_3$—Cy(wvplw) (SEQ ID NO: 16). MALDI-MS (m/z): calcd. for C$_{67}$H$_{94}$N$_{16}$O$_{13}$S (M + H) 1363.69; found 1364.00.

11

Biotin-PEG$_3$—Cy(ffrly) (SEQ ID NO: 17). MALDI-MS (m/z): calcd. for C$_{68}$H$_{97}$N$_{17}$O$_{14}$S (M + H) 1408.71; found 1409.14.

TABLE 3-continued

| CD8 Epitope 1 Hits |
|---|

12

Biotin-PEG₃—Cy(wyyGf) (SEQ ID NO: 18). MALDI-MS (m/z): calcd. for C₆₉H₈₇N₁₅O₁₅S (M + H) 1398.62; found 1399.81.

13

Biotin-PEG₃—Cy(nGnvh) (SEQ ID NO: 12). MALDI-MS (m/z): calcd. for C₅₀H₇₈N₁₈O₁₅S (M + H) 1203.56; found 1204.00.

Example 5: Screening a Linear Library Against CD8 Epitopes 1 and 2

Screens were performed using a linear OBOC library of the form H2N-(D-Pra)-xxxxx-(D-Met)-TG (SEQ ID NO: 47), where TG-TentaGel® S NH₂ resin (S 30 902, Rapp Polymere), x=one of sixteen D-amino acids (lacking D-Cys, D-Met, D-Ile, and D-GLn), and D-Pra=D-propargylglycine. Linear peptide ligands were identified against the two CD8 epitope fragments using a four-step screening process: 1) a pre-clear to eliminate non-specific binders, 2) a product screen to identify hits resulting from CD8 Epitope1-templated in situ click chemistry, 3) another product screen to identify hits resulting from CD8 Epitope2-templated in situ click chemistry, and 4) a target screen against His-tagged CD8α human recombinant protein to identify peptides that bind to the protein as well as the epitopes.

Pre-clear. Swelled library beads (400 mg) were blocked overnight with Blocking Buffer (25 mM Tris-HCl, 150 mM NaCl, 1% (w/v) BSA, and 0.05% (v/v) Tween-20, pH 7.6) at 4° C., then washed with Blocking Buffer three times. A 1:10,000 dilution of Streptavidin-Alkaline Phosphatase (V559C, Promega) in 5 mL Blocking Buffer was added to the beads and incubated with gentle shaking at room temperature for 1 h. The beads were subsequently washed with 3×3 mL TBS (25 mM Tris-HCl, 150 mM NaCl, pH 7.6) (1 min ea), 3×3 mL 0.1 M glycine pH 2.8 wash buffer, 3×3 mL TBS, then 3×3 mL Alkaline Phosphatase buffer (100 mM Tris-HCl, 150 mM NaCl, 1 mM MgCL₂, pH 9) (5 min ea). Binding was visualized by incubating the beads in the presence of 5-bromo-4-chloro-3-indolyl phosphate/nitro blue tetrazolium (BCIP/NBT) substrate (S3771, Promega) for 25 min. Purple beads indicated background binders and were removed by pipet and discarded. The remaining clear beads were collected and stripped with 7.5 M guanidine hydrochloride pH 2.0 for 30 min, washed ten times with water, and incubated in NMP overnight to decolorize.

Product Screen with CD8 Epitope 1. Beads remaining from the pre-clear were washed with water ten times and TBS three times. Beads were then incubated with 3 mL of 100 μM CD8 Epitope1 fragment (Biotin-PEG₃-SQFRVSPLD[Az4]TWNLGETVELKSQ) (SEQ ID NO: 2) in TBS for 3 h at room temperature to allow for an in situ click reaction to occur. The beads were washed with TBS ten times and then incubated with 7.5 M guanidine hydrochloride pH 2.0 for 1 h to remove all CD8 epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of CD8 epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet. These 19 hits and separately the non-hits were treated with 7.5 M guanidine hydrochloride pH 2.0 for 30 min to remove attached streptavidin, washed ten times with water, and incubated in NMP overnight to decolorize.

Product Screen with CD8 Epitope 2. The 19 hits and separately the non-hit beads obtained from the product screen were washed with water ten times and TBS three times. The non-hit beads were then incubated with 3 mL of 100 μM CD8 Epitope2 fragment (Biotin-PEG$_3$-FLLY-LSQNKP[Az4]AAEGLDTQR) (SEQ ID NO: 5) in TBS for 3 h at room temperature to allow for an in situ click reaction to occur. The beads were washed with TBS ten times and then incubated with 7.5 M guanidine hydrochloride pH 2.0 for 1 h to remove all CD8 epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of CD8 epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet. These 19 hits were treated with 7.5 M guanidine hydrochloride pH 2.0 for 30 min to remove attached streptavidin, washed ten times with water, and incubated in NMP overnight to decolorize.

Target Screen with His-tagged CD8α Protein. The 19 hits obtained from the second product screen were washed with water ten times and TBS three times. Next, the 19 hits isolated for CD8 Epitope1 and the 19 hits isolated for CD8 Epitope2 were transferred to two Corning® 8162 Costar® Spin-X® centrifuge tube filters (cellulose acetate membrane) and incubated with Blocking Buffer for 3 h at room temperature. The beads were rinsed three times with Blocking Buffer and then incubated with 1.5 μM of His-tagged CD8α human recombinant protein (TP760215, Origene) in Blocking Buffer (preparation: 136.4 μL His-tagged CD8α human recombinant protein in 303.6 μL Blocking Buffer) for 1 h at room temperature. The beads were washed three times with Blocking Buffer and then incubated with 500 μL of 1:10,000 Anti-6× His Tag® antibody [HIS-1] (Alkaline Phosphatase-conjugated) (ab49746, Abcam) in Blocking Buffer for 1 h at room temperature. The beads were subsequently washed with 3×500 μL Blocking Buffer, 3×500 μL TBS, then 3×500 μL Alkaline Phosphatase (pH 9) buffer (centrifuging at 7000 rpm for 30 sec after each wash). After this, the beads were developed with BCIP/NBT for 10 min. Purple hit beads bound to CD8α protein were selected by pipet and saved. Of the 19 product hits isolated for CD8 Epitope1, 10 beads were purple indicating binding to both the CD8 epitope and protein, while 9 were clear indicating no binding to CD8 protein. Of the 19 product hits isolated for CD8 Epitope2, 13 beads were purple indicating binding to both the CD8 epitope and protein, while 6 were clear indicating no binding to CD8 protein. The 10 target hits for CD8 Epitope1 and 13 target hits for CD8 Epitope2 were treated with 7.5 M guanidine hydrochloride pH 2.0 for 30 min to remove bound proteins, washed ten times with water, and incubated in NMP overnight to decolorize. The 23 hits were finally washed with water ten times to prepare for sequencing analysis.

Example 6: Sequencing Linear Peptide Hits by MALDI-TOF/TOF

Cleavage of Hit Peptides from Single Beads with Cyanogen Bromide (CNBr). Each hit bead was transferred to a microcentrifuge tube containing pure water (10 μL). After addition of CNBr (10 μL, 0.50 M in 0.2 N HCl solution) the reaction vessel was purged with argon and then placed under microwave for 1 min (Lee et al. J. Comb. Chem. 2008). Acidic aq. CNBr results in methionine-specific cleavage at the C-terminus of the peptide, resulting in cleavage of the peptide from the bead. The resulting solution was concentrated under centrifugal vacuum for 2 hours at 45° C.

Sequencing of Hit Peptides Cleaved from Single Beads by MALDI-MS and MS/MS. To each tube was added a-cyano-4-hydroxycinnamic acid (CHCA) (0.5 μL, 5 mg/mL matrix solution in acetonitrile/water (70:30) containing 0.1% TFA (v/v)). The mixture was taken up to be spotted onto a 384-well MALDI plate, which was allowed to stand for 15 min to dry naturally. Samples were then analyzed by matrix-assisted laser-desorption/ionization (MALDI) time-of-flight (TOF) mass spectrometry (MS) using a Bruker ultrafleXtreme™ TOF/TOF instrument (Bruker Daltonics; Bremen, Germany) operated in reflectron mode. MS/MS spectra were acquired for each sample in LIFT™ mode. BioTools™ was used to assign the sequence based on analysis of the MS/MS spectra.

Sequencing results are shown in Tables 4 and 5. These candidate peptides were re-synthesized exclusively in the triazole-cyclized form on a cleavable resin, purified by reversed phase HPLC using a C$_{18}$ column (Phenomenex Luna, 5 μm, 250× 10 mm), and tested for affinity and specificity against human CD8α protein by ELISA. Chemical structures and mass spectral data are shown in FIGS. 3-11 (panel A). In vitro characterization data of key compounds are elaborated in FIGS. 3-11.

TABLE 4

| Sequences of linear peptide hits identified against CD8 Epitope1 | | | | | |
|---|---|---|---|---|---|
| | x2 | x3 | x4 | x5 | x6 |
| hit1 | h | a | l | l | w |
| hit2 | l | r | G | y | w |
| hit3 | v | a | s | h | f |
| hit4 | n | G | n | v | h |
| hit5 | w | p | l | r | f |
| hit6 | r | w | f | n | v |
| hit7 | h | a | v | w | h |
| hit8 | w | v | p | l | w |
| hit9 | f | f | r | l | y |
| hit10 | w | y | y | G | f |

TABLE 5

| Sequences of linear peptide hits identified against CD8 Epitope2 | | | | | |
|---|---|---|---|---|---|
| | x2 | x3 | x4 | x5 | x6 |
| hit1 | s | l | r | f | G |
| hit2 | y | f | r | G | s |
| hit3 | w | n | w | v | G |
| hit4 | v | a | w | l | G |
| hit5 | f | h | v | h | G |

TABLE 5-continued

Sequences of linear peptide hits identified against CD8 Epitope2

|  | x2 | x3 | x4 | x5 | x6 |
|---|---|---|---|---|---|
| hit6 | w | v | s | n | v |
| hit7 | w | s | v | n | v |
| hit8 | l | n | s | h | G |
| hit9 | y | G | G | v | r |
| hit10 | n | s | v | h | G |
| hit11 | t | t | v | h | G |

TABLE 5-continued

Sequences of linear peptide hits identified against CD8 Epitope2

|  | x2 | x3 | x4 | x5 | x6 |
|---|---|---|---|---|---|
| hit12 | f | d | v | G | h |
| hit13 | r | h | G | w | k |

Example 7: Characterization Data for CD8 Epitope 2 Hits

TABLE 6

CD8 Epitope 2 Hits

14

Biotin-PEG$_3$—Cy(AGDSW) (SEQ ID NO: 19). MALDI-MS (m/z): calcd. for C$_{52}$H$_{75}$N$_{15}$O$_{16}$S (M + H) 1198.52; found 1220.88 (+Na).

15

Biotin-PEG$_3$—Cy(HVRHG) (SEQ ID NO: 20). MALDI-MS (m/z): calcd. for C$_{54}$H$_{85}$N$_{21}$O$_{13}$S (M + H) 1268.64; found 1268.76.

TABLE 6-continued

CD8 Epitope 2 Hits

16

Biotin-PEG$_3$——Cy(HGRGH) (SEQ ID NO: 21). MALDI-MS (m/z): calcd. for C$_{51}$H$_{79}$N$_{21}$O$_{13}$S (M + H) 1226.59; found 1227.25.

17

Biotin-PEG$_3$——Cy(THPTT) (SEQ ID NO: 22). MALDI-MS (m/z): calcd. for C$_{52}$H$_{82}$N$_{16}$O$_{16}$S (M + H) 1219.58; found 1219.72.

18

Biotin-PEG$_3$——Cy(FAGYH) (SEQ ID NO: 23). MALDI-MS (m/z): calcd. for C$_{58}$H$_{80}$N$_{16}$O$_{14}$S (M + H) 1257.58; found 1257.53.

TABLE 6-continued

CD8 Epitope 2 Hits

19

Biotin-PEG$_3$——Cy(WTEHG) (SEQ ID NO: 24). MALDI-MS (m/z): calcd. for $C_{57}H_{81}N_{17}O_{16}S$ (M + H) 1292.58; found 1293.10.

20

Biotin-PEG$_3$——Cy(PWTHG) (SEQ ID NO: 25). MALDI-MS (m/z): calcd. for $C_{57}H_{81}N_{17}O_{14}S$ (M + H) 1260.59; found 1260.95.

21

Biotin-PEG$_3$——Cy(TNDFD) (SEQ ID NO: 26). MALDI-MS (m/z): calcd. for $C_{54}H_{79}N_{15}O_{19}S$ (M + H) 1274.54; found 1274.61.

TABLE 6-continued

CD8 Epitope 2 Hits

22

Biotin-PEG$_3$——Cy(LFPFD) (SEQ ID NO: 27). MALDI-MS (m/z): calcd. for C$_{62}$H$_{88}$N$_{14}$O$_{15}$S (M + H) 1301.63; found 1301.76.

23

Biotin-PEG$_3$——Cy(slrfG) (SEQ ID NO: 28). MALDI-MS (m/z): calcd. for C$_{55}$H$_{87}$N$_{17}$O$_{14}$S (M + H) 1242.63; found 1242.73.

24

Biotin-PEG$_3$——Cy(yfrGs) (SEQ ID NO: 29). MALDI-MS (m/z): calcd. for C$_{58}$H$_{85}$N$_{17}$O$_{15}$S (M + H) 1292.61; found 1292.77.

TABLE 6-continued

CD8 Epitope 2 Hits

25

Biotin-PEG₃—Cy(wnwvG) (SEQ ID NO: 30). MALDI-MS (m/z): calcd. for $C_{62}H_{85}N_{17}O_{14}S$ (M + H) 1324.62; found 1347.21 (+Na).

26

Biotin-PEG₃—Cy(vawlG) (SEQ ID NO: 31). MALDI-MS (m/z): calcd. for $C_{56}H_{85}N_{15}O_{13}S$ (M + H) 1208.62; found 1231.03 (+Na).

27

Biotin-PEG₃——Cy(fhvhG) (SEQ ID NO: 32). MALDI-MS (m/z): calcd. for $C_{57}H_{82}N_{18}O_{13}S$ (M + H) 1259.60; found 1260.10.

TABLE 6-continued

CD8 Epitope 2 Hits

28

Biotin-PEG$_3$——Cy(wvsnv) (SEQ ID NO: 33). MALDI-MS (m/z): calcd. for C$_{57}$H$_{86}$N$_{16}$O$_{15}$S (M + H) 1267.62; found 1289.70 (+Na).

29

Biotin-PEG$_3$——Cy(wsvnv) (SEQ ID NO: 34). MALDI-MS (m/z): calcd. for C$_{57}$H$_{86}$N$_{16}$O$_{15}$S (M + H) 1267.62; found 1289.62 (+Na).

30

Biotin-PEG$_3$——Cy(lnshG) (SEQ ID NO: 35). MALDI-MS (m/z): calcd. for C$_{50}$H$_{79}$N$_{17}$O$_{15}$S (M + H) 1190.57; found 1190.68.

TABLE 6-continued

CD8 Epitope 2 Hits

31

Biotin-PEG$_3$—Cy(yGGvr) (SEQ ID NO: 36). MALDI-MS (m/z): calcd. for C$_{53}$H$_{83}$N$_{17}$O$_{14}$S (M + H) 1214.60; found 1214.72.

32

Biotin-PEG$_3$—Cy(nsvhG) (SEQ ID NO: 37). MALDI-MS (m/z): calcd. for C$_{49}$H$_{77}$N$_{17}$O$_{15}$S (M + H) 1176.55; found 1176.58.

33

Biotin-PEG$_3$—Cy(ttvhG) (SEQ ID NO: 38). MALDI-MS (m/z): calcd. for C$_{50}$H$_{80}$N$_{16}$O$_{15}$S (M + H) 1177.57; found 1177.72.

TABLE 6-continued

CD8 Epitope 2 Hits

34

Biotin-PEG₃—Cy(fdvGh) (SEQ ID NO: 39). MALDI-MS (m/z): calcd. for C₅₅H₈₀N₁₆O₁₅S (M + H) 1237.57; found 1237.78.

35

Biotin-PEG₃—Cy(rhGwk) (SEQ ID NO: 40). MALDI-MS (m/z): calcd. for C₆₀H₉₁N₂₁O₁₃S (M + H) 1346.68; found 1346.76.

Example 8: In Vitro Assays with CD8 Epitope Targeted Ligands

CD8 ELISA (Affinity assay). Protocol: A black 96-well NeutrAvidin Coated High Binding Capacity plate (15510, Pierce) was coated with 2 μM macrocyclic peptide ligand in TBS (25 mM Tris-HCl, 150 mM NaCl, pH 7.6) for 2 h at room temperature. Biotinylated monoclonal anti-CD8 (MA1-19484, Life Technologies) was coated at 4 μg/mL in TBS as a control. The plate was aspirated and then washed with TBS (5×) and Wash Buffer (0.05% (v/v) Tween-20 in PBS, 1×). His-tagged CD8α human recombinant protein (TP760215, Origene) was serially diluted in Wash Buffer (from 400 to 0 nM) and incubated in the designated microwells for 90 min at room temperature. Microwells were aspirated and subsequently washed with Wash Buffer (10×). To detect the bound CD8α protein, Alkaline Phosphatase (AP)-conjugated Anti-6× His Tag® antibody [HIS-1] (ab49746, Abcam) was prepared at 1:10,000 dilution and added to the microwells for 1 h at room temperature. The plate was aspirated and washed with Wash Buffer (5×). AttoPhos® AP Fluorescent Substrate System (S1000, Promega) was employed to develop the microwells. Using an excitation wavelength of 430 nm, fluorescent emission at 535 nm was recorded by Beckman Coulter DTX880 photometer. Titration curves were fit using a four-parameter regression curve fitting program (Origin 8.5) to determine EC₅₀ values.

The binding affinities of biotin-PEG₃-modified macrocyclic peptide ligands were tested in an ELISA format. For these assays, a dilution series of His-tagged CD8α human recombinant protein was captured using the macrocyclic peptide ligands immobilized on a NeutrAvidin-coated plate. The macrocyclic peptide ligands displayed EC₅₀ values ranging from 6 to 62 nM for human CD8α protein. A similarly assayed biotinylated monoclonal anti-CD8 shows similar binding affinity (EC₅₀~60 nM). Results for key compounds are shown in FIGS. 3-11 (panel B).

Point ELISA (Serum selectivity assay). Protocol: A black 96-well NeutrAvidin Coated High Binding Capacity plate (15510, Pierce) was coated with 2 μM macrocyclic peptide ligand in TBS (pH 7.6) for 2 h at room temperature. The plate was aspirated and then washed with TBS (5×) and Wash Buffer (0.05% (v/v) Tween-20 in PBS, 1×). His-tagged CD8α human recombinant protein (TP760215, Origene) was prepared at 50 nM in 0%, 10%, 50%, and 100% (v/v) human serum (HS-30, Omega Scientific; dilutions made in Wash Buffer) and incubated in the designated microwells for 90 min at room temperature. Microwells were aspirated and subsequently washed with Wash Buffer (10×). To detect the bound CD8α protein, Alkaline Phosphatase (AP)-conjugated Anti-6× His Tag® antibody [HIS-1] (ab49746, Abcam) was prepared at 1:10,000 dilution and added to the microwells for 1 h at room temperature. The plate was aspirated and washed with Wash Buffer (5×). AttoPhos® AP Fluorescent Substrate System (S1000, Promega) was employed to develop the microwells. Using an excitation wavelength of 430 nm, fluorescent emission at 535 nm was recorded by Beckman Coulter DTX880 photometer.

The selective targeting of biotin-PEG₃-modified macrocyclic peptide ligands in a serum background was tested in an ELISA format. For these assays, 50 nM His-tagged CD8α human recombinant protein was captured in 0%, 10%, 50%, and 100% (v/v) human serum using immobilized macrocyclic peptide ligands. The most selective ligands are Cy(yGGvr) (SEQ ID NO: 36) and Cy(HGRGH) (SEQ ID NO: 21) which can detect CD8 protein in 50% serum. Other PCCs, including Cy(AKYRG) (SEQ ID NO: 8), CY(PWTHG) (SEQ ID NO: 25), and Cy(wsvnv) (SEQ ID NO: 34), can detect CD8 protein in 10% serum. Results for key compounds are shown in FIGS. 3-11 (panel C).

Point ELISA (Protease sensitivity assay). Protocol: A 1:30 ratio of trypsin (T0303, Sigma-Aldrich; 1 mg/mL stock in 1 mM HCl, pH 3) was prepared. Reactions were set up with 2.5 µL macrocyclic peptide ligand, 5 µL 1:100 diluted trypsin, and 17.5 µL 1×TBS and incubated at 37° C. for 1 h. Also, reactions were set up with 2.0 µL Biotinylated monoclonal anti-CD8 (MA1-19484, Life Technologies), 5 µL undiluted trypsin, and 18 µL 1×TBS and incubated at 37° C. for 1 h. After digestion, the volume of each sample was increased to 500 µL total with 1×TBS and 100 µL was used per well of a 96-well NeutrAvidin plate (15510, Pierce). The CD8 ELISA (Affinity assay) was performed as described above using 50 nM His-tagged CD8α human recombinant protein (TP760215, Origene).

Trypsin can cleave peptides and proteins (including antibodies) on the C-terminal side of lysine and arginine L-amino acid residues. For this assay, test compounds were treated with trypsin protease (1 h at 37° C.) or left untreated as a control. The CD8 ELISA showed that the digested anti-CD8 antibody lost nearly all of its CD8 capturing ability, while most macrocyclic peptide ligands were resistant to protease digestion. Five d-amino acid containing PCCs (Cy(wplrf) (SEQ ID NO: 13), Cy(slrfG) (SEQ ID NO: 28), Cy(ffrly) (SEQ ID NO: 17), Cy(yGGvr) (SEQ ID NO: 36), and Cy(wsvnv) (SEQ ID NO: 34)) were very stable, showing nearly identical signals before and after digestion. Another d-amino acid containing PCC (Cy(rwfnv) (SEQ ID NO: 14)) retained 80% of signal after protease treatment. Cy(AKYRG) (SEQ ID NO: 8), which consists of lysine and arginine L-amino acids, was the cyclic PCC most susceptible to trypsin and displayed only 30% of signal after treatment. Results for key compounds are shown in FIGS. 3-11 (panel D).

Example 9: Binding Location Analysis with Modified CD8 Epitopes

Assay to determine orientation of macrocycle binding to CD8 Epitopes1-2. Protocol: A black 96-well NeutrAvidin Coated High Binding Capacity plate (15510, Pierce) was coated with 2 µM macrocyclic peptide ligand in TBS (pH 7.6) for 2 h at room temperature. The plate was aspirated and then washed with TBS (5×) and Wash Buffer (0.05% (v/v) Tween-20 in PBS, 1×). Chemically synthesized His-tagged CD8 epitopes were prepared at 2 µM in Wash Buffer and incubated in the designated microwells for 90 min at room temperature. Wash Buffer without epitope was added as a control. Microwells were aspirated and subsequently washed with Wash Buffer (10×). To detect the bound CD8 epitopes, Alkaline Phosphatase (AP)-conjugated Anti-6× His Tag® antibody [HIS-1] (ab49746, Abcam) was prepared at 1:10,000 dilution and added to the microwells for 1 h at room temperature. The plate was aspirated and washed with Wash Buffer (5×). AttoPhos® AP Fluorescent Substrate System (S1000, Promega) was employed to develop the microwells. Using an excitation wavelength of 430 nm, fluorescent emission at 535 nm was recorded by Beckman Coulter DTX880 photometer. Data are shown after subtraction of the no-epitope background.

For this experiment, the CD8 Epitope1 was re-synthesized with a His₆ assay handle and polyglycine substitution of the sequences either N-terminal or C-terminal to the location of the click handle (R10) (FIG. 12A). The CD8 Epitope2 was similarly re-synthesized with a His₆ assay handle and polyglycine substitution (N-terminal or C-terminal to K58) (FIG. 12B). Point ELISAs for the His-tagged CD8 epitopes were conducted against the immobilized macrocyclic peptide ligands. For PEG₃-biotin-modified Cy(wplrf) (SEQ ID NO: 13), Cy(AKYRG) (SEQ ID NO: 8), Cy(rwfnv) (SEQ ID NO: 14), and Cy(ffrly) (SEQ ID NO: 17), maximum ELISA signals were obtained for binding to CD8 Epitope1N (dark bars, FIG. 12C) indicating preferential binding to the N-terminal portion of CD8 Epitope1. For PEG₃-biotin-modified Cy(PWTHG) (SEQ ID NO: 25), Cy(yGGvr) (SEQ ID NO: 36), and Cy(slrfG) (SEQ ID NO: 28), maximum ELISA signals were obtained for binding to CD8 Epitope2N (black bars, FIG. 12D) indicating preferential binding to the N-terminal portion of CD8 Epitope2. For PEG₃-biotin-modified Cy(HGRGH) (SEQ ID NO: 21) and Cy(wsvnv) (SEQ ID NO: 34), maximum ELISA signals were obtained for binding to CD8 Epitope2C (light grey bars, FIG. 12D) indicating preferential binding to the C-terminal portion of CD8 Epitope2. These results confirm the selective nature of the epitope-targeting strategy.

Figure 13:
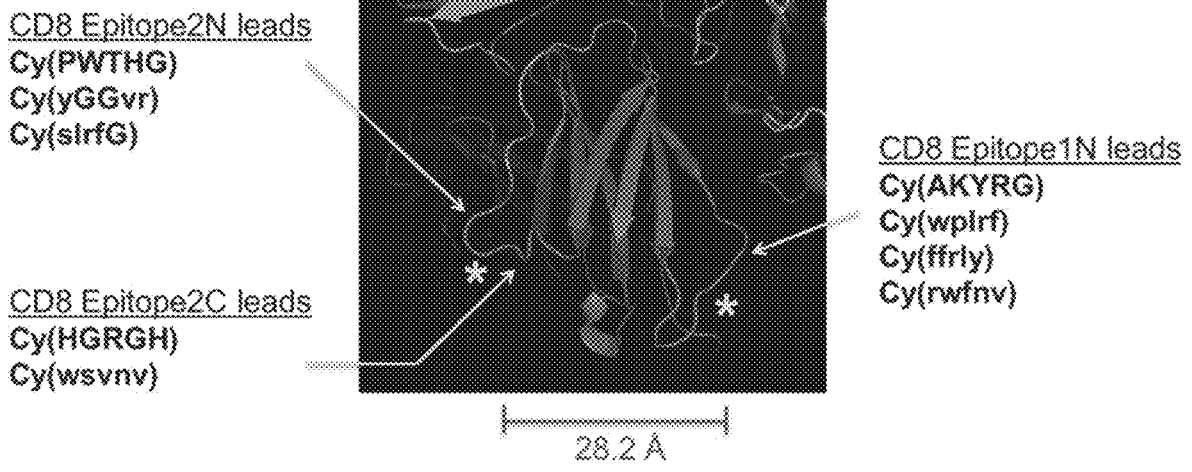
FIG. 13 shows a summary of macrocycle binding orientations overlaid with the CD8α crystal structure (PDB ID: 1AKJ). Four PCCs (Cy(AKYRG) (SEQ ID NO: 8), Cy(wplrf) (SEQ ID NO: 13), Cy(ffrly) (SEQ ID NO: 17), and Cy(rwfnv) (SEQ ID NO: 14)) were found to bind to CD8 Epitope1N. Three PCCs (Cy(PWTHG) (SEQ ID NO: 25), Cy(yGGvr) (SEQ ID NO: 36), and Cy(slrfG) (SEQ ID NO: 28)) were found to bind to CD8 Epitope2N. Two PCCs (Cy(HGRGH) (SEQ ID NO: 21) and Cy(wsvnv) (SEQ ID NO: 34)) were found to bind to CD8 Epitope2C. The star (*) indicates the location of the azide handle (Az4) in the synthetic epitope.

The results shown in FIGS. 3-12 show that the epitope-targeting strategy produced sub-100 nM affinity, stable macrocyclic peptide ligands that recognize specific portions of CD8 epitopes as well as the human recombinant protein. A summary of macrocycle binding orientations overlaid with the CD8α crystal structure is shown in FIG. 13.

Example 10: Designing a Linker to Covalently Join Two Macrocyclic Ligands

The tertiary structure of the CD8α protein was subsequently exploited as a scaffold for developing a biligand PCC agent that exhibits true cooperative binding ($K_D$ range of <1 nM). Combinations of two macrocycles are covalently joined together to create a biligand PCC agent that displays high avidity for the two epitopes.

Figure 14:
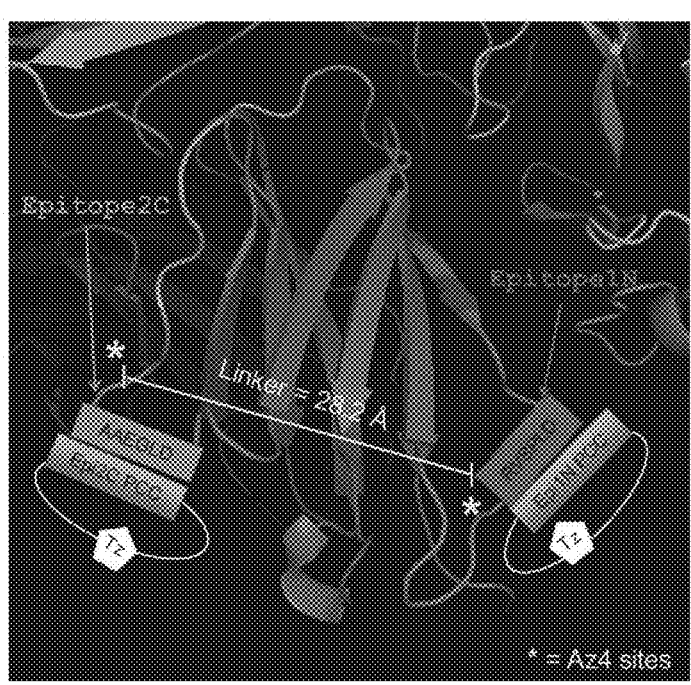
FIG. 14 depicts a 3-D structural representations of CD8a. The sequences of CD8 Epitopes1-2 and representative epitope-targeted macrocycles are overlaid (Tz=triazole). The distance (Å) measured between the two epitopes is shown with a line labeled "Linker=28.2 Å". In the monomeric CD8α protein, the distance between the sequences AAEGLD (SEQ ID NO: 42) (in CD8 Epitope2C) and RVSPLD (SEQ ID NO: 43) (in CD8 Epitope1N) is ~28.2 Å. Using a linker whose length is similar to the distance between the two binding sites on the protein, a biligand can be synthesized containing PCC macrocycles targeted to each of the two CD8 epitopes. PDB ID: 1AKJ.

Important to this process is the design of a suitable linker to bridge the distance between the two epitopes of the protein. The 3-D crystal structure of human CD8 (PDB ID: 1AKJ) was analyzed in PyMOL (DeLano Scientific) to identify the distances between CD8 Epitope1 and CD8 Epitope2 (FIG. 14). In CD8 Epitope1, the sequence RVSPLD (SEQ ID NO: 43) was focused on because the macrocycles Cy(AKYRG) (SEQ ID NO: 8), Cy(wplrf) (SEQ ID NO: 13), Cy(ffrly) (SEQ ID NO: 17), and Cy(rwfnv) (SEQ ID NO: 14) were determined to interact with this N-terminal region preferentially (FIG. 12). In CD8 Epitope2, the sequence AAEGLD (SEQ ID NO: 42) was focused on because the macrocycles Cy(HGRGH) (SEQ ID NO: 21) and Cy(wsvnv) (SEQ ID NO: 34) were determined to interact with this C-terminal region preferentially (FIG. 12). The distance was then measured between the locations of the two epitopes in one monomer of the CD8αα dimer. In the monomeric CD8α protein, the sequences AAEGLD (SEQ ID NO: 42) (in CD8 Epitope2C) and RVSPLD (SEQ ID NO: 43) (in CD8 Epitope1N) are separated by ~28.2 Å. Thus, a chemical linker of ~30 Å would be useful for covalently joining one macrocycle targeted to CD8 Epitope1 and one macrocycle targeted to CD8 Epitope2. The resultant cooperative biligands would be useful for detection of both CD8αα and CD8αβ.

Example 11: Synthesis of Cooperative Biligand Candidates Using PEG Linkers

Cooperative biligand candidates were synthesized with a variable length PEG linker covalently joining one macrocycle from CD8 Epitope1 with one macrocycle from CD8 Epitope2. The linker connecting the two macrocycles is a single PEGylated amino acid (Fmoc-NH-PEG$_x$-Propionic Acid; x=1 to 8). A PEG linker was chosen because it is available in various lengths that would bridge the ~28.2 Å distance between the two epitopes of the protein. PEG also is expected to display favorable hydrophilicity and anti-biofouling properties.

Figure 15:
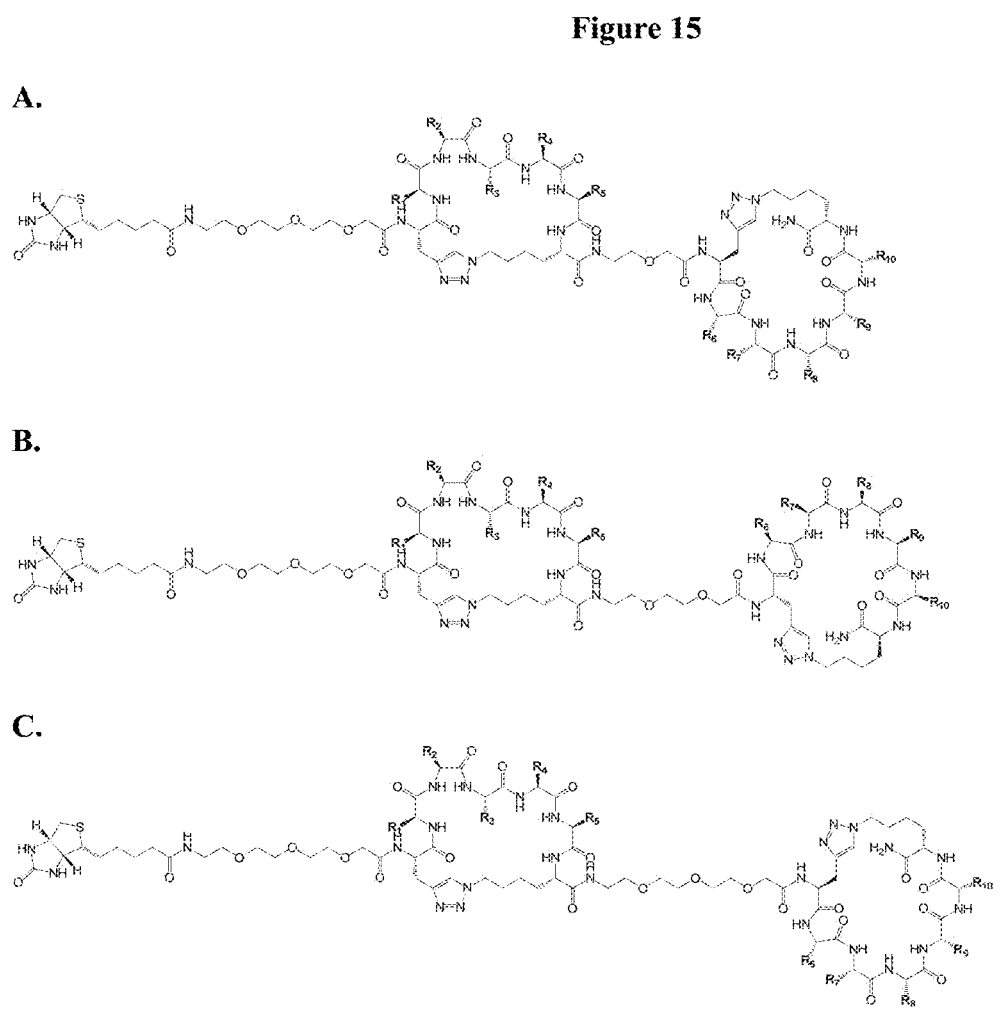
Figure 15:
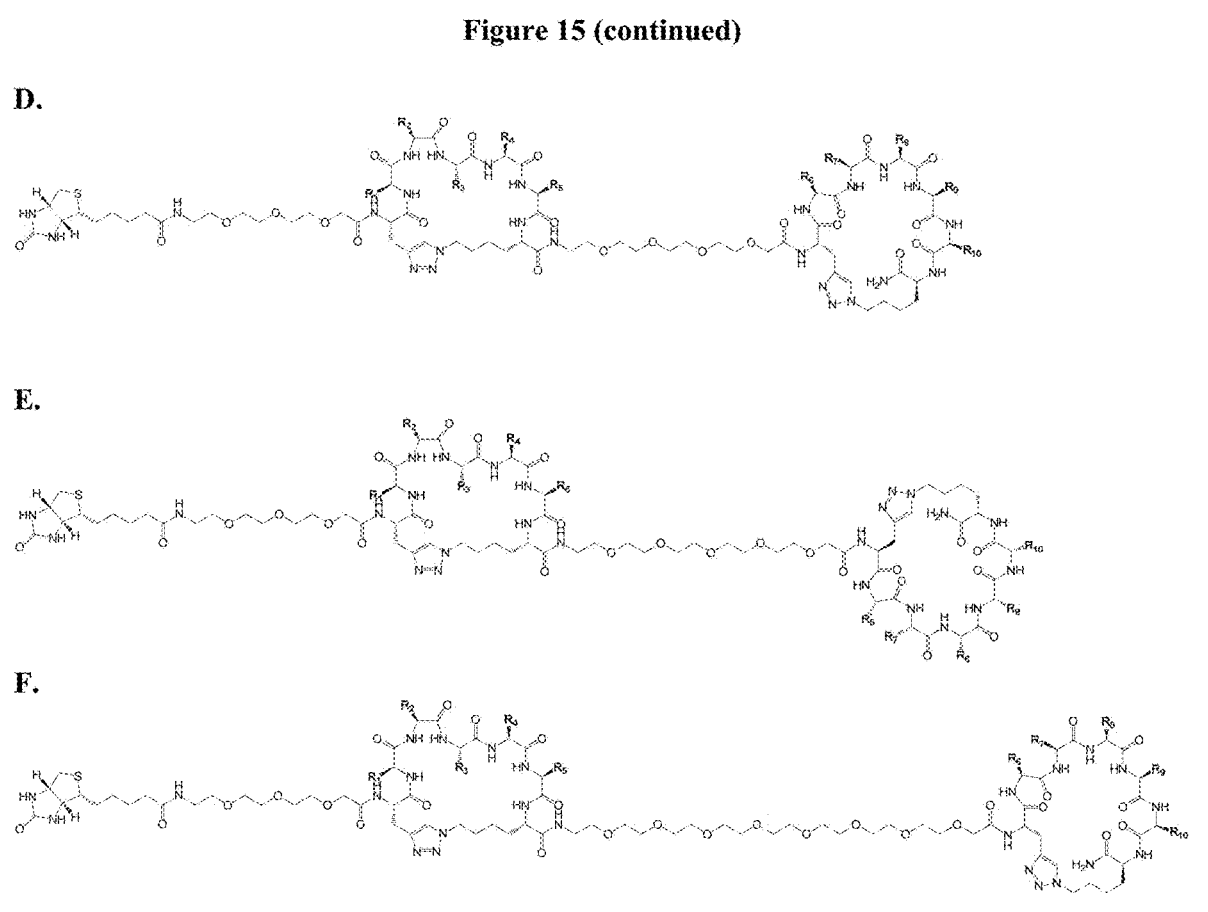

Cooperative biligand candidates were first generated from macrocycles Cy(Epi2C PCC) (targeted to CD8 Epitope2C) and Cy(Epi1N PCC) (targeted to CD8 Epitope1N), where the Epi2C PCC=macrocycles selected from HGRGH (SEQ ID NO: 21) or wsvnv (SEQ ID NO: 34), and Epi1N PCC=macrocycles selected from AKYRG (SEQ ID NO: 8), wplrf (SEQ ID NO: 13), ffrly (SEQ ID NO: 17), or rwfnv (SEQ ID NO: 14). Structures of the cooperative biligand candidates Biotin-PEG$_3$-Cy(Epi2C PCC)-PEG.-Cy(Epi1N PCC) are shown in FIG. 15. Also, cooperative biligand candidates can be generated from macrocycles Cy(Epi2N PCC) (targeted to CD8 Epitope2N) and Cy(Epi1N PCC) (targeted to CD8 Epitope1N), where Epi2N PCC=macrocycles selected from PWTHG (SEQ ID NO: 25), yGGvr (SEQ ID NO: 36), or slrfG (SEQ ID NO: 28).

Figure 16:
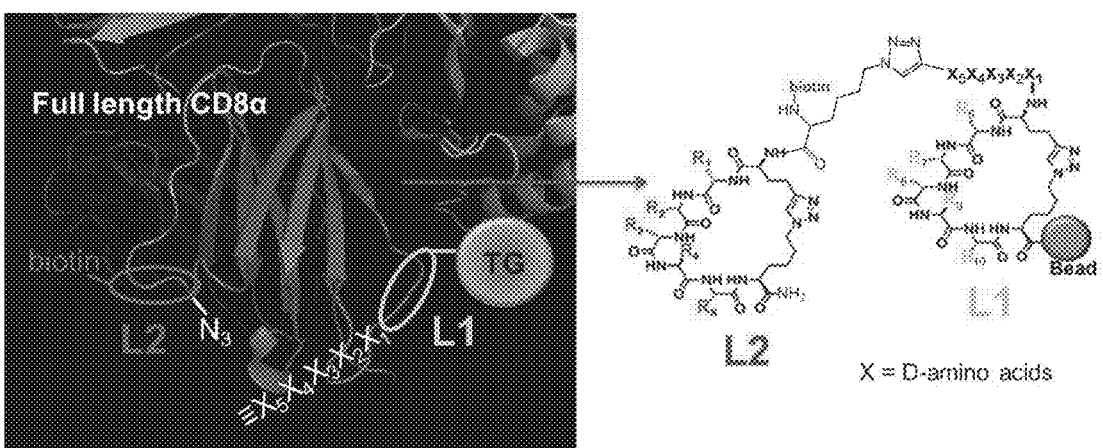
FIG. 16 depicts a general scheme of cooperative biligand screen with amino acid linkers (ranging from 0 to 5 D-amino acids in length) to join the two macrocycles. The CD8α protein templates the target-guided synthesis of biligands by bringing the reactive azide (from Epi2C PCC=L2) and alkyne (from Epi1N PCC=L1) groups in close proximity.

Example 12: Synthesis of Cooperative Biligand Candidates Using Amino Acid Linkers Additional biligand candidates were developed using in situ click chemistry to identify a linear peptide that covalently links together the two macrocycles when bound to the CD8α protein (FIG. 16). To combine Cy(Epi2C PCC) with Cy(Epi1N PCC), kinetically controlled in situ click chemistry was used with a combinatorial linker library to identify a molecular bridge. First, Cy(Epi1N PCC) was synthesized on solid-phase resin and appended with an N-terminal linker library that was terminated with D-propargylglycine (D-Pra). This linker library was comprehensive from zero to five residues in seven D-amino acids, which were selected for hydrophilicity and structural rigidity. Cy(Epi2C PCC) was re-synthesized with a C-terminal Az4 (L-azidolysine) and an N-terminal Biotin-PEG$_3$ label. The CD8α protein was added to achieve the target-guided synthesis of a biligand PCC agent by bringing the reactive azide (from Epi2C PCC) and alkyne (from Epi1N PCC) groups in close proximity.

Protocol: Screens to identify an amino acid linker are performed using an OBOC library of the form H$_2$N-(D-Pra)-xxxxx-Cy(R$_6$R$_7$R$_8$R$_9$R$_{10}$-click)-Met-TG (SEQ ID NO: 48), where TG=TentaGel® S NH$_2$ resin (S 30 902, Rapp Polymere), x=one of seven D-amino acids (Gly, D-Ala, D-Leu, D-Pro, D-Ser, D-Thr, Aib) or no amino acid, and Cy(R$_6$R$_7$R$_8$R$_9$R$_{10}$-click)=Epi1N PCC=macrocycles selected from AKYRG (SEQ ID NO: 8), wplif (SEQ ID NO: 13), ffrly (SEQ ID NO: 17), or rwfnv (SEQ ID NO: 14). The diversity of this library is 85=32,768 linkers for each Epi1N PCC. Separately, Biotin-PEG$_3$-Cy(R$_1$R$_2$R$_3$R$_4$R$_5$-click)-Az4 was synthesized and a stock solution was made, where Cy(R$_1$R$_2$R$_3$R$_4$R$_5$-click)=Epi2C PCC=macrocycles selected from HGRGH (SEQ ID NO: 21) and wsvnv (SEQ ID NO: 34). Amino acid linkers were found by screening the library against CD8α human recombinant protein and Epi2C PCC in two steps: 1) a pre-clear to eliminate non-specific background binders, 2) an in situ click screen, promoted by the CD8α protein, to identify a linear peptide (0 to 5 D-amino acids in length) that connects the two macrocycles Epi2C PCC and Epi1N PCC.

Pre-clear. Swelled linker library beads (40 mg; ~3.5× oversampled) were blocked overnight with Blocking Buffer (25 mM Tris-HCl, 150 mM NaCl, 1% (w/v) BSA, and 0.05% (v/v) Tween-20, pH 7.6) at 4° C., then washed with Blocking Buffer three times. Beads were then incubated with 4 mL of 100 µM Biotin-PEG$_3$-Cy(R$_1$R$_2$R$_3$R$_4$R$_5$-click)-Az4 (Epi2C PCC) and a 1:10,000 dilution of Streptavidin-Alkaline Phosphatase (V559C, Promega) in Blocking Buffer for 3 h at room temperature. The beads were subsequently washed with 3×3 mL TBS (25 mM Tris-HCl, 150 mM NaCl, pH 7.6) (1 min ea), 3×3 mL 0.1 M glycine pH 2.8 wash buffer, 3×3 mL TBS, then 3×3 mL Alkaline Phosphatase buffer (100 mM Tris-HCl, 150 mM NaCl, 1 mM MgCl$_2$, pH 9) (5 min ea). Binding was visualized by incubating the beads in the presence of 5-bromo-4-chloro-3-indolyl phosphate/nitro blue tetrazolium (BCIP/NBT) substrate (S3771, Promega) for 25 min. Purple beads indicated background binders and were removed by pipet and discarded. The remaining clear beads were collected and stripped with 7.5 M guanidine hydrochloride pH 2.0 for 30 min, washed ten times with water, and incubated in NMP overnight to decolorize.

In situ Click Screen with CD8α Protein. Beads remaining from the pre-clear were washed with water ten times and TBS three times. Beads were then incubated with 4 mL of 100 µM Biotin-PEG$_3$-Cy(R$_1$R$_2$R$_3$R$_4$R$_5$-click)-Az4 (Epi2C PCC) and 150 nM His-tagged CD8α human recombinant protein (TP760215, Origene) in Blocking Buffer for 3 h at room temperature to allow for a protein-templated in situ click reaction to occur. The beads were washed with TBS ten times and then incubated with 7.5 M guanidine hydrochloride pH 2.0 for 1 h to remove all Epi2C PCC and CD8α protein not attached covalently to the beads. These beads were washed with TBS ten times and re-blocked with Blocking Buffer for 2 h. A 1:10,000 dilution of Streptavidin-Alkaline Phosphatase in 4 mL Blocking Buffer was added for 1 h to detect the presence of Epi2C PCC clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple hit beads containing the two conjugated macrocycles were selected by pipet. The hits were treated with 7.5 M guanidine hydrochloride pH 2.0 for 30 min to remove attached streptavidin, washed ten times with water, and incubated in NMP overnight to decolorize.

The sequences of the linear D-amino acid linker (xxxxx) on hit beads were determined after CNBr cleavage and MALDI-MS and MS/MS analysis. These biligand candidates were re-synthesized on a cleavable resin, purified by reversed phase HPLC using a $C_{18}$ column (Phenomenex Luna, 5 μm, 250×10 mm), and tested for cooperative binding to the human CD8α protein by ELISA.

Example 13: Synthesis of Cooperative Biligands

To synthesize the first set of cooperative biligands, we conjoined macrocycles Cy(HGRGH) (SEQ ID NO: 21) from CD8 Epitope2C and Cy(wplrf) (SEQ ID NO: 13) from CD8 Epitope1N. The synthesis started with preparing Cy(wplrf) (SEQ ID NO: 13) on Rink amide resin using conventional Fmoc-based solid phase peptide synthesis (SPPS). The peptide was cyclized between the N-terminal Pra and C-terminal Az4 using copper (I) iodide (1.5 equiv) and ascorbic acid (5 equiv) in 4:1 NMP: piperidine. On the next day, the residual copper bound to the resin was removed by shaking the resin with NMP containing 5% (w/v) sodium diethyldithiocarbamate trihydrate and 5% (v/v) N,N-diisopropylethylamine for 5 min. PEG linkers of various lengths ($PEG_3$, $PEG_4$, $PEG_5$, $PEG_6$, and $PEG_7$) were then coupled onto the resins. $PEG_3$, $PEG_4$, and $PEG_5$ were made from Fmoc-NH-$PEG_3$-$CH_2COOH$ (280103), Fmoc-NH-$PEG_4$-$CH_2COOH$ (280117), and Fmoc-NH-$PEG_5$-$CH_2COOH$ (280104) obtained from ChemPep. Two successive couplings of Fmoc-NH-$PEG_3$-$CH_2COOH$ yielded $PEG_6$. Coupling of Fmoc-NH-$PEG_4$-$CH_2COOH$ and Fmoc-NH-$PEG_3$-$CH_2COOH$ yielded $PEG_7$. After coupling the PEG linkers, the resins were returned to the AAPPTEC Titan 357 instrument to synthesize the remainder of the biligands. A second cyclization resulted in the Cy(HGRGH) (SEQ ID NO: 21) portion of each biligand. The residual copper was again removed by chelation. Biligands were then cleaved from the resin for 4 h with 92.5% TFA, 2.5% H2O, 2.5% TIS (triisopropylsilane), and 2.5% DODT (3,6-dioxa-1,8-octanedithiol), and then purified by reversed phase HPLC using a $C_{18}$ column.

The same strategy was employed to construct another set of biligands comprised of Cy(HGRGH) (SEQ ID NO: 21) from CD8 Epitope2C and Cy(AKYRG) (SEQ ID NO: 8) from CD8 Epitope1N.

Example 14: Assays to Determine Cooperativity

CD8 ELISA (Affinity assay). Protocol: A black 96-well NeutrAvidin Coated High Binding Capacity plate (15510, Pierce) was coated with 150 to 250 nM biotin-$PEG_3$-modified biligand in TBS (25 mM Tris-HCl, 150 mM NaCl, pH 7.6) for 2 h at room temperature. The plate was aspirated and then washed with TBS. The plate was then blocked with 2 μM Biotin for 15 min. Then, the plate was washed with TBS and/or Wash Buffer (0.05% (v/v) Tween-20 in PBS). His-tagged CD8α human recombinant protein (MBS968456, MyBioSource) was serially diluted in Wash Buffer (from 200 to 0 nM) and incubated in the designated microwells for 90 min at room temperature. Microwells were aspirated and subsequently washed with Wash Buffer (10×). To detect the bound CD8α protein, Alkaline Phosphatase (AP)-conjugated Anti-6× His Tag® antibody [HIS-1] (ab49746, Abcam) was prepared at 1:10,000 dilution and added to the microwells for 1 h at room temperature. The plate was aspirated and washed with Wash Buffer (5×). AttoPhos® AP Fluorescent Substrate System (S1000, Promega) was employed for development. Using an excitation wavelength of 430 nm, fluorescent emission at 535 nm was recorded. Titration curves were fit using a four-parameter regression curve fitting program (Origin 8.5) to determine $EC_{50}$ values.

Figure 17:
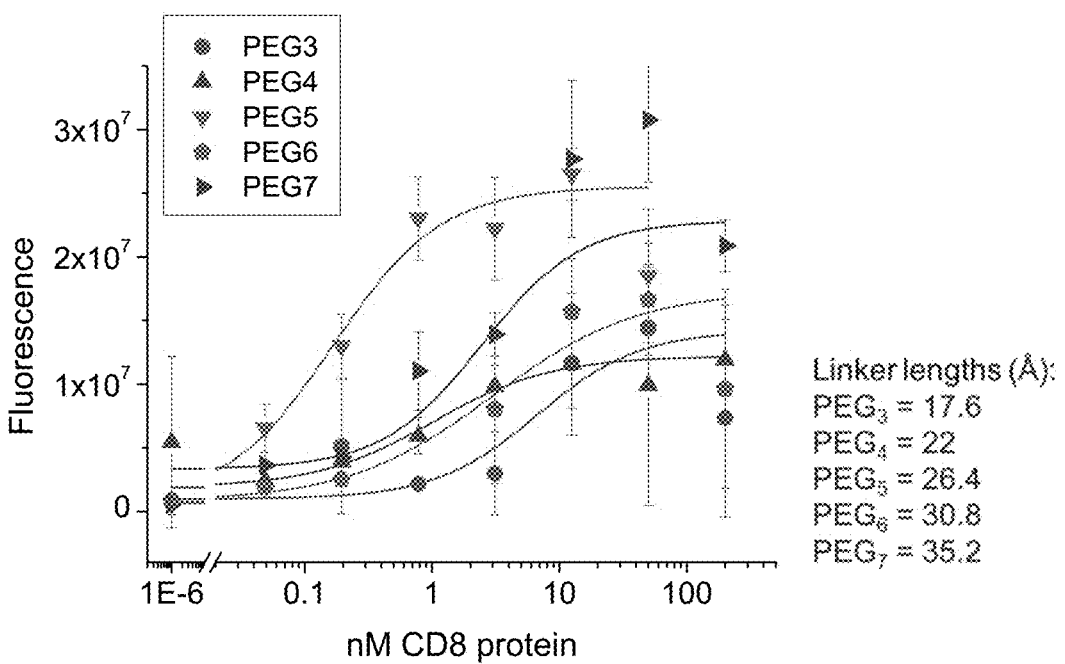
FIG. 17 shows PCC biligands that specifically bind CD8 that exploit cooperativity. The sandwich ELISA for human CD8α protein against biotin-$PEG_3$-modified biligands demonstrates that a linker of length closest to 28.2 Å ($PEG_5$) yields the best binder (by ~10-fold). Biligands are of the form Biotin-$PEG_3$-Cy(HGRGH) (SEQ ID NO: 21)-$PEG_x$-Cy(wplrf) (SEQ ID NO: 13) (x=3 to 7). Biotin-$PEG_3$-Cy (HGRGH) (SEQ ID NO: 21)-$PEG_5$-Cy(wplrf) (SEQ ID NO: 13) exhibits an $EC_{50}$ value of 200 pM against CD8 which represents a >30-fold improvement in affinity relative to the individual PCC macrocyclic ligands.

By analysis of the CD8α crystal structure, FIG. 14 shows that the distance between the CD8 Epitope2C and CD8 Epitope1N is an estimated 28.2 Å. This predicts that an optimized linker to covalently join two PCC macrocycles will have a length near 28.2 Å. In FIG. 17 that prediction is validated by testing polyethylene glycol (PEG) linkers of varying lengths. When the macrocycles Cy(HGRGH) (SEQ ID NO: 21) and Cy(wplrf) (SEQ ID NO: 13) are covalently linked to each other by using the PEG linker of length closest to 28.2 Å, the resultant biligand (PEGS) exhibits an $EC_{50}$ value of 200 pM against CD8. This represents a >30-fold improvement in affinity relative to the individual PCC macrocyclic ligands. Shorter or longer linkers yield biligand affinities that, while improved over either of the PCC macrocycles, are about ~10-fold below that of the optimal linker.

Structures of the biligand candidates Biotin-$PEG_3$-Cy(HGRGH) (SEQ ID NO: 21)-$PEG_x$-Cy(wplrf) (SEQ ID NO: 13) (x=3 to 7) are shown in Table 7.

Example 15: Structures and Characterization of CD8 Biligands

TABLE 7

CD8 Biligands

36

Chemical Formula: $C_{107}H_{158}N_{36}O_{24}S$
Exact Mass: 2363.20
Molecular Weight: 2364.69

Biotin-PEG$_3$—Cy(HGRGH) (SEQ ID NO: 21)-PEG$_3$—Cy(wplrf) (SEQ ID NO: 13). Chemical Formula: $C_{107}H_{158}N_{36}O_{24}S$; Exact Mass: 2363.20; Molecular Weight: 2364.69.

37

Chemical Formula: $C_{109}H_{162}N_{36}O_{25}S$
Exact Mass: 2407.22
Molecular Weight: 2408.74

Biotin-PEG$_3$—Cy(HGRGH) (SEQ ID NO: 21)-PEG$_4$—Cy(wplrf) (SEQ ID NO: 13). Chemical Formula: $C_{109}H_{162}N_{36}O_{25}S$; Exact Mass: 2407.22; Molecular Weight: 2408.74.

TABLE 7-continued

CD8 Biligands

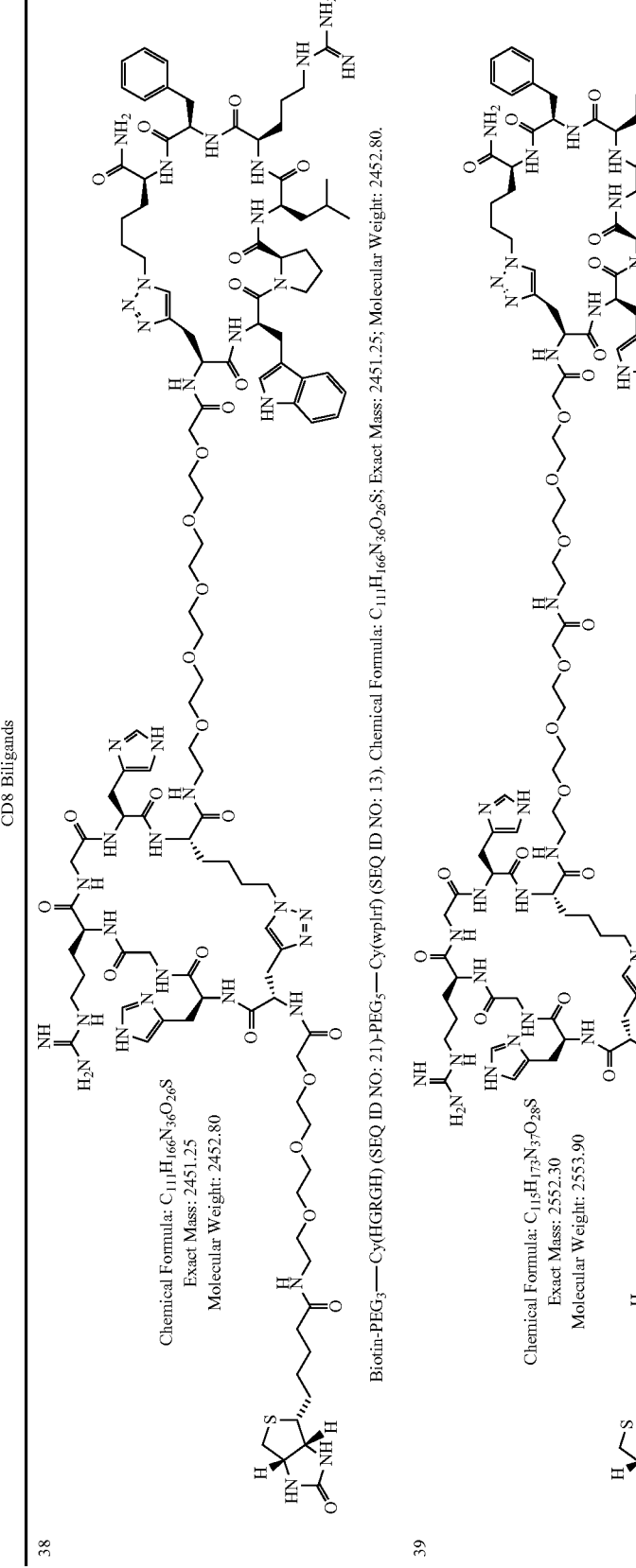

38

Chemical Formula: $C_{111}H_{166}N_{36}O_{26}S$
Exact Mass: 2451.25
Molecular Weight: 2452.80

Biotin-PEG$_3$—Cy(HGRGH) (SEQ ID NO: 21)-PEG$_5$—Cy(wplrf) (SEQ ID NO: 13). Chemical Formula: $C_{111}H_{166}N_{36}O_{26}S$; Exact Mass: 2451.25; Molecular Weight: 2452.80.

39

Chemical Formula: $C_{115}H_{173}N_{37}O_{28}S$
Exact Mass: 2552.30
Molecular Weight: 2553.90

Biotin-PEG$_3$—Cy(HGRGH) (SEQ ID NO: 21)-PEG$_6$—Cy(wplrf) (SEQ ID NO: 13). Chemical Formula: $C_{115}H_{173}N_{37}O_{28}S$; Exact Mass: 2552.30; Molecular Weight: 2553.90.
Note that PEG$_6$ was formed by coupling PEG$_3$ to the peptide twice in series.

TABLE 7-continued

CD8 Biligands

Chemical Formula: $C_{117}H_{177}N_{37}O_{29}S$
Exact Mass: 2596.32
Molecular Weight: 2597.95

Biotin-PEG$_3$—Cy(HGRGH) (SEQ ID NO: 21)-PEG$_7$—Cy(wplrf) (SEQ ID NO: 13). Chemical Formula: $C_{117}H_{177}N_{37}O_{29}S$; Exact Mass: 2596.32; Molecular Weight: 2597.95.
Note that PEG$_7$ was formed by coupling PEG$_4$ and then PEG$_3$ to the peptide.

Chemical Formula: $C_{100}H_{158}N_{36}O_{27}S$
Exact Mass: 2327.18
Molecular Weight: 2328.61

Biotin-PEG$_3$—Cy(HGRGH) (SEQ ID NO: 21)-PEG$_5$—Cy(AKYRG) (SEQ ID NO: 8). Chemical Formula: $C_{100}H_{158}N_{36}O_{27}S$; Exact Mass: 2327.18; Molecular Weight: 2328.61.

40

41

TABLE 7-continued

CD8 Biligands

42

Chemical Formula: C_{104}H_{165}N_{37}O_{29}S
Exact Mass: 2428.23
Molecular Weight: 2429.72

Biotin-PEG_3—Cy(HGRGH) (SEQ ID NO: 21)-PEG_6—Cy(AKYRG) (SEQ ID NO: 8). Chemical Formula: C_{104}H_{165}N_{37}O_{29}S; Exact Mass: 2428.23; Molecular Weight: 2429.72.
Note that PEG_6 was formed by coupling PEG_3 to the peptide twice in series.

Figure 18:
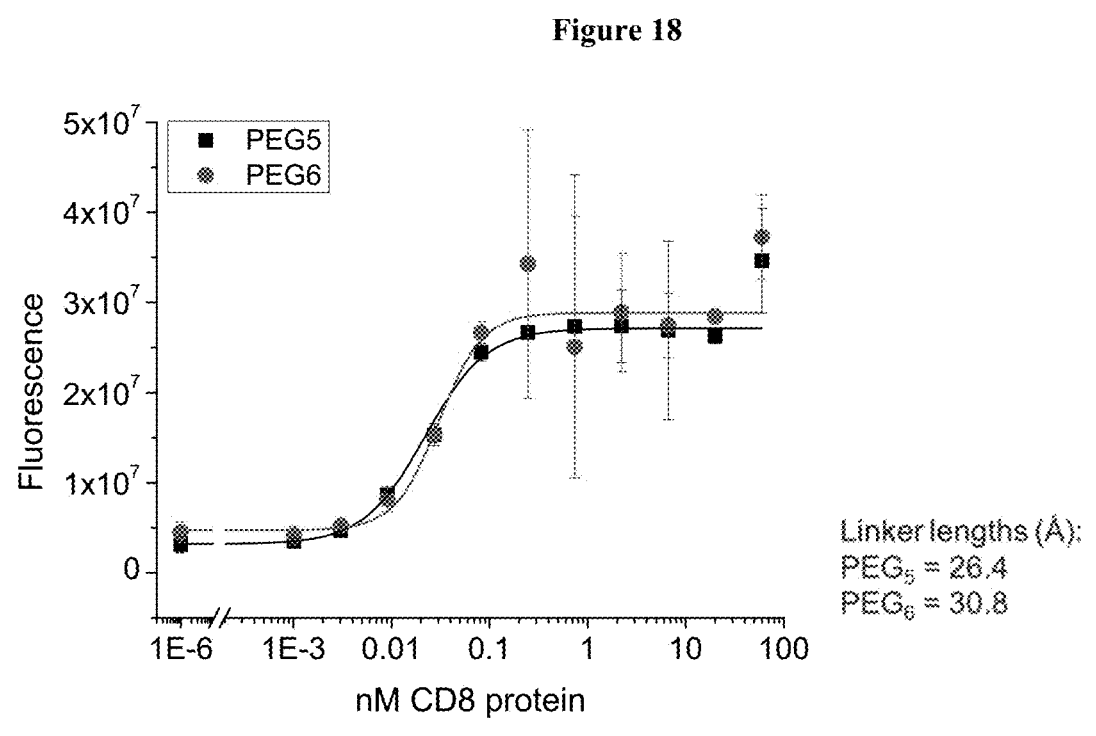

In FIG. 18, this concept is further validated by testing additional biligands in which the macrocycles Cy(HGRGH) (SEQ ID NO: 21) and Cy(AKYRG) (SEQ ID NO: 8) are covalently linked to each other. Biligands were made with PEG$_5$ and PEG$_6$ because their lengths are most similar to the 28.2 Å distance between CD8 Epitope2C and CD8 Epitope1N. These biligands exhibited EC$_{50}$ values of 25 pM against CD8, representing a >200-fold improvement in affinity relative to the individual PCC macrocyclic ligands.

Structures of the biligand candidates Biotin-PEG$_3$-Cy (HGRGH) (SEQ ID NO: 21)-PEG$_x$-Cy(AKYRG) (SEQ ID NO: 8) (x=5 to 6) are shown in Table 7.

The enhanced binding effect displayed by Biotin-PEG$_3$-Cy(HGRGH) (SEQ ID NO: 21)-PEG$_5$-Cy(wplrf) (SEQ ID NO: 13) in FIG. 17 and Biotin-PEG$_3$-Cy(HGRGH) (SEQ ID NO: 21)-PEG$_5$-Cy(AKYRG) (SEQ ID NO: 8) and Biotin-PEG$_3$-Cy(HGRGH) (SEQ ID NO: 21)-PEG$_6$-Cy(AKYRG) (SEQ ID NO: 8) in FIG. 18 is called binding cooperativity. Because CD8α has a known and well-defined 3D protein structure, PCC macrocyclic ligands were able to be developed separately against two different regions of the protein. With appropriately designed PEG linkers, two ligands were then chemically linked together to form biligands with picomolar (pM=10$^{-12}$ M) affinity for the target. In other words, these biligands exhibited binding affinities that are far superior to either of the individual ligands.

Example 16: Synthesis of Additional Biligands

The aforementioned strategy was employed to synthesize additional biligands comprised of:

Cy(PWTHG) (SEQ ID NO: 25) from CD8 Epitope2N and Cy(AKYRG) (SEQ ID NO: 8) from CD8 Epitope1N Cy(Ghtwp) (SEQ ID NO: 41) from CD8 Epitope2N and Cy(hGrGh) (SEQ ID NO: 49) from CD8 Epitope2C (targeting the N- and C-terminal sides of a single loop epitope of human CD8)

The biligands against the single loop epitope were created using the retro-inverso analogues of each macrocycle in order to install D-amino acids that would be more stable to protease digestion. The retro-inverso approach was found to retain most affinity and selectivity attributes while improving the stability.

Biligands were tested for affinity towards His-tagged CD8α human recombinant protein. Picomolar binders were obtained from each family of biligands (FIG. 19). The enhanced binding effect displayed by these biligands is called binding cooperativity.

Example 17: Cellular Binding Assay of CD8 Biligand

Cryopreserved human peripheral blood mononuclear cells (PBMCs) from Zen-Bio (1 donor; #SER-PBMC-F) were thawed using Lymphocyte Medium (#LYMPH-1, Zen-Bio) following the vendor's protocol. Cells were then resuspended in FACS buffer (1× Dulbecco's Phosphate-Buffered Saline+2% Fetal Bovine Serum+2 mM EDTA).

Protocol: A total of 1×10$^6$ human PBMCs in 50 μL of FACs buffer was incubated with 0.5 μL of Alexa Fluor 488-labeled biligand Cy(HGRGH) (SEQ ID NO: 21)-PEG$_5$-Cy(AKYRG) (SEQ ID NO: 8) (final concentration: 5 μM), 2 μL of human CD3-APC mAb (clone: BW264/56) (#130-098-156, MACS Miltenyi Biotec), and 2.5 μL of 7-AAD Viability Staining Solution (#00-6993, eBioscience) at room temperature for 30 min. As a control, another sample of 1×10$^6$ human PBMCs in 50 μL of FACs buffer was incubated with 20 μL of human CD8-FITC mAb (clone: RPA-T8) (#561947, BD Biosciences), 2 μL of human CD3-APC mAb (clone: BW264/56), and 2.5 μL of 7-AAD Viability Staining Solution at room temperature for 30 min. After one wash with FACS buffer, flow cytometry analysis was performed using a BD LSR Fortessa X-20 cytometer. Data were obtained and analyzed with FACSCalibur and FACSDiva v8.0.1 (BD Biosciences), respectively.

Flow cytometry was used to evaluate biligand detection of cellular CD8. The biligand Cy(HGRGH) (SEQ ID NO: 21)-PEG$_5$-Cy(AKYRG) (SEQ ID NO: 8), which exhibited an EC$_{50}$ value of 25 pM against recombinant human CD8α protein, was resynthesized with an Alexa Fluor 488 label (FIG. 20A). Human PBMCs were stained with CD3-APC mAb (a pan T cell marker) and Alexa Fluor 488-labeled biligand Cy(HGRGH) (SEQ ID NO: 21)-PEG$_5$-Cy (AKYRG) (SEQ ID NO: 8) (FIG. 20B). Samples were then washed and analyzed for green (CD8; FITC-A) and red (CD3; APC-A) fluorescence. 7-AAD was used to exclude nonviable cells from the flow cytometric analysis. The cell populations in Q2 (10.9%) and Q4 (11.6%) were detected by the biligand as CD8+ and are consistent with the % CD8+ cells reported by the vendor. As a control, another sample of human PBMCs was stained with CD3-APC mAb and a commercial FITC-labeled CD8 mAb (FIG. 20C). The cell populations detected by the CD8-FITC mAb were 11.2% in Q2 and 2.1% in Q4.

Example 18: Structures and Characterization of Additional CD8 Biligands

TABLE 8

CD8 Biligands

Chemical Formula: $C_{90}H_{128}N_{36}O_{19}S$
Exact Mass: 2048.99
Molecular Weight: 2050.27

Cy(Ghtwp) (SEQ ID NO: 41)-Lys(Biotin)-Gly-Cy(hGrGh)(SEQ ID NO: 49). Chemical Formula: $C_{90}H_{128}N_{36}O_{19}S$; Exact Mass: 2048.99; Molecular Weight: 2050.27.

43

TABLE 8-continued
CD8 Biligands
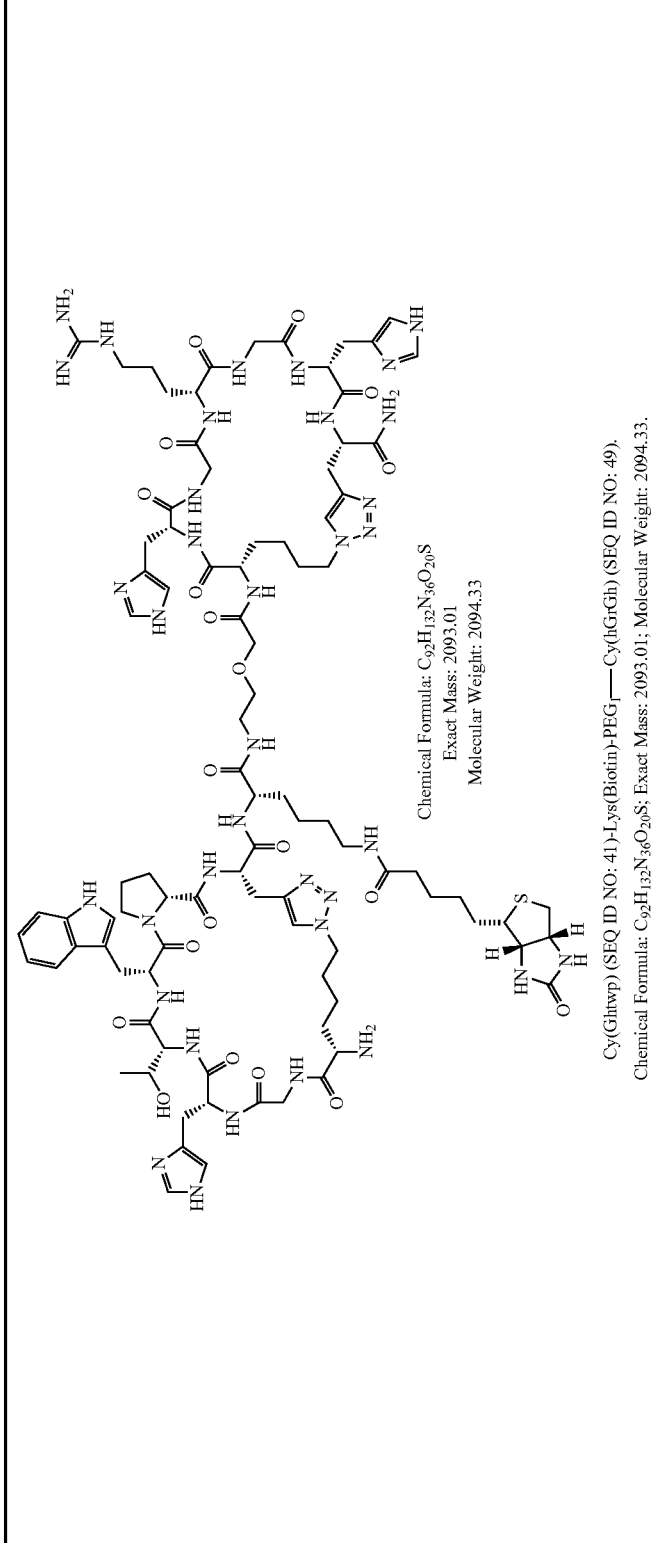
Chemical Formula: $C_{92}H_{132}N_{36}O_{20}S$
Exact Mass: 2093.01
Molecular Weight: 2094.33
Cy(Ghtwp) (SEQ ID NO: 41)-Lys(Biotin)-PEG$_1$——Cy(hGrGh) (SEQ ID NO: 49).
Chemical Formula: $C_{92}H_{132}N_{36}O_{20}S$; Exact Mass: 2093.01; Molecular Weight: 2094.33.
44

US 12,594,350 B2
83
84
TABLE 8-continued
CD8 Biligands
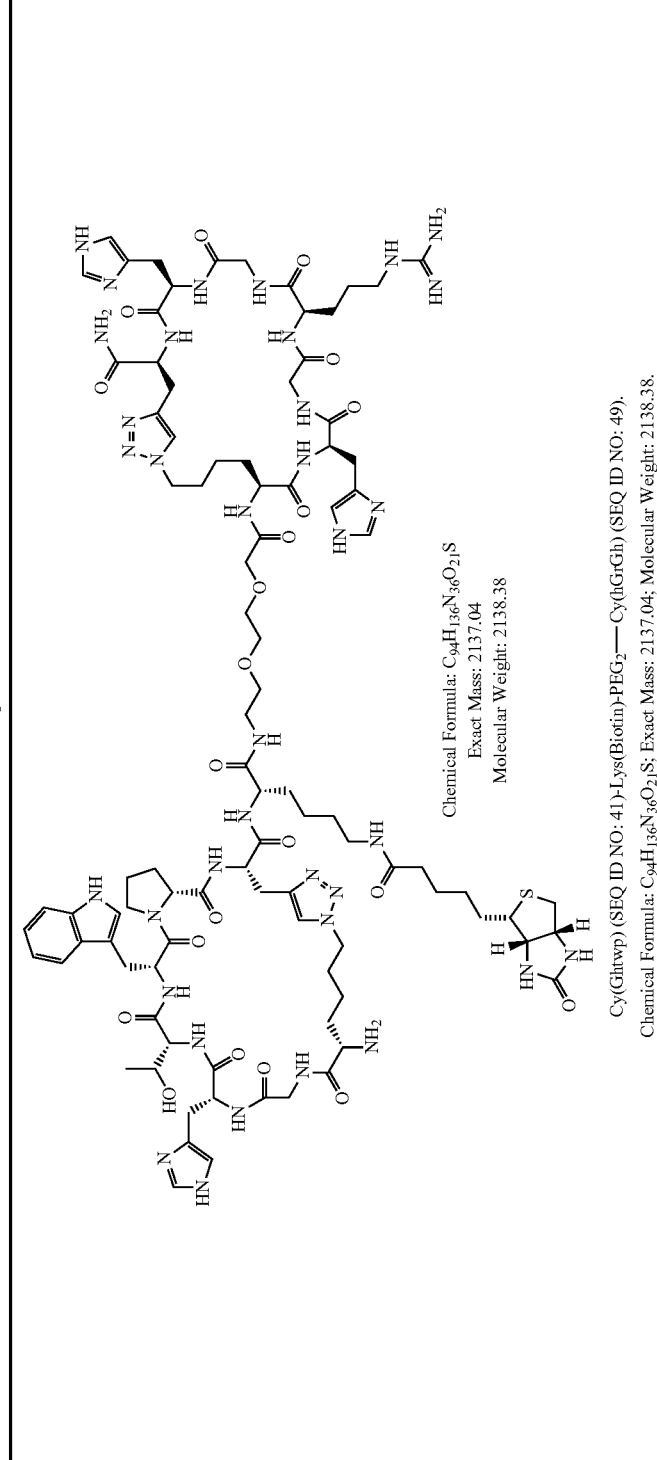
Chemical Formula: $C_{94}H_{136}N_{36}O_{21}S$
Exact Mass: 2137.04
Molecular Weight: 2138.38
Cy(Glhtwp) (SEQ ID NO: 41)-Lys(Biotin)-PEG$_2$—Cy(thGrGh) (SEQ ID NO: 49).
Chemical Formula: $C_{94}H_{136}N_{36}O_{21}S$; Exact Mass: 2137.04; Molecular Weight: 2138.38.
45

TABLE 8-continued

CD8 Biligands

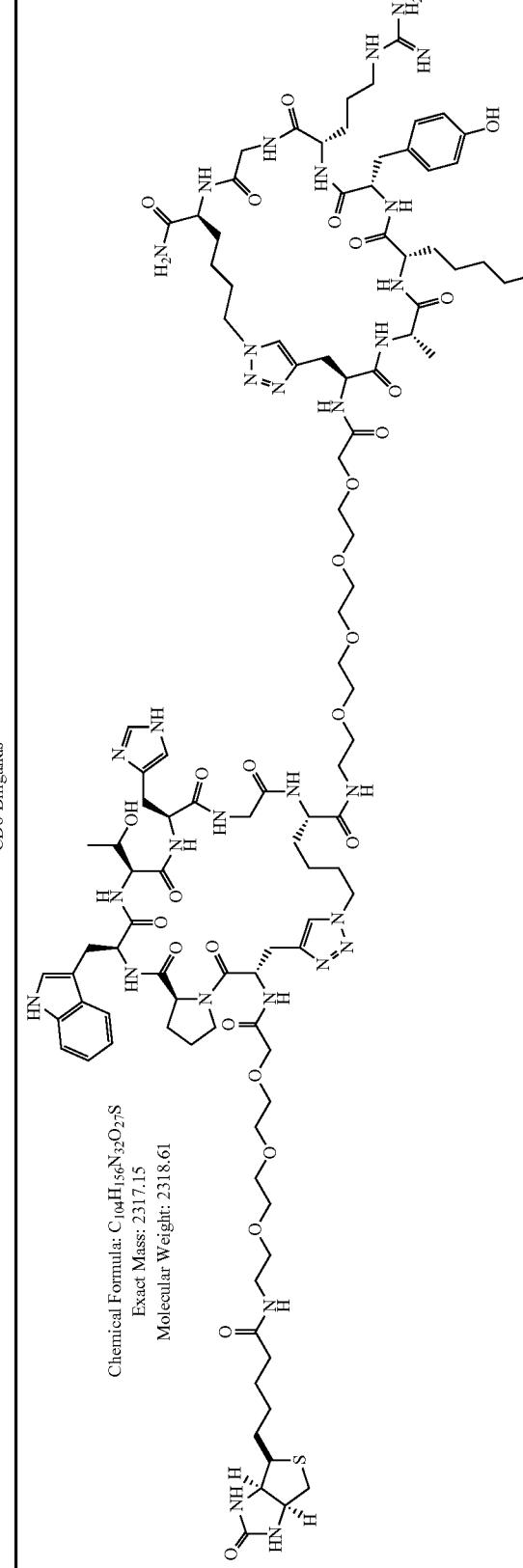

46    Chemical Formula: C₁₀₄H₁₅₆N₃₂O₂₇S
Exact Mass: 2317.15
Molecular Weight: 2318.61

Biotin-PEG₃—Cy(PWTHG) (SEQ ID NO: 25)-PEG₄—Cy(AKYRG) (SEQ ID NO: 8). Chemical Formula: C₁₀₄H₁₅₆N₃₂O₂₇S; Exact Mass: 2317.15; Molecular Weight: 2318.61.

47    Chemical Formula: C₁₀₆H₁₆₀N₃₂O₂₈S
Exact Mass: 2361.18
Molecular Weight: 2362.67

Biotin-PEG₃—Cy(PWTHG) (SEQ ID NO: 25)-PEG₅—Cy(AKYRG) (SEQ ID NO: 8). Chemical Formula: C₁₀₆H₁₆₀N₃₂O₂₈S; Exact Mass: 2361.18; Molecular Weight: 2362.67.

TABLE 8-continued

CD8 Biligands

48

Chemical Formula: $C_{110}H_{167}N_{33}O_{30}S$
Exact Mass: 2462.23
Molecular Weight: 2463.77

Biotin-PEG$_3$——Cy(PWTHG) (SEQ ID NO: 25)-PEG$_6$——Cy(AKYRG) (SEQ ID NO: 8). Chemical Formula: $C_{110}H_{167}N_{33}O_{30}S$; Exact Mass: 2462.23; Molecular Weight: 2463.77.
Note that PEG$_6$ was formed by coupling PEG$_3$ to the peptide twice in series.

Example 19: Species Cross-Reactivity Analysis

Figure 21:
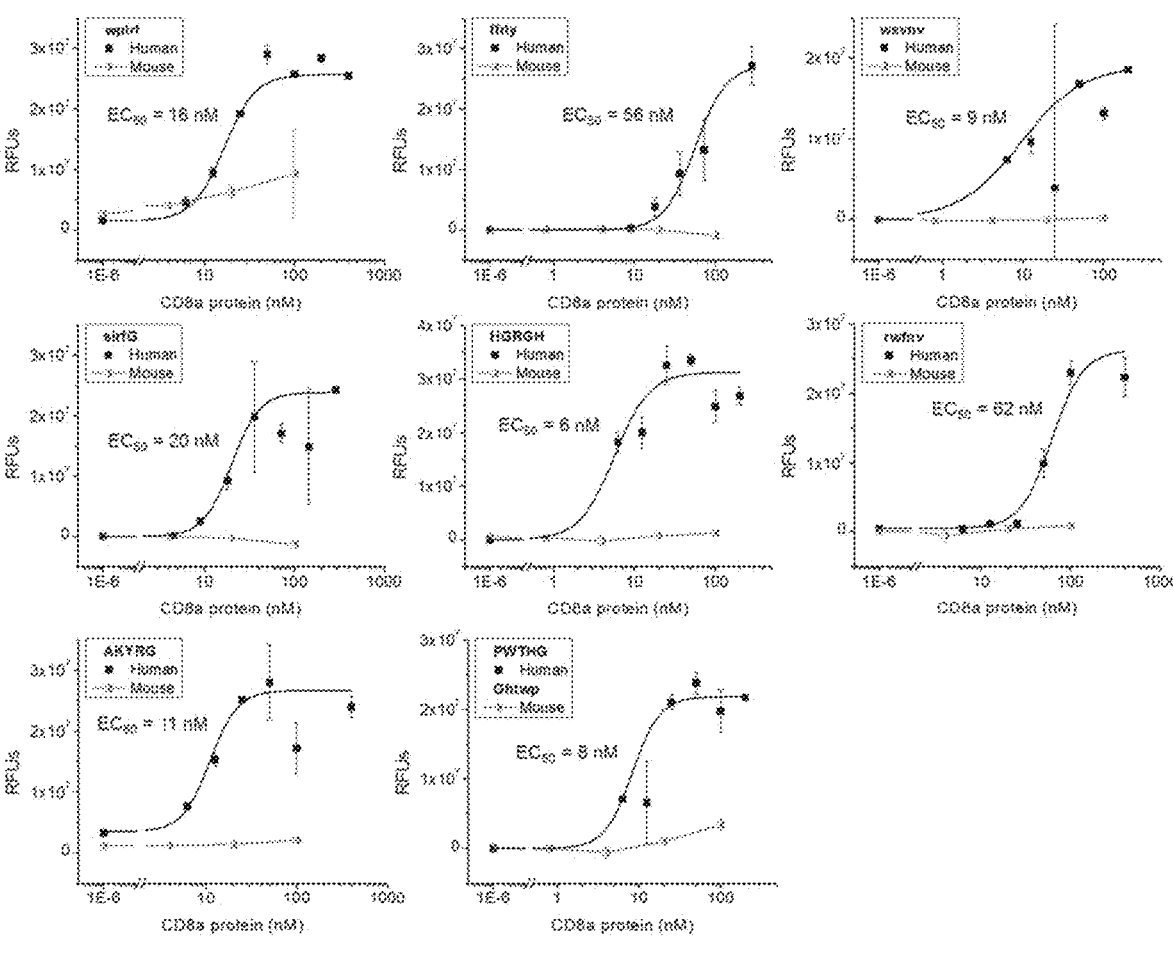
FIG. 21 shows the binding affinities of anti-human CD8α macrocycle anchors against human (black) and murine (grey) CD8α proteins, as measured by ELISA.

To test for potential cross-reactivity with murine CD8a, the human CD8α targeted macrocycle anchors were assayed against the murine CD8α proteins by ELISA. FIG. 21 shows curves from the ELISA titrations of human and murine CD8α proteins against the immobilized macrocycles. The anti-human CD8α macrocycle anchors showed high selectivity for the human protein and weak binding to the murine protein. The high species selectivity appears to have resulted from Chemical Epitope Targeting, the method used for developing the macrocycles against a specific region of the human CD8 protein (the epitope).

Fluorine-18 positron emission tomography (PET) was used to study in vivo pharmacokinetics (PK) and organ biodistribution of macrocycle anchors and biligands.

Example 20: Fluorine-18 Radiochemistry

Each aminooxy-PCC was synthesized on Rink amide resin using Fmoc solid-phase peptide synthesis. The aminooxy group was incorporated at the N-terminus of the peptide-resin by coupling Boc-Aminooxyacetic acid (AK Scientific, cat #66435). Resin cleavage and deprotection of the side chains were achieved by treatment with TFA: H2O: TIS: DODT (92.5:2.5:2.5:2.5). The aminooxy-PCC was then purified by C18 HPLC, and its mass was confirmed by MALDI-MS before entering into the labeling reaction.

Conjugation of aminooxy-PCC with 4-fluorobenzaldehyde. The 19F-fluorobenzaldehyde oxime was prepared by reacting the aminooxy-PCC (1 equiv) with 4-fluorobenzaldehyde (1 equiv; AK Scientific, cat #268112) for 20 min at 80° C. in 100 mM Ammonium Formate pH 4.0 Buffer/Methanol (2:1) (reaction volume=1.5 mL). The reaction mixture was subjected to $C_{18}$ HPLC to isolate the pure $^{19}F$-fluorobenzaldehyde oxime, and its mass was confirmed by MALDI-MS. Two oxime isomers (E/Z) were observed and typically collected as the non-radioactive ("cold") standard.

Figure 22:
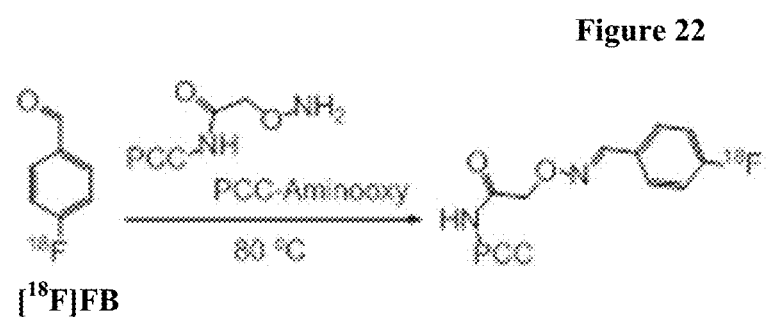

Conjugation of aminooxy-PCC with 4-[$^{18}F$]fluorobenzaldehyde ([$^{18}F$]FB). The $^{18}F$-labeling of macrocycle anchors and biligands was achieved through condensation of [$^{18}F$]FB with aminooxy-PCC using the ELIXYS automated radiosynthesizer. For this reaction (FIG. 22), [$^{18}F$]FB was the limiting reagent and the aminooxy-PCC was added in excess (5-10 mg). Otherwise, the reaction conditions were the same as above. The radiolabeled PCC was purified from the reaction mixture by $C_{18}$ HPLC and then co-injected with "cold" 19F-fluorobenzaldehyde oxime to confirm its identity.

For the production of [$^{18}F$]FB and subsequent PCC labeling, the overall decay-corrected radiochemical yields ranged from 1-10%. Synthesis time ranged from 100-130 minutes, including HPLC purification and formulation for injection.

Example 21: In Vivo Pet Imaging Data

In vivo PK of the radiolabeled macrocycle anchors and biligands was visualized and quantitatively determined by PET imaging in normal (healthy) mice. Radiolabeled peptides were formulated in PBS pH 7.4 containing <10% EtOH. 50-100 μCi of radiolabeled peptide was administered intravenously via the tail vein of each mouse. Dynamic (0-1 hour) and static PET imaging was performed to quantify initial peptide biodistribution, time to clear the initial concentration sites, and final excretion route. A CT scan was subsequently acquired for anatomical reference. Imaging was performed on GENISYS8 and Inveon microPET-CT small animal scanners.

The biodistribution profiles in mice of three macrocycle anchors were determined by PET. In a normal (healthy) mouse, [$^{18}F$]FB-labeled Cy(AKYRG) (SEQ ID NO: 8) (FIG. 23) showed kidney clearance to the bladder (on the order of one hour) with little liver activity. By 2 hours post-injection, the peptide is mostly in the bladder. Because human and murine CD8 share only 40% amino acid sequence homology in their extracellular domains, there is not significant binding to murine CD8; thus, these images provided a means of assessing clearance, not targeting, in mice.

The biodistribution of [$^{18}F$]FB-labeled Cy(HGRGH) (SEQ ID NO: 21) (FIG. 24) in a normal (healthy) mouse was similar, with kidney clearance to the bladder (on the order of one hour) with little liver activity. There is a small amount of activity in the intestine at 1-2 hours for this macrocycle anchor.

The biodistribution of [$^{18}F$]FB-labeled Cy(wplrf) (SEQ ID NO: 13) (FIG. 25) in a normal (healthy) mouse was characterized by predominantly liver and intestinal uptake with some clearance to the bladder at 2 hours post-injection. The hepatobiliary clearance of this macrocycle anchor appears to be influenced by its relative hydrophobicity.

As a control, microPET-CT images were obtained from normal (healthy) mice administered with [$^{18}F$]FB. The images (FIG. 26) showed rapid kidney uptake and clearance, then near exclusive bladder occupancy by 30 minutes. If the oxime bond in the radiolabeled macrocycle anchors were to hydrolyze in vivo, [$^{18}F$]FB would be liberated and yield this biodistribution profile. Because the macrocycle anchors showed different biodistribution profiles, it suggests that the oxime bond remained intact during scanning and the observed biodistribution was contributed mainly by the peptide.

The biodistribution profile in mice of one biligand was determined by PET. In a normal (healthy) mouse, [$^{18}F$]FB-labeled Cy(HGRGH) (SEQ ID NO: 21)-PEG$_5$-Cy(wplrf) (SEQ ID NO: 13) (FIG. 27) shows a biodistribution that reflects contributions from both constituent macrocycle anchors, with clearance via the kidneys (predominantly) and liver.

The invention claimed is:

1. A method of producing a synthetic capture agent that specifically binds to CD8 comprising (a) selecting a first ligand that binds to a first synthetic epitope of CD8 by screening a peptide library for epitope-templated in situ click reaction of the first synthetic epitope and a peptide in the peptide library that comprises a proparglyglycine;

(b) selecting a second ligand that binds to a second synthetic epitope of CD8 by screening a peptide library for epitope-templated in situ click reaction of the second synthetic epitope and a peptide in the peptide library that comprises a proparglyglycine; and (c) covalently joining a linker to the first ligand and the second ligand, thereby producing the synthetic capture agent that binds to CD8, wherein the first synthetic epitope comprises the sequence SQFRVSPLD[Az4]TWNLGETVELKSQ (SEQ ID NO: 54) and the second synthetic epitope comprises the sequence FLLYLSQNKP[Az4]AAE-GLDTQR (SEQ ID NO: 55).

2. The method of claim 1, wherein the length of the linker is the distance between a first native epitope of CD8 bound by the first ligand and a second native epitope of CD8 bound by the second ligand.

3. The method of claim 1, wherein the length of the linker is from 4.4 Å to 39.6 Å.

4. The method of claim 3, wherein the length of the linker is from 26.4 Å to 39.6 Å.

5. The method of claim 4, wherein the length of the linker is 28.2 Å.

6. The method of claim 1, wherein the linker comprises one or more repeat units of ethylene glycol.

7. The method of claim 6, wherein the linker comprises $PEG_1$, $PEG_2$, $PEG_3$, $PEG_4$, $PEG_5$, $PEG_6$, $PEG_7$, or $PEG_8$.

8. The method of claim 1, wherein the linker comprises an amino acid or a peptide.

9. A synthetic capture agent that binds to CD8, wherein the synthetic capture agent comprises a first ligand that is cyclic and 5-9 amino acids in length having affinity for a first epitope on CD8, a second ligand that is cyclic and 5-9 amino acids in length having affinity for a second epitope on CD8, and a linker covalently connecting the first ligand to the second ligand, wherein the first ligand comprises an amino acid sequence chosen from:

```
(a)
                                            (SEQ ID NO: 6)
HGSYG;

(b)
                                            (SEQ ID NO: 7)
KRLGA;

(c)
                                            (SEQ ID NO: 8)
AKYRG;

(d)
                                            (SEQ ID NO: 9)
hallw;

(e)
                                            (SEQ ID NO: 10)
lrGvw;

(f)
                                            (SEQ ID NO: 11)
vashf;

(g)
                                            (SEQ ID NO: 12)
nGnvh;

(h)
                                            (SEQ ID NO: 13)
wplrf;

(i)
                                            (SEQ ID NO: 14)
rwfnv;

(j)
                                            (SEQ ID NO: 15)
havwh;

(k)
                                            (SEQ ID NO: 16)
wvplw;
```

-continued (l)

(SEQ ID NO: 17)

ffrly; and (m)

(SEQ ID NO: 18)

wvvGf, and wherein the second ligand comprises an amino acid sequence chosen from:

(a)

(SEQ ID NO: 19)

AGDSW;

(b)

(SEQ ID NO: 20)

HVRHG;

(c)

(SEQ ID NO: 21)

HGRGH;

(d)

(SEQ ID NO: 22)

THPTT;

(e)

(SEQ ID NO: 23)

FAGYH;

(f)

(SEQ ID NO: 24)

WTEHG;

(g)

(SEQ ID NO: 25)

PWTHG;

(h)

(SEQ ID NO: 26)

TNDFD;

(i)

(SEQ ID NO: 27)

LFPFD;

(j)

(SEQ ID NO: 28)

slrfG;

(k)

(SEQ ID NO: 29)

yfrGs;

(l)

(SEQ ID NO: 30)

wnwvG;

-continued (m)

(SEQ ID NO: 31)

vawlG;

(n)

(SEQ ID NO: 32)

fhvhG;

(o)

(SEQ ID NO: 33)

wvsnv;

(p)

(SEQ ID NO: 34)

wsvnv;

(q)

(SEQ ID NO: 35)

lnshG;

(r)

(SEQ ID NO: 36)

yGGvr;

(s)

(SEQ ID NO: 37)

nsvhG;

(t)

(SEQ ID NO: 38)

ttvhG;

(u)

(SEQ ID NO: 39)

fdvGh;

(v)

(SEQ ID NO: 40)

rhGwk; and (w)

(SEQ ID NO: 49)

hGrGh.

10. The synthetic capture agent of claim 9, wherein the first ligand comprises wlprf (SEQ ID NO: 13) and the second ligand comprises HGRGH (SEQ ID NO: 21).

11. The synthetic capture agent of claim 9, wherein the first ligand comprises AKYRG (SEQ ID NO: 8) and the second ligand comprises HGRGH (SEQ ID NO: 21).

12. The synthetic capture agent of claim 9, wherein the first ligand comprises AKYRG (SEQ ID NO: 8) and the second ligand comprises PWTHG (SEQ ID NO: 25).

13. A method for detecting CD8 in a biological sample, comprising contacting the biological sample with one or more synthetic capture agents of claim 9, wherein the one or more synthetic capture agents are labeled with a detectable moiety, and detecting the detectable moiety when the one or more synthetic capture agents bind to CD8 in the biological sample.

* * * * *

SEQUENCE LISTING

<160> NUMBER OF SEQ ID NOS: 55

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Ser Gln Phe Arg Val Ser Pro Leu Asp
1               5

<210> SEQ ID NO 2
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 2

Ser Gln Phe Arg Val Ser Pro Leu Asp Arg Thr Trp Asn Leu Gly Glu
1               5                   10                  15

Thr Val Glu Leu Lys Ser Gln
            20

<210> SEQ ID NO 3
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 3

Phe Leu Leu Tyr Leu Ser Gln Asn Lys Pro
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Ala Ala Glu Gly Leu Asp Thr Gln Arg
1               5

<210> SEQ ID NO 5
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 5

Phe Leu Leu Tyr Leu Ser Gln Asn Lys Pro Lys Ala Ala Glu Gly Leu
1               5                   10                  15

Asp Thr Gln Arg
            20

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 6

His Gly Ser Tyr Gly
1               5

<210> SEQ ID NO 7

-continued

```
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 7

Lys Arg Leu Gly Ala
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 8

Ala Lys Tyr Arg Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(5)

<400> SEQUENCE: 9

His Ala Leu Leu Trp
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(2)
<223> OTHER INFORMATION: D-amino acid
<220> FEATURE:
<221> NAME/KEY: VARIANT
<222> LOCATION: (4)..(5)
<223> OTHER INFORMATION: D-amino acid

<400> SEQUENCE: 10

Leu Arg Gly Tyr Trp
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(5)
<223> OTHER INFORMATION: D-amino acid

<400> SEQUENCE: 11

Val Ala Ser His Phe
1               5
```

-continued

```
<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(1)
<223> OTHER INFORMATION: D-amino acid
<220> FEATURE:
<221> NAME/KEY: VARIANT
<222> LOCATION: (3)..(5)
<223> OTHER INFORMATION: D-amino acid

<400> SEQUENCE: 12

Asn Gly Asn Val His
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(5)
<223> OTHER INFORMATION: D-amino acid

<400> SEQUENCE: 13

Trp Pro Leu Arg Phe
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(5)
<223> OTHER INFORMATION: D-amino acid

<400> SEQUENCE: 14

Arg Trp Phe Asn Val
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(5)
<223> OTHER INFORMATION: D-amino acid

<400> SEQUENCE: 15

His Ala Val Trp His
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
```

-continued

```
<221> NAME/KEY: VARIANT
<222> LOCATION: (1)..(5)
<223> OTHER INFORMATION: D-amino acid

<400> SEQUENCE: 16

Trp Val Pro Leu Trp
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(5)
<223> OTHER INFORMATION: D-amino acid

<400> SEQUENCE: 17

Phe Phe Arg Leu Tyr
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(3)
<223> OTHER INFORMATION: D-amino acid
<220> FEATURE:
<221> NAME/KEY: VARIANT
<222> LOCATION: (5)..(5)
<223> OTHER INFORMATION: D-amino acid

<400> SEQUENCE: 18

Trp Tyr Tyr Gly Phe
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 19

Ala Gly Asp Ser Trp
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 20

His Val Arg His Gly
1               5

<210> SEQ ID NO 21
<211> LENGTH: 5
<212> TYPE: PRT
<213> ORGANISM: Artificial Sequence
<220> FEATURE:
```

<223> OTHER INFORMATION: Synthetic Peptide

<400> SEQUENCE: 21

His Gly Arg Gly His
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 22

Thr His Pro Thr Thr
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 23

Phe Ala Gly Tyr His
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 24

Trp Thr Glu His Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 25

Pro Trp Thr His Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 26

Thr Asn Asp Phe Asp
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide -continued

```
<400> SEQUENCE: 27

Leu Phe Pro Phe Asp
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(4)
<223> OTHER INFORMATION: D-amino acid

<400> SEQUENCE: 28

Ser Leu Arg Phe Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(3)
<223> OTHER INFORMATION: D-amino acid
<220> FEATURE:
<221> NAME/KEY: VARIANT
<222> LOCATION: (5)..(5)
<223> OTHER INFORMATION: D-amino acid

<400> SEQUENCE: 29

Tyr Phe Arg Gly Ser
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(4)
<223> OTHER INFORMATION: D-amino acid

<400> SEQUENCE: 30

Trp Asn Trp Val Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(4)
<223> OTHER INFORMATION: D-amino acid

<400> SEQUENCE: 31

Val Ala Trp Leu Gly
1               5
```

```
<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(4)
<223> OTHER INFORMATION: D-amino acid

<400> SEQUENCE: 32

Phe His Val His Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(5)
<223> OTHER INFORMATION: D-amino acid

<400> SEQUENCE: 33

Trp Val Ser Asn Val
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(5)
<223> OTHER INFORMATION: D-amino acid

<400> SEQUENCE: 34

Trp Ser Val Asn Val
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(4)
<223> OTHER INFORMATION: D-amino acid

<400> SEQUENCE: 35

Leu Asn Ser His Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(1)
<223> OTHER INFORMATION: D-amino acid
<220> FEATURE:
```

```
<221> NAME/KEY: VARIANT
<222> LOCATION: (4)..(5)
<223> OTHER INFORMATION: D-amino acid

<400> SEQUENCE: 36

Tyr Gly Gly Val Arg
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(4)
<223> OTHER INFORMATION: D-amino acid

<400> SEQUENCE: 37

Asn Ser Val His Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(4)
<223> OTHER INFORMATION: D-amino acid

<400> SEQUENCE: 38

Thr Thr Val His Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(3)
<223> OTHER INFORMATION: D-amino acid
<220> FEATURE:
<221> NAME/KEY: VARIANT
<222> LOCATION: (5)..(5)
<223> OTHER INFORMATION: D-amino acid

<400> SEQUENCE: 39

Phe Asp Val Gly His
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(2)
<223> OTHER INFORMATION: D-amino acid
<220> FEATURE:
<221> NAME/KEY: VARIANT
<222> LOCATION: (4)..(5)
<223> OTHER INFORMATION: D-amino acid
```

<400> SEQUENCE: 40

Arg His Gly Trp Lys
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(5)
<223> OTHER INFORMATION: D-amino acid

<400> SEQUENCE: 41

Gly His Thr Trp Pro
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 42

Ala Ala Glu Gly Leu Asp
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 43

Arg Val Ser Pro Leu Asp
1               5

<210> SEQ ID NO 44
<211> LENGTH: 161
<212> TYPE: PRT
<213> ORGANISM: Homo sapiens

<400> SEQUENCE: 44

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala

-continued

```
             115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160

Asp

<210> SEQ ID NO 45
<211> LENGTH: 169
<212> TYPE: PRT
<213> ORGANISM: Homo sapiens

<400> SEQUENCE: 45

Lys Pro Gln Ala Pro Glu Leu Arg Ile Phe Pro Lys Lys Met Asp Ala
1                   5                   10                  15

Glu Leu Gly Gln Lys Val Asp Leu Val Cys Glu Val Leu Gly Ser Val
                20                  25                  30

Ser Gln Gly Cys Ser Trp Leu Phe Gln Asn Ser Ser Ser Lys Leu Pro
            35                  40                  45

Gln Pro Thr Phe Val Val Tyr Met Ala Ser Ser His Asn Lys Ile Thr
    50                  55                  60

Trp Asp Glu Lys Leu Asn Ser Ser Lys Leu Phe Ser Ala Met Arg Asp
65                  70                  75                  80

Thr Asn Asn Lys Tyr Val Leu Thr Leu Asn Lys Phe Ser Lys Glu Asn
                85                  90                  95

Glu Gly Tyr Tyr Phe Cys Ser Val Ile Ser Asn Ser Val Met Tyr Phe
            100                 105                 110

Ser Ser Val Val Pro Val Leu Gln Lys Val Asn Ser Thr Thr Thr Lys
            115                 120                 125

Pro Val Leu Arg Thr Pro Ser Pro Val His Pro Thr Gly Thr Ser Gln
    130                 135                 140

Pro Gln Arg Pro Glu Asp Cys Arg Pro Arg Gly Ser Val Lys Gly Thr
145                 150                 155                 160

Gly Leu Asp Phe Ala Cys Asp Ile Tyr
                165

<210> SEQ ID NO 46
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(1)
<223> OTHER INFORMATION: propargylglycine
<220> FEATURE:
<221> NAME/KEY: VARIANT
<222> LOCATION: (2)..(6)
<223> OTHER INFORMATION: any amino acid except cysteine, methionine,
      isoleucine, and glutamine

<400> SEQUENCE: 46

Xaa Xaa Xaa Xaa Xaa Xaa Met
1                   5

<210> SEQ ID NO 47
<211> LENGTH: 7
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: VARIANT
<222> LOCATION: (1)..(1)
<223> OTHER INFORMATION: propargylglycine
<220> FEATURE:
<221> NAME/KEY: VARIANT
<222> LOCATION: (1)..(7)
<223> OTHER INFORMATION: D-amino acid
<220> FEATURE:
<221> NAME/KEY: VARIANT
<222> LOCATION: (2)..(6)
<223> OTHER INFORMATION: any amino acid except cysteine, methionine,
      isoleucine, and glutamine

<400> SEQUENCE: 47

Xaa Xaa Xaa Xaa Xaa Xaa Met
1               5

<210> SEQ ID NO 48
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(1)
<223> OTHER INFORMATION: propargylglycine
<220> FEATURE:
<221> NAME/KEY: VARIANT
<222> LOCATION: (1)..(6)
<223> OTHER INFORMATION: D-amino acid
<220> FEATURE:
<221> NAME/KEY: VARIANT
<222> LOCATION: (2)..(6)
<223> OTHER INFORMATION: no amino acid or an amino acid selected from
      glycine, alanine, leucine, proline, serine, threonine, and
      aminoisobutyric acid
<220> FEATURE:
<221> NAME/KEY: VARIANT
<222> LOCATION: (7)..(11)
<223> OTHER INFORMATION: amino acids 7-11 are a macrocycle selected from
      AKYRG; D-amino acids wplrf; D-amino acids ffrly; and D-amino acids
      rwfnv

<400> SEQUENCE: 48

Xaa Xaa Xaa Xaa Xaa Xaa Xaa Xaa Xaa Xaa Xaa Met
1               5                   10

<210> SEQ ID NO 49
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (1)..(1)
<223> OTHER INFORMATION: D-amino acid
<220> FEATURE:
<221> NAME/KEY: VARIANT
<222> LOCATION: (3)..(3)
<223> OTHER INFORMATION: D-amino acid
<220> FEATURE:
<221> NAME/KEY: VARIANT
<222> LOCATION: (5)..(5)
<223> OTHER INFORMATION: D-amino acid

<400> SEQUENCE: 49

His Gly Arg Gly His
1               5
```

-continued

```
<210> SEQ ID NO 50
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 50

Ser Gln Phe Arg Val Ser Pro Leu Asp Arg Gly Gly Gly Gly Gly
1               5                   10                  15

Gly Gly Gly Gly Gly Gly Gly
            20

<210> SEQ ID NO 51
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 51

Gly Gly Gly Gly Gly Gly Gly Gly Gly Arg Thr Trp Asn Leu Gly Glu
1               5                   10                  15

Thr Val Glu Leu Lys Ser Gln
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 52

Phe Leu Leu Tyr Leu Ser Gln Asn Lys Pro Lys Gly Gly Gly Gly Gly
1               5                   10                  15

Gly Gly Gly Gly
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 53

Gly Gly Gly Gly Gly Gly Gly Gly Gly Gly Lys Ala Ala Glu Gly Leu
1               5                   10                  15

Asp Thr Gln Arg
            20

<210> SEQ ID NO 54
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: L-azidolysine

<400> SEQUENCE: 54

Ser Gln Phe Arg Val Ser Pro Leu Asp Xaa Thr Trp Asn Leu Gly Glu
```

-continued

```
1               5               10              15

Thr Val Glu Leu Lys Ser Gln
                20

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: L-azidolysine

<400> SEQUENCE: 55

Phe Leu Leu Tyr Leu Ser Gln Asn Lys Pro Xaa Ala Ala Glu Gly Leu
1               5               10              15

Asp Thr Gln Arg
                20
```